US012636016B2

(12) United States Patent
Uesaka et al.

(10) Patent No.: US 12,636,016 B2
(45) Date of Patent: May 26, 2026

(54) ENDOSCOPE CLIP AND OPERATION METHOD FOR CLIP ARM

(71) Applicant: OLYMPUS CORPORATION, Hachioji (JP)

(72) Inventors: Kensuke Uesaka, Hino (JP); Megumi Minosawa, Hachioji (JP); Yuya Hidaka, Fuchu (JP); Naoki Fujikawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1151 days.

(21) Appl. No.: 17/308,443

(22) Filed: May 5, 2021

(65) Prior Publication Data

US 2021/0251633 A1      Aug. 19, 2021

Related U.S. Application Data

(63) Continuation of application No. PCT/JP2018/041600, filed on Nov. 9, 2018.

(51) Int. Cl.
*A61B 17/122* (2006.01)
*A61B 17/00* (2006.01)
*A61B 17/128* (2006.01)

(52) U.S. Cl.
CPC ...... *A61B 17/122* (2013.01); *A61B 17/00234* (2013.01); *A61B 17/1227* (2013.01); *A61B 17/1285* (2013.01); *A61B 2017/00296* (2013.01)

(58) Field of Classification Search
CPC .......... A61B 17/00234; A61B 17/1285; A61B 17/122; A61B 17/1227
See application file for complete search history.

(56) References Cited

U.S. PATENT DOCUMENTS 6,210,398 B1 * 4/2001 Ouchi ................ A61B 17/2909
600/184
2002/0045909 A1 4/2002 Kimura et al.
2002/0128667 A1 9/2002 Kobayashi et al.
2003/0083677 A1 5/2003 Damarati
2006/0190015 A1 8/2006 Matsuno et al.
(Continued)

FOREIGN PATENT DOCUMENTS

CN      107405046 A      11/2017
JP      S50-038691 U     4/1975
(Continued)

OTHER PUBLICATIONS

May 23, 2024 Notice of Allowance issued in U.S. Appl. No. 17/313,252.
(Continued)

*Primary Examiner* — Erin Mcgrath
(74) *Attorney, Agent, or Firm* — Oliff PLC

(57)      ABSTRACT
An endoscope clip can include an arm portion that can move into the following configurations: a closed configuration, a first open configuration in which the pair of arms are separated at a first distance, and a second open configuration in which the pair of arms are separated at a second distance larger than the first distance. The endoscope clip can also include an operation wire and a restriction portion configured to restrict movement of the operation wire to fix the arm portion in one of the possible configurations.

14 Claims, 47 Drawing Sheets

(56)        References Cited

U.S. PATENT DOCUMENTS

| | | |
|---|---|---|
| 2015/0018848 A1 | 1/2015 | Kappel et al. |
| 2015/0112367 A1 | 4/2015 | Damarati |
| 2017/0215886 A1 | 8/2017 | Muyari et al. |
| 2020/0008811 A1* | 1/2020 | Itoh .................... A61B 17/1285 |
| 2020/0113572 A1 | 4/2020 | Tsuchiya et al. |

FOREIGN PATENT DOCUMENTS

| | | |
|---|---|---|
| JP | 2010-136818 A | 6/2010 |
| JP | 2013-085859 A | 5/2013 |
| JP | 2013-085860 A | 5/2013 |
| JP | 5750620 B2 | 7/2015 |
| WO | 2018/011846 A1 | 1/2018 |
| WO | 2018/011847 A1 | 1/2018 |
| WO | WO-2018173474 A1 * | 9/2018 ......... A61B 17/1285 |

OTHER PUBLICATIONS

Feb. 5, 2019 International Search Report issued in International Patent Application No. PCT/JP2018/041600.

Feb. 15, 2024 Office Action issued in U.S. Appl. No. 17,313,252.

Sep. 21, 2023 Office Action issued in Chinese Patent Application No. 201880099212.6.

Feb. 5, 2019 International Search Report issued in International Patent Application No. PCT/JP2018/014599.

Oct. 17, 2022 Extended European Search Report issued in European Patent Application No. 18939358.0.

Sep. 12, 2023 Office Action issued in Chinese Patent Application No. 201880099211.1.

* cited by examiner

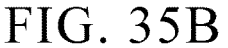
FIG. 35B
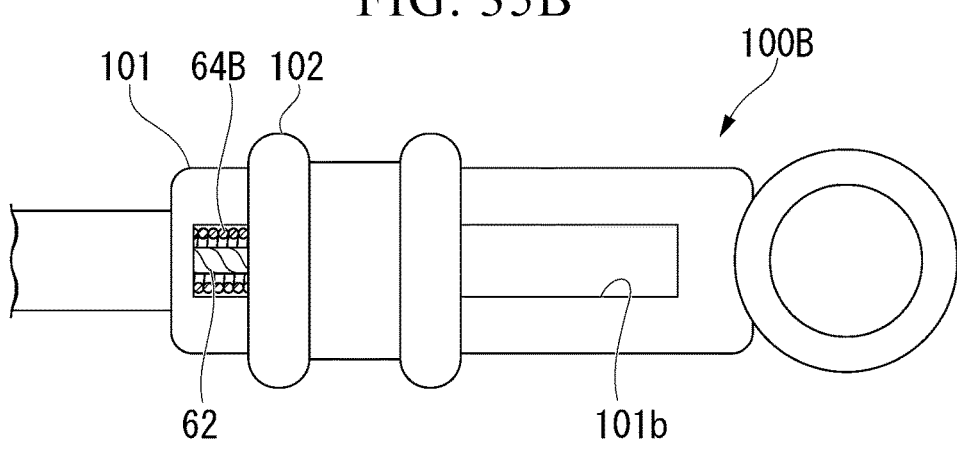
FIG. 36A
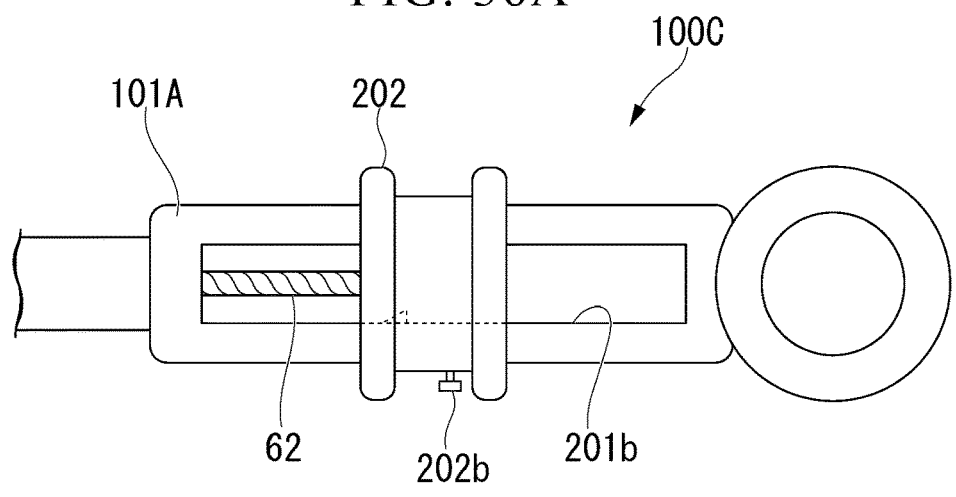
FIG. 36B
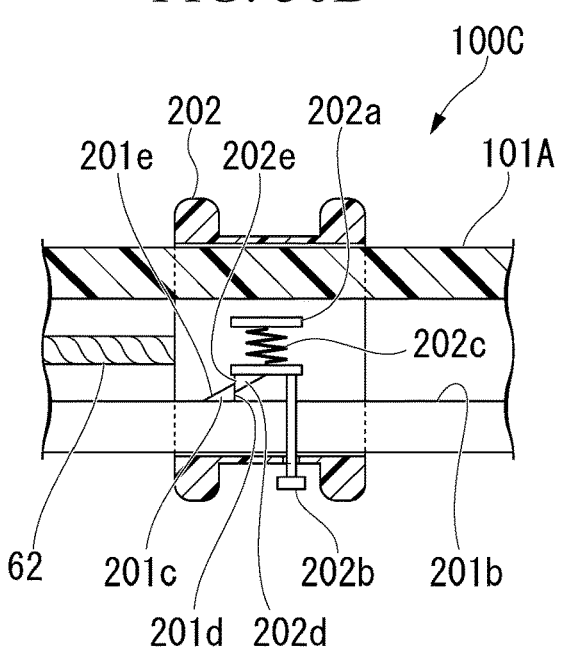

FIG. 36C
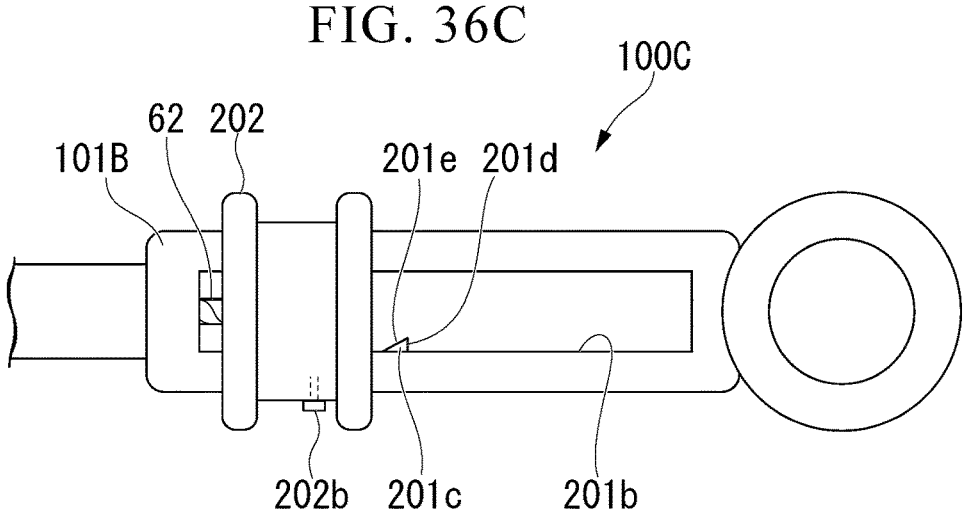
FIG. 37
FIG. 38
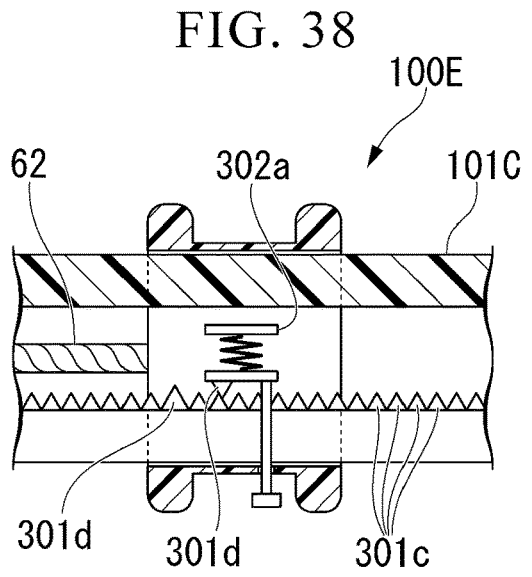

ENDOSCOPE CLIP AND OPERATION METHOD FOR CLIP ARM

This application is a continuation application of PCT International Application No. PCT/JP2018/041600, filed on Nov. 9, 2018. The content of the PCT International Application is incorporated herein by reference.

TECHNICAL FIELD

The present disclosure relates to an endoscope clip configured for ligating tissues and an operation method for clip arm.

BACKGROUND ART

Conventionally known is an endoscope clip which is introduced into the body of a patient via a channel of an endoscope for a usage of ligating the openings and blood vessels formed in the tissue. An endoscopic treatment tool as described in Japanese Patent (Granted) No. 5750620 is known as such endoscope clip.

The endoscope treatment tool described in Japanese Patent (Granted) No. 5750620 includes a clip unit and a treatment tool body.

The clip unit has a clip main body, a pressing tube, and a spiral spring. The clip main body has a first arm and a second arm. The first arm and the second arm are separated from each other with a space between a distal end of the first arm and a distal end of the second arm in a natural state.

The treatment tool main body has an outer tube, an insertion portion, and an operating member. The insertion portion is inserted through the outer tube so as to be advanceable and retractable, and the insertion portion has a sheath, an operation wire, and a connection member. The operation wire is inserted into the sheath, wherein a distal end thereof is connected to the connection member, and a proximal end thereof is connected to a slider described below. The connection member is provided to connect the clip main body and the operation wire. The operating member is attached to a proximal end side of the insertion portion, and the operating member has an operating portion main body, a slider, and a breaking mechanism. The slider is configured to be advanceable and retractable with respect to the operating portion main body by engaging with a slit of the operating portion main body. The breaking mechanism is built in the operating member. When a tension applying to the breaking mechanism reaches or exceeds a predetermined tensile strength, the breaking mechanism is broken.

The endoscope treatment tool disclosed in Japanese Patent (Granted) No. 5750620 is used as follows.

An operator inserts the endoscope having the channel into the body of the patient. Next, the operator inserts the outer tube from the proximal end portion of the channel of the endoscope and projects the outer tube from the distal end portion of the channel of the endoscope. Subsequently, the operator pulls the outer tube back with respect to the insertion portion of the treatment tool main body to cause the clip main body to project from the distal end side of the outer tube. As a result, the first arm and the second arm of the clip main body enter an open configuration in which there is a gap generated between the first arm and the second arm.

When the operator directs the clip unit toward the target tissue inside the body of the patient while observing the inside of the body of the patient using the endoscope, the target tissue is located between the first arm and the second arm. In this state, when the operator pulls the operation wire toward the proximal end side, the first arm and the second arm are brought into a closed configuration in which the first arm and the second arm are in contact with each other so as to grasp the target tissue. When the operator further pulls the operation wire toward the proximal side, the target tissue is moved toward the proximal side while being grasped by the clip main body. Even when the target tissue is grasped by the clip main body, when the operator pushes the operation wire toward the distal end side, the first arm and the second arm of the clip main body enter the open configuration such that it is possible to grasp the target tissues again.

SUMMARY

According to an aspect of the present disclosure, an endoscope clip includes an arm portion configured from a pair of arms, the arm portion having a first open configuration in which the pair of arms are separated from each other at a first distance and a second open configuration in which the pair of arms are separated from each other at a second distance larger than the first distance; an operation wire having a distal end connected to the arm portion to be attachable to and detachable from the arm portion, the operation wire being configured to cause the arm portion to be transitioned from the first open configuration to the second open configuration by moving toward a distal end side; and a restriction portion configured to restrict movement of the operation wire toward the distal end side so as to restrict transition of the arm portion from the first open configuration to the second open configuration by applying a force opposite to a force for moving the operation wire toward the distal end side to the operation wire when the arm portion is in the first open configuration.

According to another aspect of the present disclosure, An endoscope clip includes a clip arm (11) having a first arm (12) and a second arm (13) and extending along a longitudinal axis; an operator (100) configured to cause the clip arm to be transitioned to a closed configuration, a first open configuration, and a second open configuration, wherein the closed configuration is a configuration in which the first arm and the second arm are closed, the first open configuration is a configuration in which the first arm and the second arm are separated from each other at a first distance (W1) compared to the closed configuration, and the second open configuration is a configuration in which the first arm and the second arm are separated from each other at a second distance (W2) larger than the first distance; and a restrictor (limiting portion) 64 configured to perform a restriction to a transition of the clip arm from the first open configuration to the second open configuration and to release the restriction.

According to a further aspect of the present disclosure, an operation method for a clip arm, the clip arm including a first arm and a second arm, the clip arm being configured to be transitioned to a closed configuration in which the first arm and the second arm are closed, a first a first open configuration in which the first arm and the second arm are separated from each other at a first distance compared to the closed configuration, and a second open configuration in which the first arm and the second arm are separated from each other at a second distance larger than the first distance, and the transition from the first open configuration to the second configuration is restricted, the operation method for a clip arm including releasing a restriction to the transition of the clip arm from the first open configuration to the second configuration; and causing the clip arm to be transitioned from the first open configuration to the second configuration after the restriction is released.

BRIEF DESCRIPTION OF DRAWINGS

FIG. 1 is a cross-sectional side view schematically showing a configuration of an endoscope clip according to a first embodiment of the present disclosure.

FIG. 35B is a side view showing movement of the operation portion according to the present modification.

FIG. 36A is a side view showing a configuration of an operation portion of an endoscope clip according to a third modification of the present disclosure.

FIG. 36B is a cross-sectional side view showing the configuration of the operation portion according to the present modification.

FIG. 36C is a side view showing the configuration of the operation portion according to the present modification.

FIG. 37 is a side view showing a configuration of an operation portion of an endoscope clip according to a fourth modification of the present disclosure.

FIG. 38 is a side view showing a configuration of an operation portion of an endoscope clip according to a fifth modification of the present disclosure.

DESCRIPTION OF EMBODIMENTS

First Embodiment

Hereinafter, a configuration of an endoscope clip according to a first embodiment of the present invention will be described with reference to FIGS. 1 to 10D.

The endoscope clip 1 according to the present embodiment is used by being inserted into a body of a patient body through a channel formed in an endoscope (not shown). In the present specification, a side on which the endoscope operation portion for the operator to operate the endoscope is located is defined as a proximal side, and a side on which a distal end portion of the endoscope inserted into the body is located is defined as a distal end side.

Figure 1:
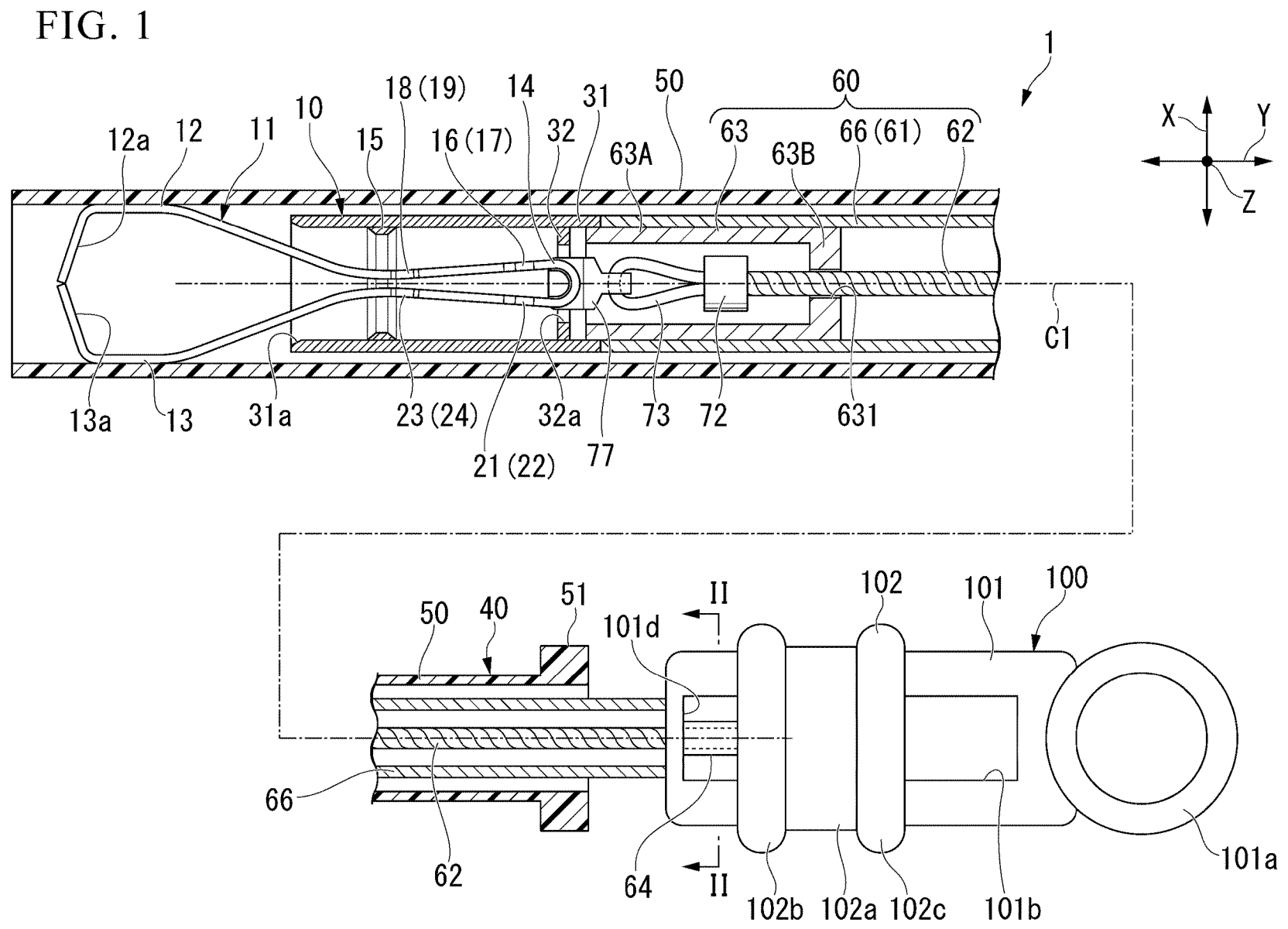
Figure 2:
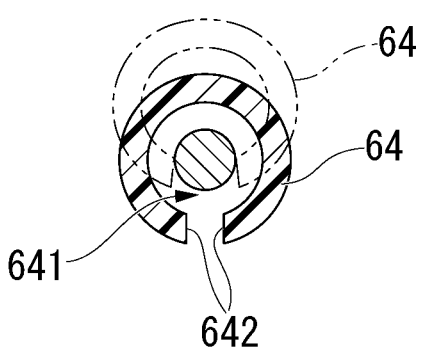
FIG. 2 is a cross-sectional view showing a limiting portion broken along a cutting line II-II and viewed from a proximal end of the endoscope clip shown in FIG. 1.
Figure 3:
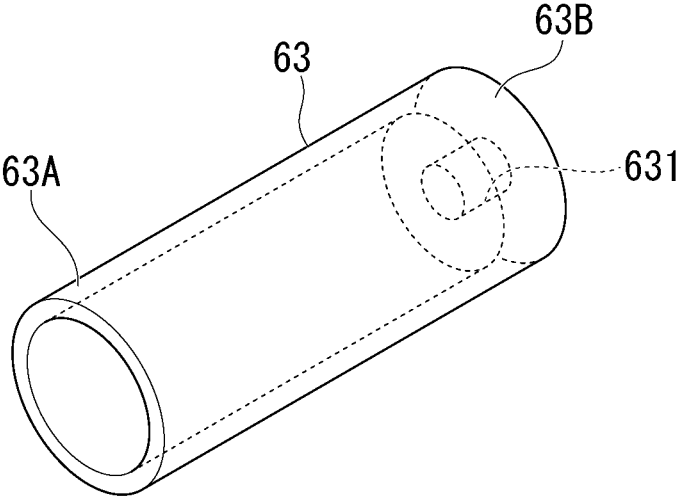
FIG. 3 is a perspective view showing a connection member of the endoscope clip according to the present embodiment.

FIG. 1 is a cross-sectional side view showing an initial state of the endoscope clip 1 according to the present embodiment. FIG. 1 is a cross-sectional side view of a clip 10 taken along a plane passing through an axis C1 of a pressing tube 31 described below. FIG. 2 is a cross-sectional view of a hollow tubular limiting portion 64 disposed in the operation portion 100 of the endoscope clip 1 according to the present embodiment that is taken along the cutting line II-II. FIG. 3 is a perspective view showing a configuration of a connection member 63 of the endoscope clip according to the present embodiment.

As shown in FIG. 1, the endoscope clip 1 includes a clip unit (hereinafter, described as "clip") 10 and a treatment tool main body (applicator) 40. The clip 10 is detachably connected to a distal end portion of the treatment tool main body 40. According to the present embodiment, the clip 10 and the treatment tool body 40 are connected by a connection member 63 to be integrally configured.

As shown in FIG. 1, the clip 10 has an arm member (arm portion, clip arm) 11 configured from a first arm 12 and a second arm 13. According to the present embodiment, an opposite direction X in which the first arm 12 and the second arm 13 face each other, an axial direction Y parallel to the axis C1 of the pressing tube 31, and an orthogonal direction Z that is orthogonal to each of the opposite direction X and the axial direction Y are defined. In this specification, for convenience of description, the axis C1 is regarded as an axis of the clip 10 and an insertion portion 60 described later.

(Configuration of Clip 10)

As shown in FIG. 1, the clip 10 includes an arm member 11 and a pressing tube 31.

The pressing tube 31 is formed in a cylindrical shape and has an inner diameter into which a proximal end portion of the arm member 11 is able to enter. That is, a lumen into which the arm member 11 having the first arm 12 and the second arm 13 described below may enter is formed in the pressing tube 31.

(Configuration of Arm Member 11)

The arm member 11 has a first arm 12, a second arm 13, and a central portion 14. The first arm 12 and the second arm 13 are configured to extend from the proximal end side toward the distal end side and are arranged to face each other. The central portion 14 is located between the proximal end portion of the first arm 12 and the proximal end portion of the second arm 13. As shown in the side view in FIG. 1A, the first arm 12 and the second arm 13 is formed at positions to be line-symmetrical with respect to the axis C1.

In a natural state, the first arm 12 and the second arm 13 are separated from each other, and a distance between the first arm 12 and the second arm 13 increases along a direction from the proximal end side toward the distal end side. In the present specification, the "natural state" refers to a state in which an external force is not applied to the arm member 11. For example, a state in which a force by an inner circumferential surface of the pressing tube 31 does not apply to the first arm 12 and the second arm 13 of the arm member 11 is the natural state. A claw 12a extending toward the second arm 13 side is formed at the distal end portion of the first arm 12. A claw 13a extending toward the first arm 12 side is formed at a distal end portion of the second arm 13.

The first arm 12 and the second arm 13 are formed to have a rounded shape that a cross-sectional shape orthogonal to a longitudinal direction at the distal end side is an arc shape. The first arm 12 and the second arm 13 are configured in such a manner so as to have improved strength against bending and reduce frictional resistance to the outer sheath 50 described below so as to smoothly advance and retract.

Figure 4A:
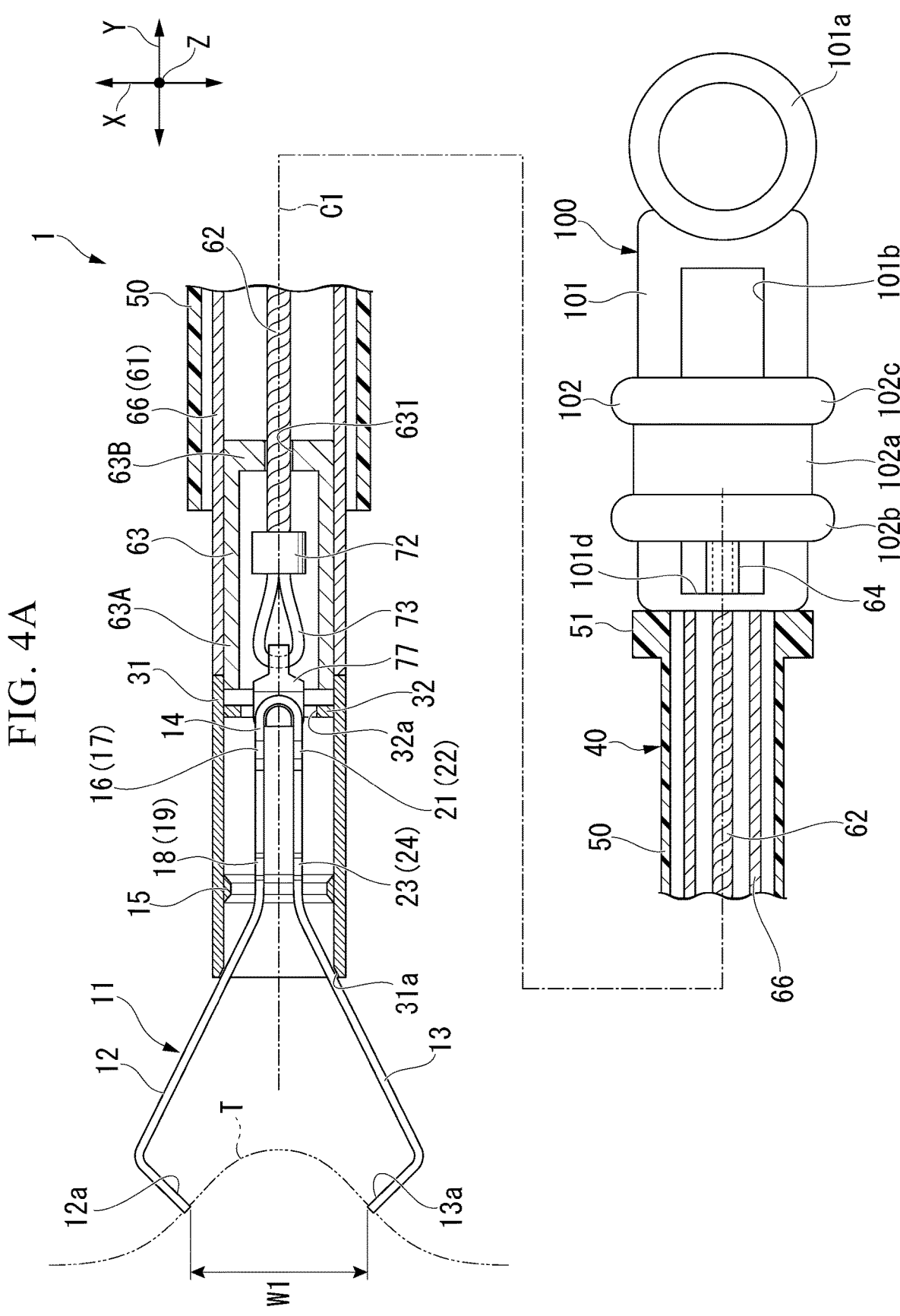
FIG. 4A is a cross-sectional perspective view schematically showing the endoscope clip according to the present embodiment.
Figure 4B:
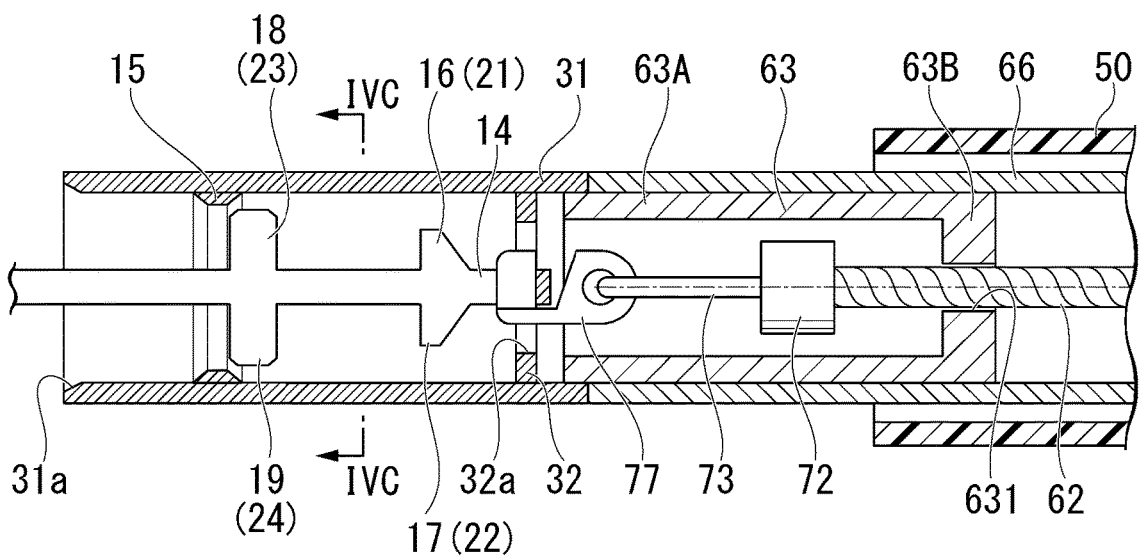
FIG. 4B is a cross-sectional planar view schematically showing a distal end portion of the endoscope clip according to the present embodiment shown in FIG. 4A.
Figure 4B:
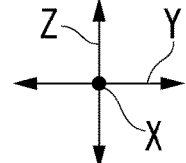

As shown in FIG. 4B, two first locked portions 16, 17 are provided at the proximal end portion of the first arm 12. The first locked portions 16, 17 are provided on a reference plane parallel to the axis line (central axis line) C1 of the pressing tube 31 so as to project from a lateral surface of the first arm 12 in the orthogonal direction Z. The first locked portions 16, 17 project in directions opposite to each other.

In the planar view shown in FIG. 4B, the first locked portion 16 and the first locked portion 17 are line-symmetric with respect to the axis C1. As shown in FIG. 4B, a proximal end surface 16a of the first locked portion 16 is inclined to be separated from the first arm 12 (center axis C1) toward the distal end side. A distal end surface 16b of the first locked portion 16 is orthogonal to the axial direction Y. A proximal end surface 17a of the first locked portion 17 and the proximal end surface 16a of the first locked portion 16 are line-symmetric with respect to the axis C1. The distal end surface 17b of the first locked portion 17 and the distal end surface 16b of the first locked portion 16 are line-symmetric with respect to the axis C1.

As shown in FIG. 1, in the first arm 12, two protrusions 18, 19 are provided at a more distal end side of the first locked portions 16, 17 of the first arm 12 respectively. As shown in FIG. 4B, the protrusions 18 and 19 protrude from a lateral surface of the first arm 12 in the orthogonal direction Z. The protrusion 18 and the protrusion 19 are line-symmetric with respect to the axis C1 in a planar view. Lengths of the protrusions 18, 19 protruding from the first arm 12 may be longer than the length of the first locked portions 16, 17 protruding from the first arm 12 in the orthogonal direction Z, respectively.

Second locked portions 21, 22 and second protrusions 23, 24 which are formed in the same manner as the first locked portions 16, 17 and the protrusions 18, 19 of the first arm 12 are provided in the second arm 13. In other words, the second locked portions 21, 22 of the second arm 13 protrude from the lateral surface of the second arm 13 in the orthogonal direction Z which is a direction in which the second arm 13 is separated from the first arm 12. The protrusions 23, 24 of the second arm 13 project in the orthogonal direction Z from the lateral surface of the second arm 13 at a more distal end side of the second locked portions 21, 22 of the second arm 13. The second locked portions 21, 22 and the protrusions 23, 24 are arranged in the opposition direction X with respect to the first locked portions 16, 17 and the protrusions 18, 19 respectively. In the planar view shown in FIG. 4B, the second locked portions 21, 22 overlap the first locked portions 16, 17, and the protrusions 23, 24 overlap protrusions 18, 19, respectively.

(Configuration of Pressing Tube 31)

A step portion (engaging portion) 15 is provided to protrude toward the inner side of the pressing tube 31 over the entire circumference on the inner circumferential surface of the pressing tube 31. The pressing tube 31 has a smaller inner diameter at the position where the step portion 15 is provided. According to the present embodiment, the position where the step portion 15 is provided on the inner circumferential surface along the longitudinal direction of the pressing tube 31 is not particularly limited. For example, the step portion 15 may be provided on the inner circumferential surface on the distal end side of the pressing tube 31.

According to the present embodiment, the protrusions (engaged portions) 18, 19, 23, 24 provided on the arm member 11 engage with the step portion 15, so as to restrict advancement of the arm member 11 with respect to the pressing tube 31. A shape of the step portion 15 including the length protruding toward the inner side of the pressing tube 31 is not particularly limited, for example, the step portion 15 may be provided according to the shape of the protrusions 18, 19, 23, 24 of the arm member 11 described below. More specifically, for example, an inclined surface may be provided at the distal end side and the proximal end side of the step portion 15 along the longitudinal direction of the pressing tube 31. Corresponding to the inclined surface provided in the step portion 15, inclined surface may be provided at both ends of the protrusions 18, 19, 23, 24 in the radial direction. The step portion 15 and the protrusions 18, 19, 23, 24 according to the present embodiment are configured in this manner such that when the arm member 11 is advanced and retracted along the longitudinal direction of the pressing tube 31, it is easy for the protrusions 18, 19, 23 and 24 to advance and retract while contacting the step portion 15.

An locking portion 32 is formed to protrude toward the inner side of the pressing tube 31 and formed on the inner circumferential surface of the pressing tube 31 located on the proximal end side more than the step portion 15. In other words, the locking portion 32 is formed to protrude from the inner circumferential surface of the pressing tube 31 in the direction toward the axis C1. According to the present embodiment, in order to secure a space for press-fitting a connection member 63 described below from the opening on the proximal end side of the pressing tube 31, the locking portion 32 is formed at the distal end side more than the proximal end of the pressing tube 31 with a predetermined distance. That is, in the pressing tube 31, the locking portion 32 is formed at a position between the proximal end of the pressing tube 31 and the step portion 15.

Figure 7A:
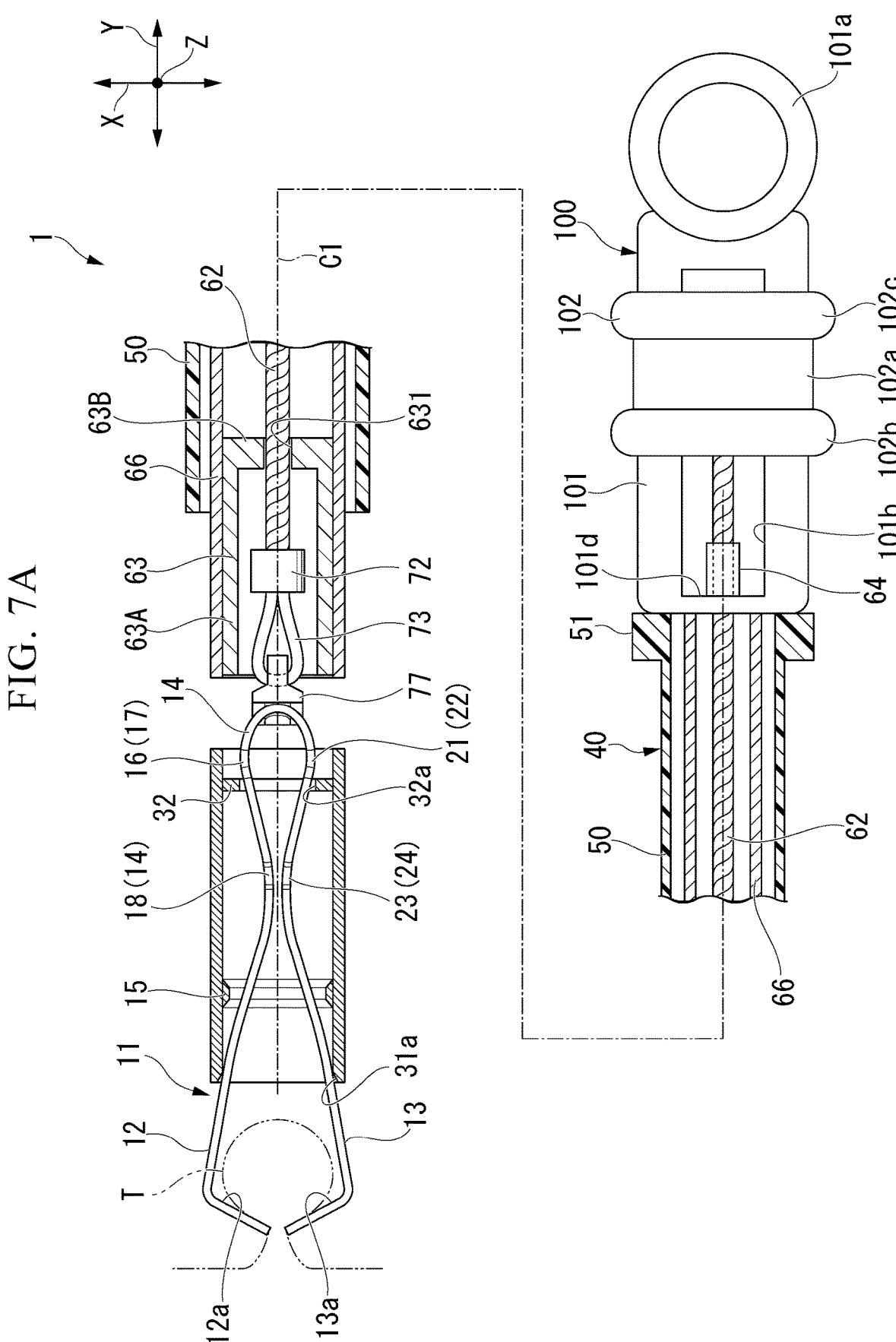
FIG. 7A is a cross-sectional side view schematically showing the endoscope clip according to the present embodiment.
Figure 7B:
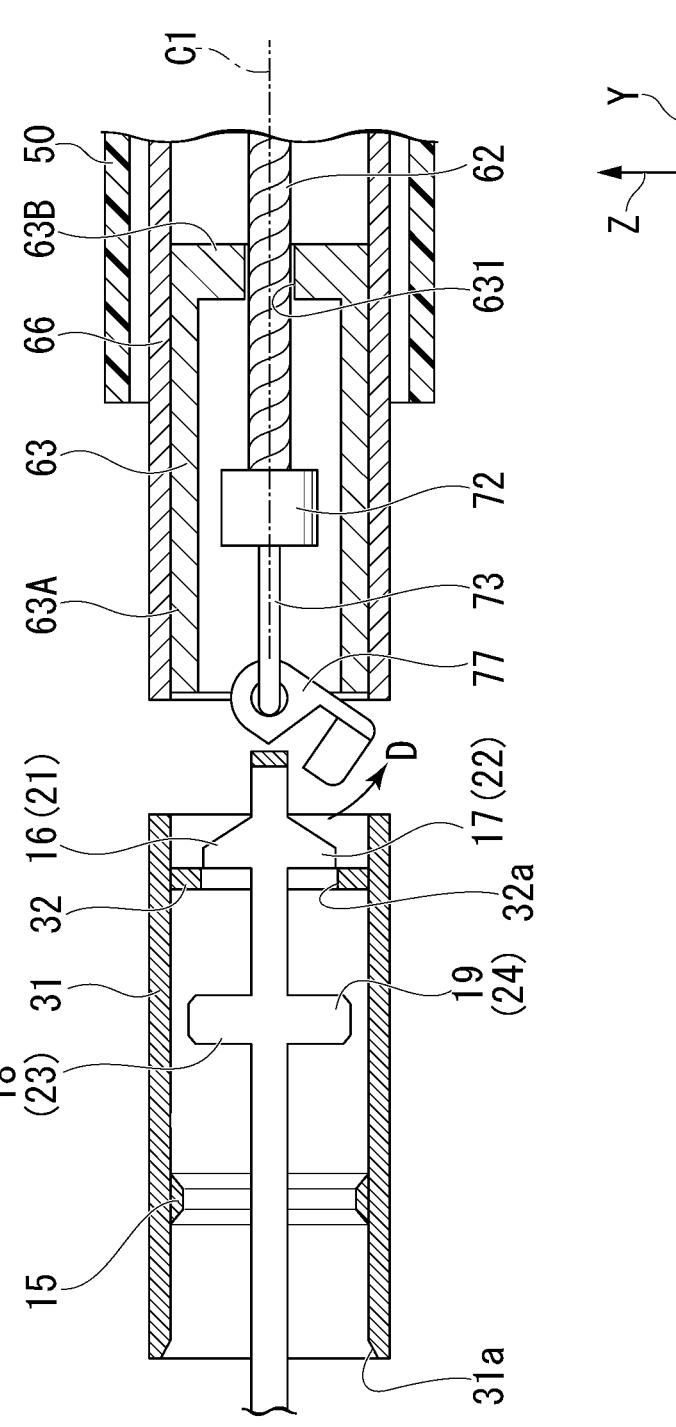
FIG. 7B is a cross-sectional planar view schematically showing the distal end portion of the endoscope clip according to the present embodiment shown in FIG. 7A.
Figure 7B:
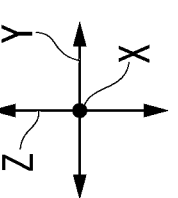
Figure 7C:
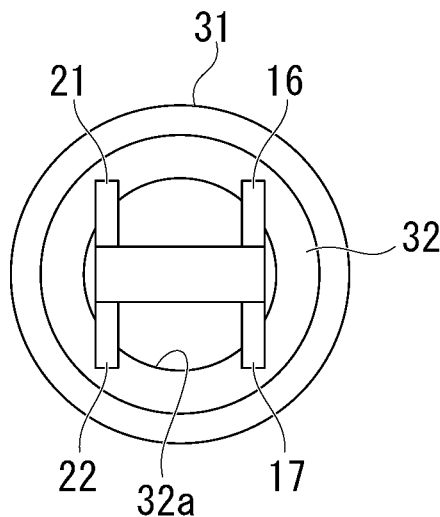
FIG. 7C is a view showing the proximal end portion viewed from the proximal end side of the endoscope clip according to the present embodiment shown in FIG. 7A.

An edge portion 32a of the locking portion 32 at the axis C1 side is formed in a circular shape coaxial with the pressing tube 31 (see FIG. 7C). A portion of the first arm 12 at the proximal end side more than the protrusions 18, 19, a portion of the second arm 13 at the proximal end side more than the protrusions 23, 24, and the central portion 14 are capable of being inserted into the locking portion 32. Although details will be described later, the first locked portions 16, 17 formed on the first arm 12 and the second locked portions 21, 22 formed on the second arm 13 may be locked by with the locking portion 32 by climbing up and overcoming the locking portion 32 to be in contact to the locking portion 32 at the proximal end side of the locking portion 32. According to the present embodiment, the first locked portions 16, 17 and the second locked portions 21, 22 are locked by the locking portion 32 so as to restrict the movement of the arm member 11 toward the distal end side with respect to the pressing tube 31.

As shown in FIG. 1, a tapered surface 31a is formed on the inner circumferential surface of the distal end portion of the pressing tube 31 over the whole circumference. The tapered surface 31a has a diameter that increases toward the distal end side.

These members including the arm member 11 that configure the clip 10 are made of a material such as a cobalt chrome alloy, titanium, or stainless steel. The clip 10 may also be configured to be observable under MRI (Nuclear Magnetic Resonance Imaging) fluoroscopy.

For example, the arm member 11 is formed by punching a plate material formed of a cobalt chrome alloy into a shape as expanding the first arm 12, the second arm 13, the central portion 14, the first locked portions 16, 17, the second engaged portion 21, 22 and the protrusions 18, 19, 23, 24 into a flat shape. The arm member 11 is integrally formed by being bent at a connecting portion between the first arm 12 and the central portion 14, and a connecting portion between the second arm 13 and the central portion 14 to form a C-shape in a side view.

The first arm 12 and the second arm 13 of the arm member 11 have an elastic restoring force applied in a direction in which distal ends thereof are separated from each other, that is, a direction in which the arm member 11 opens. For example, the pressing tube 31 is formed of a material such as 64 titanium alloy (Ti-6AL-4V) or cobalt chromium alloy. (Configuration of Treatment Tool Body 40)

Next, the configuration of the treatment tool main body (applicator) 40 will be described.

As shown in FIG. 1, the treatment tool main body 40 includes an outer sheath 50, an insertion portion 60, and an operation portion (operator) 100. The insertion portion 60 is advanceable and retractable in the outer sheath 50. The operation portion 100 is attached to the proximal end of the insertion unit 60.

For example, the outer sheath 50 may be formed of a fluororesin such as PTFE (polytetrafluoroethylene) or a resin material such as HDPE (high density polyethylene).

The insertion portion 60 of the treatment tool main body 40 includes a sheath 61, an operation wire (wire) 62, and a connection member 63. The operation wire 62 is inserted into the sheath 61 to be advanceable and retractable. The connection member 63 is provided to connect the pressing tube 31 and the coil sheath 66 of the sheath 61.

According to the present embodiment, the sheath 61 is formed by the coil sheath 66. The coil sheath 66 is formed of stainless steel such as SUS301 or the like having high compression strength. More specifically, a coil formed by closely winding strands in the axial direction Y may be used as the coil sheath. The coil sheath 66 has flexibility and is strong against a compressive force in the axial direction Y.

The operation wire 62 is made of, for example, a metal single wire or a twisted wire. The distal end of the operation wire 62 is connected to the proximal end of the enlarged diameter portion 72. A loop portion 73 and a hook 77 are connected to the distal end portion of the enlarged diameter portion 72. That is, according to the present embodiment, the operation wire 62, the enlarged diameter portion 72, the loop portion 73, and the hook 77 are integrally configured and may be advanced and retracted together. Accordingly, according to the present embodiment, the enlarged diameter portion 72, the loop portion 73, and the hook 77 will be described as an extension of the operation wire 62 and as a part of the operation wire 62.

The enlarged diameter portion 72 is formed of, for example, the metal material or the like in a cylindrical shape. The outer diameter of the enlarged diameter portion 72 is smaller than the inner diameters of the coil sheath 66 and the connection member 63 described below. The outer diameter of the enlarged diameter portion 72 is larger than the inner diameter of the through hole 631 formed in the proximal end portion 63B of the connection member 63 described below. That is, the enlarged diameter portion 72 is impossible to pass through the through hole 631 formed in the proximal end portion 63B of the connection member 63.

The loop portion 73 is formed by folding back one wire 73a. The wire 73a has a folded-back portion located at the distal end side, and two ends at the proximal end side are fixed to the enlarged diameter portion 72 by brazing, resistance welding or the like.

The hook 77 is connected to the distal end side of the loop portion 73. According to the present embodiment, the hook 77 may connect the clip 10 and the treatment tool main body 40 by engaging with the central portion 14 of the arm member 11. When the hook 77 is rotated in the direction D with respect to the loop portion 73, the engagement between the hook 77 and the central portion 14 is released (see FIG. 7B). That is, the operation wire 62 is detachably connected to the arm member 11.

As shown in FIGS. 1 and 3, the connection member 63 is a member formed in a cylindrical shape and having an outer diameter substantially equal to the inner diameter of the pressing tube 31 and the inner diameter of the coil sheath 66. The connection member 63 has a lumen formed in the distal end portion 63A with an inner diameter suitable for the large diameter portion 72, the loop portion 73, the hook 77, and the first arm 12 and the second arm 13 of the arm member 11 to enter. On the other hand, the inner diameter of the connection member 63 is reduced at a part of the proximal end portion 63B. More specifically, in the connection member 63, a through hole 631 with an inner diameter smaller than the outer diameter of the large diameter portion 72 and equal to or larger than the inner diameter of the outer diameter of the operation wire 62 is formed at the proximal end portion 63B.

According to the present embodiment, the material forming the connection member 63 is not particularly limited, for example, a material that is elastically deformable may be used. The connection member 63 is configured in this manner such that the distal end portion 63A may be press-fitted from the proximal end side of the pressing tube 31, and the proximal end portion 63B may be press-fitted from the distal end side of the coil sheath 66. According to the present embodiment, the distal end portion 63A of the connection member 63 is press-fitted into the pressing tube 31 and is into close contact with the inner circumferential surface of the pressing tube 31 located at the proximal end side more than the locking portion 32 such that a friction force is generated between the connection member 61 and the pressing tube 31. Similarly, the proximal end portion 63B of the connection member 63 is press-fitted into the distal end portion of the coil sheath 66 and is into close contact with each other such that a friction force is generated between the connection member 63 and the coil sheath 66. The friction force (static friction force) between the connection member 63 and the pressing tube 31 or the coil sheath 66 is determined by a static friction coefficient due to the material forming the connection member 63, the pressing tube 31, and the coil sheath 66, and a degree of close contact (that is, the magnitude of the pressing force) between the connection member 63 and the pressing tube 31 or the coil sheath 66.

According to the present embodiment, the friction force between the connection member 63 and the pressing tube 31 and the friction force between the connection member 63 and the coil sheath 66 are applied such that the pressing tube 31 and the coil sheath 66 are connected by the connection member 63. In the natural state in which no external force applies, there is no case in which the connected state between the pressing tube 31 and the coil sheath 66 is released. That is, in the endoscope clip 1 according to the present embodiment, the pressing tube 31 and the sheath 66 are connected by the connection member 63 to configure an integrated configuration. The pressing tube 31A and the sheath 66 are fixed by the connection member 63 in the direction of the axis C1 of the pressing tube 31A. Accordingly, when the operator pushes the slider 102 toward the distal end side to move the operation wire 62 toward the distal end side, the pressing tube does not move toward the distal end side.

As described below, from the time when the operation wire 62 and the enlarged diameter portion 72 connected to the distal end side of the operation wire 62 are pulled back to the proximal end side and the proximal end surface of the enlarged diameter portion 72 comes in contact to the proximal end portion 63B of the connection member 63, when the force for further pulling back the operation wire 62 is slightly larger than the maximum static friction force between the connection member 63 and the pressing tube 31 or the coil sheath 66, the connection member 63 may be pulled back to the proximal end side. In this state, the connection member 63 may be moved toward the proximal end side with respect to the pressing tube 31 and the coil sheath 66.

A lumen having an inner diameter larger than the outer diameter of the large diameter portion 72, the outer diameter of the loop portion 73, and the outer diameter of the hook 77 is formed at the distal end portion 63A of the connection member 63. The outer diameter of the large diameter portion 72, the outer diameter of the loop portion 73, and the outer diameter of the hook 77 refer to the outer diameters in the radial direction orthogonal to the central axis C1 in these configurations. According to the present embodiment, the hook 77 is not rotatable with respect to the loop portion 73 in the pressing tube 31 and the connection member 63 from a state in which the hook 77 is at the distal end side. In other words, the relative movement in the radial direction of the arm member 11 and the hook 77 is restricted by the pressing tube 31 and the distal end portion 63A of the connection member 63.

The above-mentioned recitation "the hook 77 is not rotatable with respect to the loop portion 73" means that the hook 77 is not rotatable with respect to the loop portion 73 until the engagement between the hook 77 and the central portion 14 is released. Accordingly, "the hook 77 is not rotatable with respect to the loop portion 73" does not literally mean that the hook 77 is totally not rotatable with respect to the loop portion 73.

As shown in FIG. 1, the operation portion 100 has an operation portion main body (handle) 101, a slider 102, and a limiting portion 64.

The operation portion main body 101 is attached to the proximal end portion of the coil sheath 66. The operation portion main body 101 is formed in a rod shape extending in the axial direction Y, and has a finger hook portion 101a at the proximal end portion. A slit 101b extending in the axial direction Y is formed in the operation portion main body 101.

The slider 102 is provided to be inserted into the operation portion main body 101. The slider 102 is slidable (advance and retract) in the axial direction Y with respect to the operation portion main body 101. The proximal end of the operation wire 62 is connected to the distal end portion of the slider 102. In the clip 10 according to the present embodiment, the operation wire 62 is advanced or retracted by operating the slider 102 to advance or retract in the axial direction Y. The enlarged diameter portion 72, the loop portion 73, the hook 77, and the arm member 11 of the clip 10 disposed on the distal end side of the operation wire 62 may be advanceable or retractable. As a result, the pair of first arm 12 and second arm 13 of the arm member 11 may be opened or closed.

The slider 102 is formed in a cylindrical shape. On the outer circumferential surface of the slider 102, a recess portion 102a is formed over the entire circumference. In the slider 102, a flange portion 102b, the recess portion 102a, and a flange portion 102c are formed in this sequence from the distal end side toward the proximal end side in the axial direction Y. The pair of flange portions 102b and 102c are formed in an elliptical shape when viewed in the axial direction Y. As a result, the slider 102 is easy to be grasped, and space may be saved when the operation portion 100 of the endoscope clip 1 is packaged.

The movement range of the slider 102 with respect to the operation portion main body 101 in the axial direction Y is restricted by the slider 102 engaging with the slit 101b of the operation portion main body 101.

As shown in FIGS. 1 and 2, the limiting portion 64 is a hollow tubular member formed to extend along the axial direction Y of the slider 102. The limiting portion limiting portion 64 has an inner cavity 641 through which the operation wire 62 is insertable. The limiting portion 64 may be made of, for example, a resin material. The limiting portion 64 has a rigidity such that the limiting portion 64 is not compressed even if a predetermined pressure in the longitudinal axis direction is applied thereto. The dimension of the limiting portion 64 in the longitudinal axis direction is not particularly limited. For example, the dimension of the limiting portion 64 in the longitudinal axis direction only has to be equal to or smaller than the value achieved by subtracting the dimension of the slider 102 in the longitudinal axis from the dimension of the slit 101b of the operation portion main body 101 in the longitudinal axis direction.

However, as described later, since there is a correlation between the dimension of the limiting portion 64 in the longitudinal axis direction and the opening width of the arm member 11, it is preferable to determine the dimension of the limiting portion 64 in the longitudinal axis by taking the desired opening width of the arm member 11 into consideration.

As shown in FIG. 2, in a cross-sectional view of the slider 102 along the axial direction Y, a shape of the cross section of the limiting portion 64 according to the present embodiment is a substantially C-shape. The limiting portion 64 has a slit portion 642 that connects the inner cavity 641 and the outside. The slit portion 642 is an elongated notch formed to extend along the axial direction Y of the slider 102. The slit portion 642 has an opening width slightly smaller than the diameter of the operation wire 62. The slit portion 642 is deformable such that when the operator removes the limiting portion 64, the slit portion 642 is deformed to form a gap having a size suitable for the operation wire 62 to pass through.

According to the present embodiment, as shown in FIG. 1, the limiting portion 64 is disposed in the slit 101b of the operation portion main body 101 while covering the operation wire 62. The limiting portion 64 is disposed at the distal end side more than the slider 102 in the slit 101b. At this time, the movable range of the slider 102 refers to a range by subtracting the dimension of the limiting portion 64 in the longitudinal axis direction from the length of the slit 101b of the operation portion main body 101 from the proximal end of the slit 101b toward the distal end side. In other words, the limiting portion 64 according to the present embodiment is a member configured to limit the pushing amount of the operation wire 62.

Figure 8A:
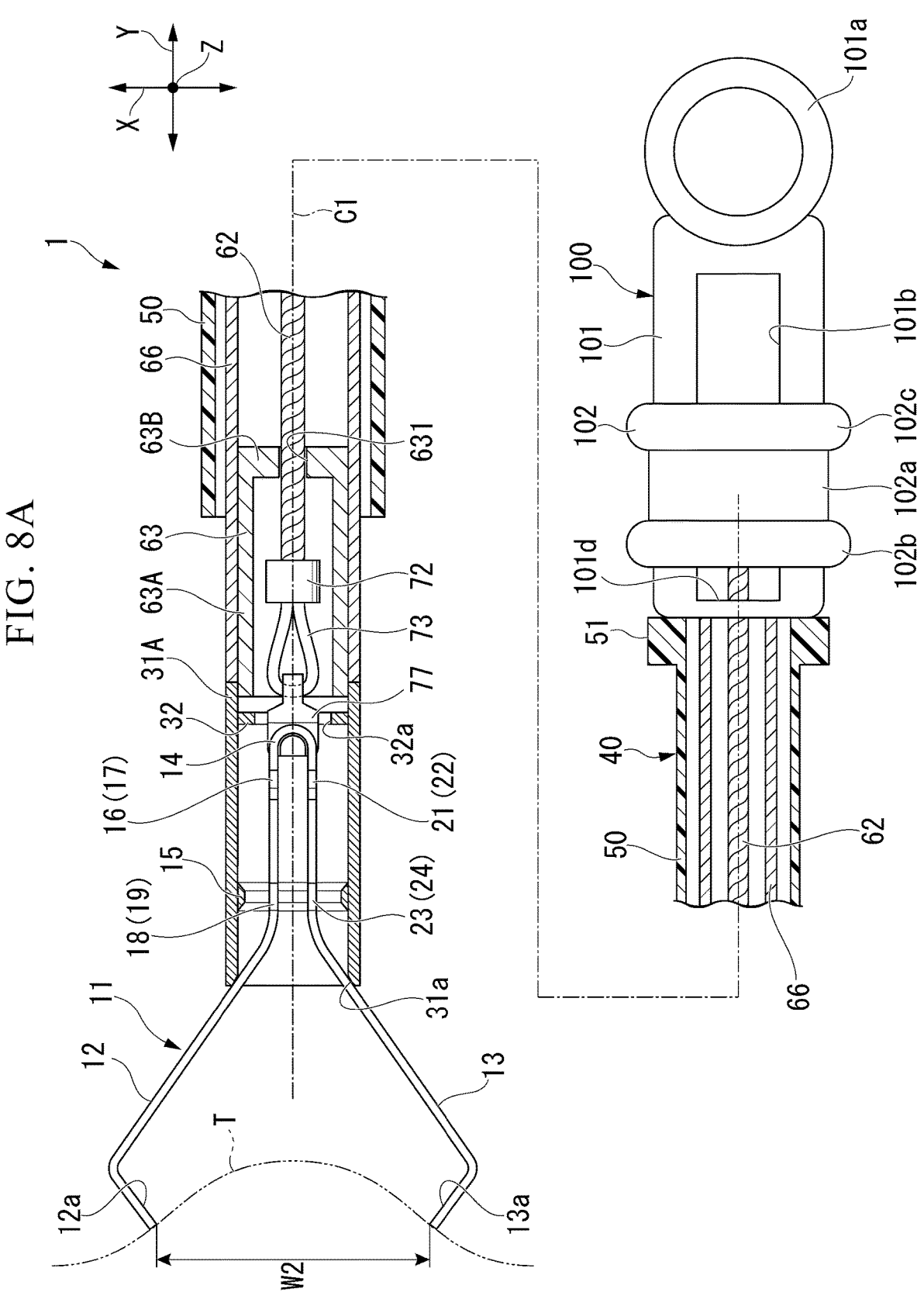
FIG. 8A is a cross-sectional view schematically showing the endoscope clip according to the present embodiment.
Figure 8B:
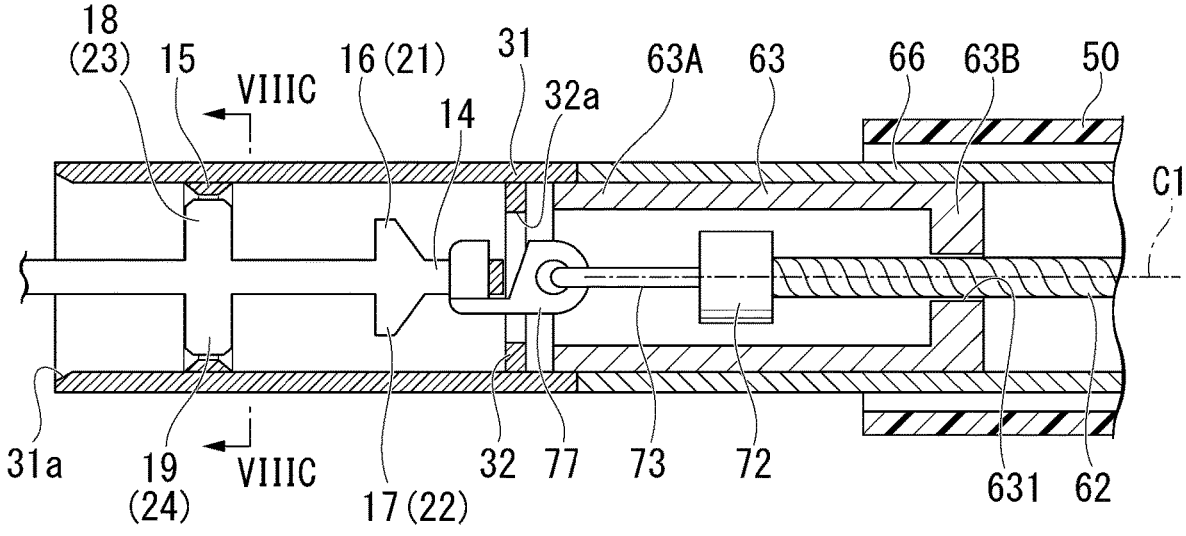
FIG. 8B is a cross-sectional planar view showing the distal end portion of the endoscope clip according to the present embodiment shown in FIG. 8A.

On the other hand, as shown in FIGS. 8A and 8B, when the limiting portion 64 is removed, the movable range of the slider 102 is within the range of the whole length of the slit 101*b* of the operation portion main body 101 in the longitudinal axis direction.

According to the present embodiment, the dimension of the limiting portion 64 in the longitudinal direction may be set corresponding to the position of the step portion 15 in the pressing tube 31. Specifically, for example, as shown in FIG. 4A, when the slider 102 is moved to the distal end side and comes into contact with the limiting portion 64, each of the protrusions 18, 19, 23, 24 engages with the step portion 15 in the pressing tube 31. In this state, the elastic restoring force of the first arm 12 and the second arm 13 is applied to the arm member 11 to bias the arm member 11 toward the distal end side. On the other hand, the engaging force generated by the engagement of each of the protrusions 18, 19, 23, 24 and the step portion 15 is applied to the arm member 11 to restrict the movement of the arm member 11 toward the distal end side. The engagement force generated by the engagement between the limiting portion 64 and the slider 102 is applied to the slider 102 to restrict the movement of the operation wire 62 and the arm member 11 connected to the slider 102 toward the distal end side. In the state shown in FIG. 4A, these forces are in balance. Accordingly, the arm member 11 is stationary in a state in which each of the protrusions 18, 19, 23, 24 and the step portion 15 press each other. In the natural state in which no external force applies, the protrusions 18, 19, 23, 24 do not toward the distal end side to climb on and overcome the step portion 15.

(Initial State of Endoscope Clip 1)

Next, a medical procedure for ligating the target tissue T in a normal size using the endoscope clip 1 having the above-described configuration will be described. That is, an example in which the size of the target tissue T is equal to or smaller than the maximum opening width of the half-opened arm member 11 will be described.

In the initial state before the procedure is started, when the endoscope clip 1 is provided to the operator as a surgery, as shown in FIG. 1, the clip 10 is in the state of being attached to the treatment tool main body 40 and covered by the outer sheath 50.

As shown in FIG. 1, in the initial state, the protrusions 18, 19, 23, 24 and the step portion 15 are in contact with each other and pressed against each other. The first locked portions 16, 17 of the first arm 12 and the second locked portions 21, 22 of the second arm 13 are positioned at the distal end side more than the locking portion 32 of the pressing tube 31. The pressing tube 31 and the coil sheath 66 are connected by the connection member 63.

On the other hand, since the distal end surface of the slider 102 in the operation portion 100 at the proximal end side is in contact with the proximal end surface of the limiting portion 64, the movable range of the slider 102 toward the distal end side is restricted by the limiting portion 64. The enlarged diameter portion 72 is located in the connection member 63 at a position separated from the through hole 631 formed in the proximal end portion 63B. The loop portion 73 and the hook 77 are disposed in the pressing tube 31, the hook 77 is not rotatable with respect to the loop portion 73, and the engagement between the hook 77 and the central portion 14 is maintained.

In the initial state, as shown in FIG. 1, a part from the distal end to the proximal end of each of the first arm 12 and the second arm 13 of the arm member 11 is in contact with the inner circumferential surface of the outer sheath 50. The distal end portion (claw 12*a*) of the first arm 12 and the distal end portion (claw 13*a*) of the second arm 13 of the arm member 11 are in contact with each other. According to the present invention, the closed configuration of the arm member 11 is defined as the state in which the first arm 12 and the second arm 13 are in contact with each other, or the distance between the distal end of the first arm 12 and the distal end of the second arm 13 is substantially zero. The state in which the distance between the distal end of the first arm 12 and the distal end of the second arm 13 is substantially zero refers to a state in which the claw 12*a* of the first arm 12 and the claw 13*a* of the second arm 13 are separated from each other and not directed toward the front side.

In the initial state, the slider 102 is in contact with the limiting portion 64 in the slit 101*b* of the operation portion main body 101. The limiting portion 64 is in contact with the distal end surface 101*d* of the slit 101*b* of the operation portion main body 101.

At this time, the orientation or posture of the clip 10 may be adjusted by rotating the operation wire 62 with respect to the sheath 61 so as to rotate the arm member 11 with respect to the pressing tube 31 around the axis C1.

When using the endoscope clip 1, the operator inserts an endoscope (not shown) into the body of the patient. Subsequently, the operator inserts the outer sheath 50 of the endoscope clip 1 from the proximal end portion of the channel of the endoscope, and protrudes the outer sheath 50 from the distal end portion of the channel of the endoscope.

Next, as shown in FIG. 4A, the operator operates the outer tube operating portion 51 of the operation portion main body 101 to pull back the outer sheath 50 with respect to the insertion portion 60 of the treatment tool main body 40 so as to release the state in which the first arm 12 and the second arm 13 of the clip 10 are in contact with the inner circumferential surface of the outer sheath 50.

As described above, the arm member 11 of the clip 10 according to the present embodiment has an elastic restoring force in the direction in which the distal ends of the first arm 12 and the second arm 13 move to be separated from each other. Accordingly, the opening width increases while the first arm 12 and the second arm 13 are in contact with the tapered surface 31*a* provided on the inner circumferential surface of the distal end portion of the pressing tube 31 and the first arm 12 and the second arm 13 enter the open state. As a result, due to the elastic restoring force of the first arm 12 and the second arm 13, the arm member 11 is biased toward the direction (first direction) in which the arm member 11 protrudes from the pressing tube 31. That is, the elastic restoring force of the first arm 12 and the second arm 13 functions to move the arm member 11 toward the distal end side.

In this state, as shown in FIG. 4A, the first arm 12 and the second arm 13 are in contact with the tapered surface 31*a* of the distal end portion of the pressing tube 31. As described below, a first distance W1 as the opening width between the first arm 12 and the second arm 13 is restricted by the tapered surface 31*a* of the distal end portion of the pressing tube 31 and the first distance W1 is smaller than a second distance W2 as the maximum opening width.

When the distal end surface of the slider 102 comes in contact with the proximal end surface of the limiting portion 64, the slider 102 is impossible to further move with respect to the operation portion main body 101 due to the limiting portion 64. As shown in FIG. 4A, the position where the slider 102 is in contact with the limiting portion 64 and is advanced to the most distal end side with respect to the operation portion main body 101 is defined as a neutral position (neutral position). When the slider 102 is at the neutral position, as shown in FIG. 4A, the limiting portion 64 is sandwiched between the distal end surface of the slider 102 and the distal end surface 101d of the slit 101b of the operation portion main body 101.

When the slider 102 is at the neutral position, both the operation wire 62 connected to the slider 102 and the arm member 11 connected to the operation wire 62 are in a state in which they are not advanceable with respect to the operation portion main body 101. Accordingly, as shown in FIG. 4A, the first arm 12 and the second arm 13 of the arm member 11 are in the first open configuration as a so-called half-opened state rather than a completely opened state. However, according to the present embodiment, the first open configuration of the arm member 11 is not limited thereto. According to the present embodiment, the first open configuration of the arm member 11 may be freely set according to the size of the target tissue T as long as the opening width between the first arm 12 and the second arm 13 is equal to or smaller than the possible maximum opening width.

As shown in FIG. 4B, when the arm member 11 is in the first open configuration, in the pressing tube 31, a state in which the first locked portions 16, 17 and the second locked portions 21, 22 are separated from the locking portion 32 and positioned at the distal end side more than the locking portion 32, while the protrusions 18, 19, 23, 24 and the step portion 15 come in contact and press each other is maintained. In other words, in this state, in the arm member 11, the protrusions 18, 19, 23, 24 do not climb on and overcome the step portion 15 to move to the distal end side. The enlarged diameter portion 72 is apart from the through hole 631 formed in the proximal end portion 63B of the connection member 63 to be located at the distal end side.

In the first open configuration of the arm member 11, the maximum opening width of the half-opened arm member 11 is defined as the first distance W1 between the first arm 12 and the second arm 13. According to the present embodiment, in order to reliably grasp the target tissue T, the first distance W1 only has to be equal to or larger than the size of the target tissue T. However, taking the efficiency when the operator operates the endoscope clip 1 into consideration, the first distance W1 may be substantially equal to the size of the target tissue T.

As shown in FIG. 4A, the operator can position the target tissue T between the first arm 12 and the second arm 13 in the half-opened state. When the operator confirms that the target tissue T is located between the first arm 12 and the second arm 13, the operator may operate the endoscope to push the arm member 11 toward the target tissue T so as to grasp the target tissue T.

Figure 4C:
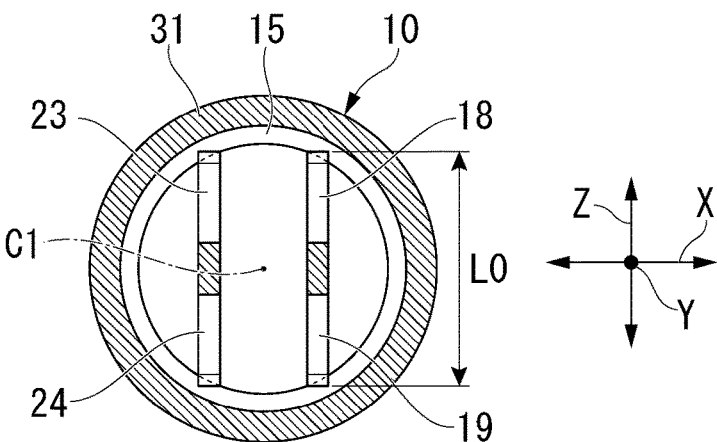
FIG. 4C is a cross-sectional view showing a pressing tube broken along a cutting line IVC-IVC and viewed from the proximal end of the endoscope clip shown in FIG. 4B.

FIG. 4C is a cross-sectional view of the clip 10 broken along IVC-IVC in FIG. 4B when viewed from the proximal end side along the axial direction Y. As shown in FIG. 4C, the edge portion of the step portion 15 on the axis C1 side is formed in a circular shape coaxial with the pressing tube 31. As shown in FIG. 4C, a length L0 from the end of the protrusion 18 to the end of the protrusion 19 (the length from the end of the protrusion 23 to the end of the protrusion 24) is smaller than the inner diameter of the step portion 15. When viewed in the axial direction Y, part of each of the protrusions 18, 19, 23, 24 overlaps the step portion 15. That is, in the state shown in FIG. 4C, each of the protrusions 18, 19, 23, 24 is in contact with the edge portion of the step portion 15.

(Contact State of Endoscope Clip 1)

Figure 5A:
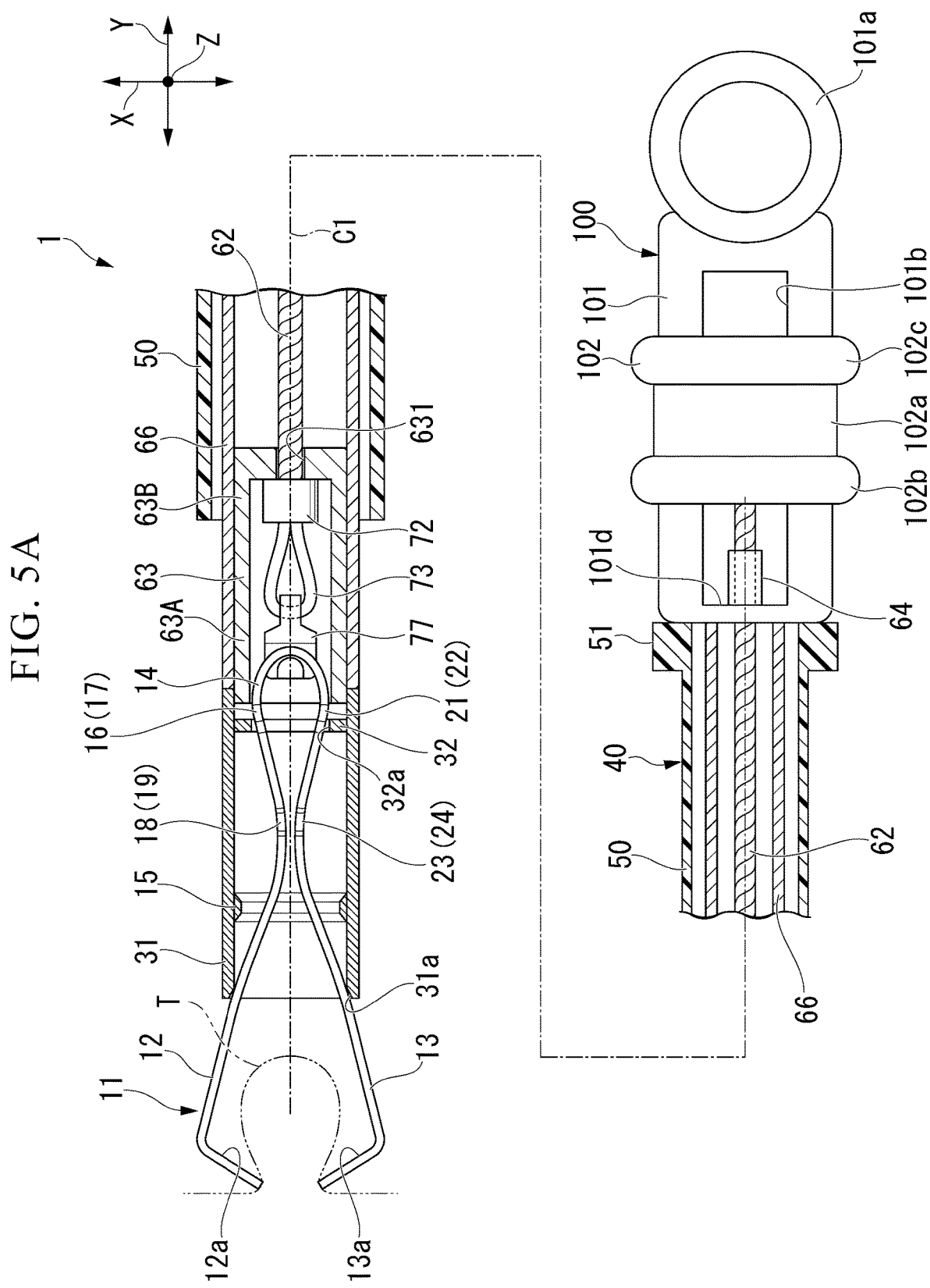
FIG. 5A is a cross-sectional side view schematically view showing the endoscope clip according to the present embodiment.

When the operator confirms that the target tissue T is located between the first arm 12 and the second arm 13, the operator may grasp the operation portion main body 101 and pull back the slider 102 to grasp the target tissue T. At this time, as shown in FIG. 5A, the slider 102 does not come into contact with the limiting portion 64 and retreats toward the proximal end side along the slit 101b of the operation portion main body 101. At this time, the first arm 12 and the second arm 13 of the arm member 11 move to the proximal end side while contacting the tapered surface 31a of the distal end portion of the pressing tube 31. In such a state, the first arm 12 is elastically deformed toward the second arm 13 side, and the second arm 13 is elastically deformed toward the first arm 12 side. As a result, the distal end of the first arm 12 and the distal end of the second arm 13 approach each other, and the opening width of the arm member 11 is reduced. That is, with the target tissue T positioned between the first arm 12 and the second arm 13, the arm member 11 is transitioned from the first open configuration to the closed configuration. At this time, the target tissue T is grasped by the first arm 12 and the second arm 13. According to the present embodiment, the state in which the target tissue is tightly bound by the first arm 12 and the second arm 13 at the root thereof and the distance between the first arm 12 and the second arm 13 is substantially zero is included in the closed configuration of the arm member 11.

On the other hand, when the operator pulls back the slider 102, the first locked portions 16, 17 of the first arm 12 and the second locked portions 21, 22 of the second arm 13 move toward the proximal end side to approach the locking portion 32 of the pressing tube 31.

Figure 5B:
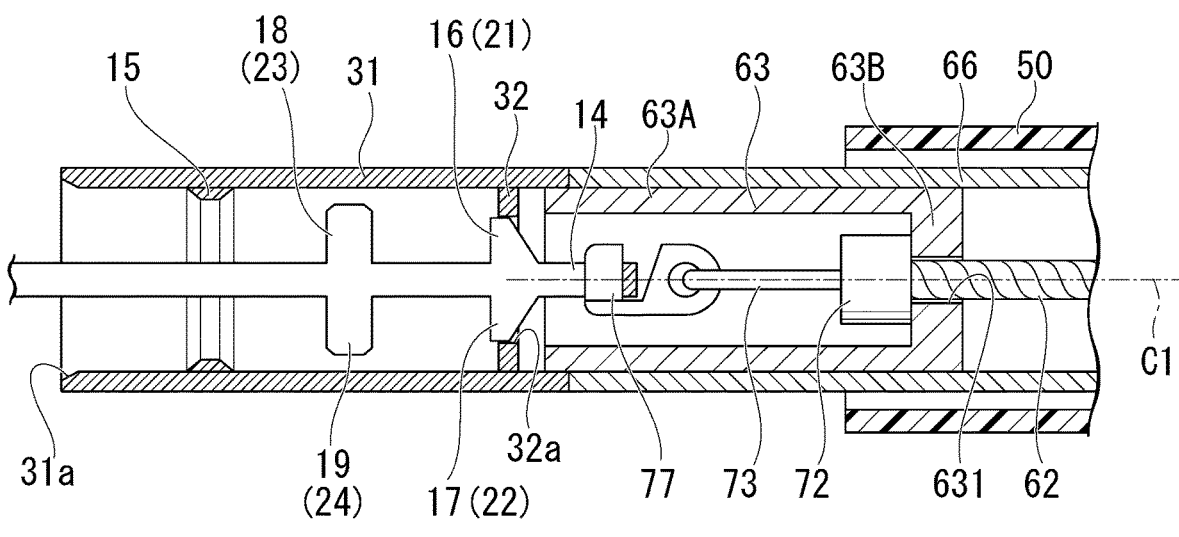
FIG. 5B is a cross-sectional planar view showing a distal end portion of the endoscope clip according to the present embodiment shown in FIG. 5A.
Figure 5B:
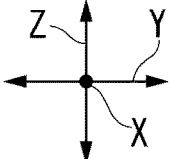

In this state, as shown in FIG. 5B, the protrusions 18, 19, 23, 24 of the arm member 11 are not in contact to the step portion 15, and are located at the proximal end side more than the step portion 15. The first locked portions 16, 17 and the second locked portions 21, 22 are moved to a position to come in contact with and partially enter the edge portion 32a of the locking portion 32. The enlarged diameter portion 72 is pulled back toward the proximal end side to a position to come in contact with (contacts) the proximal end portion 63B of the connection member 63. However, in the state shown in FIG. 5B, the connection member 63 does not move to the proximal end side with respect to the pressing tube 31 by the enlarged diameter portion 72 pressing the proximal end portion 63B of the connection member 63.

(Locking State of Endoscope Clip 1)

As shown in FIGS. 5A and 5B, when the operator further pulls back the slider 102 to the proximal end side from the state in which the enlarged diameter portion 72 is in contact with the proximal end portion 63B of the connection member 63, the force for pulling back the operation wire 62 and the enlarged diameter portion 72 connected to the operation wire 62 is applied to the proximal end portion 63B of the connection portion 63. At this time, the force for pulling back the connection member 63 toward the proximal end side in the connection member 63 and the friction force generated between the connection member 63 and the pressing tube 31 or the coil sheath 66 are in balance, such that the connection member 63 is stationary with respect to the pressing tube 31.

The friction force generated between the connection member 63 and the pressing tube 31 or the coil sheath 66 increases as the force for pulling back the slider 102 increases. Accordingly, the operator may feel that the force for pulling back the slider 102 also increases, that is, the operator may feel the operation to pull back the slider 102 become heavy. The operator may recognize the state in which the enlarged diameter portion 72 is in contact with the proximal end portion 63B of the connection member 63.

In this state, the first locked portions 16, 17 and the second locked portions 21, 22 partially enter and engage with the locking portion 32 in the pressing tube 31. Accordingly, even if the force for pulling back the slider 102 by the operator is canceled, the movement of the arm member 11 toward the distal end side with respect to the pressing tube 31 is restricted due to the engagement between the first locked portions 16, 17, the second locked portions 21, 22 and the locking portion 32. As a result, in the arm member 11, the distance between the first arm 12 and the second arm 13 increases, and the transition to the first open configuration is restricted. In other words, the state in which the target tissue T is grasped by the first arm 12 and the second arm 13 of the arm member 11 is maintained.

In the state shown in FIGS. 5A and 5B, the operator may move the operation wire 62 and the arm member 11 connected to the operation wire 62 to the distal end side by pushing the slider 102 toward the distal end side again. At this time, the first locked portions 16, 17 and the second locked portions 21, 22 move to the distal end side while contacting the locking portion 32. When the operator pushes the slider 102 until the slider 102 abuts against the limiting portion 64, the engagement between the first locked portions 16, 17, the second locked portions 21, 22 and the locking portion 32 is released, and the first arm 12 and the second arm 13 of the arm member 11 may be transitioned to the first open configuration again.

Accordingly, in the process in which the slider 102 is pulled back until the contact state of the endoscope clip 1 described above, the operator may operate the endoscope to direct the clip 10 toward the target tissue T and grasp the target tissue T again. During the process of grasping the target tissue T again, in order to cause the first locked portions 16, 17 and the second locked portions 21, 22 to be smoothly moved to the distal end side in a state of coming in contact with the locking portion 32, for example, it is preferable to perform chamfering process to the portion of the first locked portions 16, 17 and the second locked portions 21, 22 contacting the locking portion 32.

The operator may pull back the slider 102 to the proximal end side after confirming that the target tissue T is grasped by the first arm 12 and the second arm 13 of the arm member 11 in a desired state. By this operation, the arm member 11 is pulled back to the proximal end side together with the operation wire 62 while the target tissue T is grasped by first arm 12 and the second arm 13. When the force by the operator to pull back the slider 102 continues increasing, both the force applied to the connection member 63 by the enlarged diameter portion 72 and the friction force between the connection member 63 and the pressing tube 31 or the coil sheath 66 increase for a while. When the force by the operator to pull back the slider 102 to the proximal end side becomes larger than the maximum static friction force between the connection member 63 and the pressing tube 31 or the coil sheath 66, the connection member 63 may be moved toward the proximal end side with respect to the pressing tube 31 and the coil sheath 66 while being in contact with the pressing tube 31 and the coil sheath 66 by the operation of the operator to pull back the slider 102. In other words, the operator may pull back the connection member 63 to the proximal end side while maintaining the connection state of the pressing tube 31 and the coil sheath 66 by the connection member 63. At this time, the force by the operator to pull back the slider 102 to the proximal end side may be, for example, equal to or more than a dynamic friction force between the connection member 63 and the pressing tube 31 or the coil sheath 66.

In the process in which the operator pulls back the slider 102 to the proximal end side, the operation wire 62 and the arm member 11 are also moved to the proximal end side, and state in which the target tissue T is grasped by the first arm 12 and the second arm 13 of the arm member 11 is maintained. The loop portion 73 and the hook 77 are located inside the connection member 63, the hook 77 is not rotatable with respect to the loop portion 73, and the engagement state between the hook 77 and the central portion 14 of the arm member 11 is maintained. The first locked portions 16, 17 and the second locked portions 21, 22 are moved toward the proximal end side with respect to the pressing tube 31 while being in contact with the edge portion 32a of the locking portion 32 of the pressing tube 31.

Figure 6A:
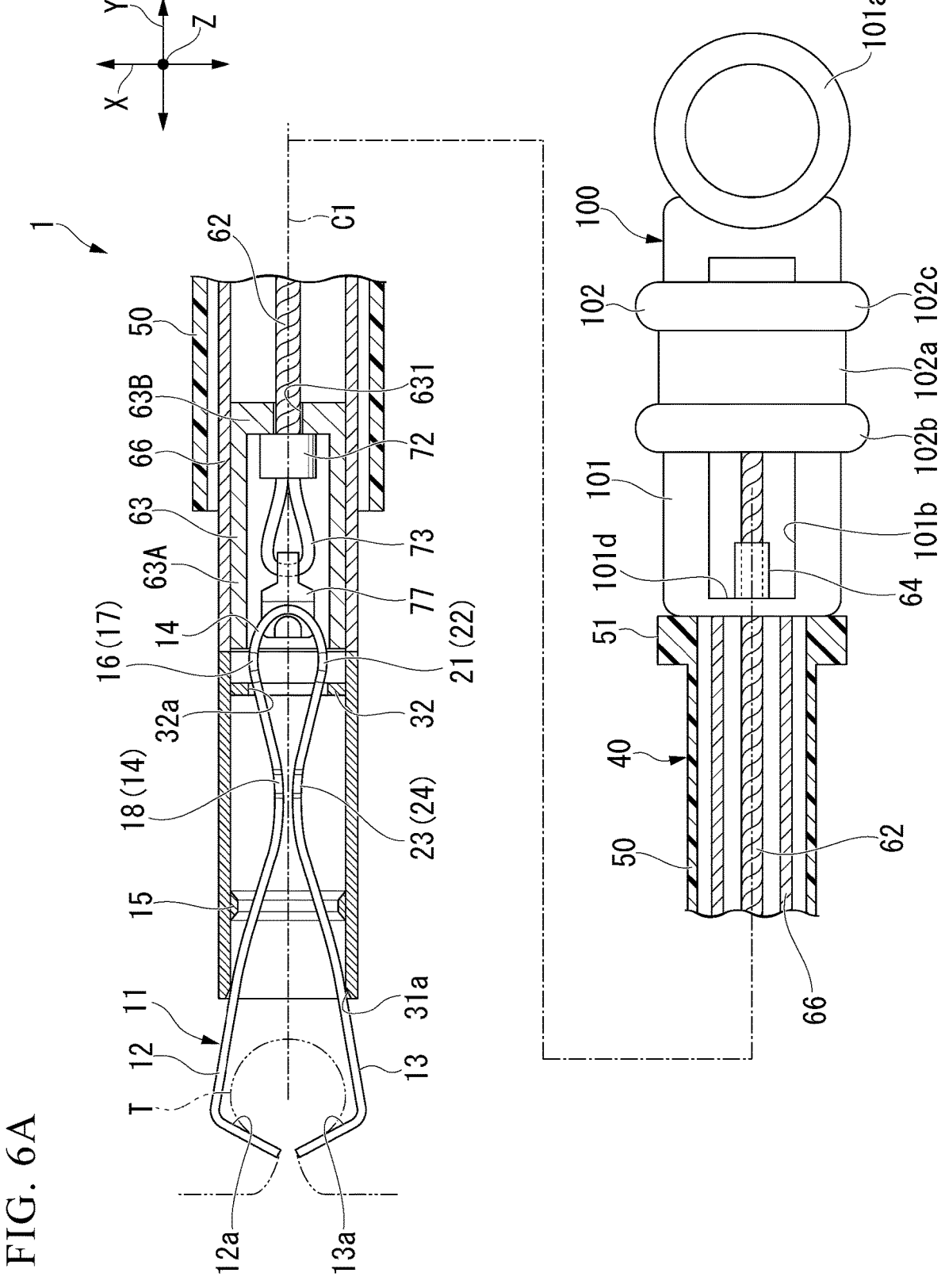
FIG. 6A is a cross-sectional side view schematically showing the endoscope clip according to the present embodiment.

As shown in FIG. 6A, when the operator continues pulling back the slider 102 toward the proximal end side, the connection member 63 may be moved to a position where a distal end surface thereof is aligned with the distal end surface of the coil sheath 66, or at the proximal end side relative to the distal end surface of the coil sheath 66. At this time, since the connection member 63 has been moved to the proximal end side more than the proximal end of the pressing tube 31, the state of being contact with the inner circumferential surface of the pressing tube 31 is released. When the contact state between the connection member 63 and the pressing tube 31 is released, the connected state between the pressing tube 31 and the coil sheath 66 by the connection member 63 is also released.

Figure 6B:
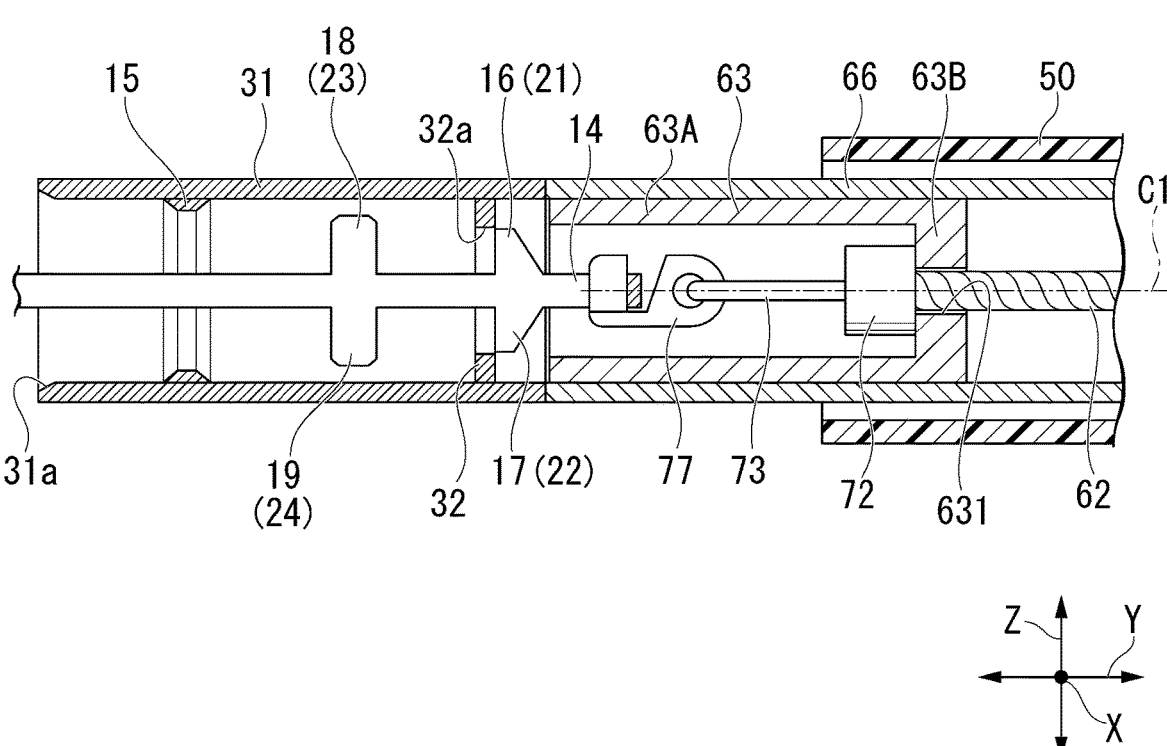
FIG. 6B is a cross-sectional planar view schematically showing the distal end portion of the endoscope clip according to the present embodiment shown in FIG. 6A.

On the other hand, the first locked portions 16, 17 and the second locked portions 21, 22 climbs on and overcomes the locking portion 32 of the pressing tube 31 to be moved to a position at the proximal end side more than the locking portion 32. As shown in FIGS. 6A, 6B, in the first locked portion 16 and the first locked portion 17, each distal end surface of them is in contact with the proximal end surface of the locking portion 32, and locked by the locking portion 32. Similarly, each distal end surface of the second engaged portion 21 and the second engaged portion 22 is in contact with the proximal end surface of the locking portion 32, and locked by the locking portion 32. At this time, the arm member 11 is in a closed configuration in which the distance between the first arm 12 and the second arm 13 is substantially zero. The target tissue T is maintained in the state in which the root thereof is bound by the first arm 12 and the second arm 13 of the arm member 11.

As shown in FIGS. 6A and 6B, when the first locked portions 16, 17 and the second locked portions 21, 22 are engaged to the pressing tube 31, the arm member 11 is not capable of moving toward the distal end side with respect to the pressing tube 31. In this state, the closed configuration in which the distance between the first arm 12 and the second arm 13 of the arm member 11 is substantially zero is maintained. In other words, the target tissue T is grasped by the integrated arm member 11 and the pressing tube 31.

As shown in FIGS. 6A and 6B, since the hook 77 and the loop portion 73 of the treatment tool main body 40 are located inside the connection member 63, the hook 77 is not rotatable with respect to the loop portion 73, and the engagement between the hook 77 and the central portion 14 of the arm member 11 is maintained. The slider 102 is located at a position at the proximal end side more than the limiting portion 64.

(Release State of Endoscope Clip 1)

When the target tissue T shown in FIGS. 6A and 6B is grasped by the endoscope clip 1 (the integrated arm member 11 and pressing tube 31), by the operator pushing the slider 102 toward the distal end side, the operation wire 62 may be moved toward the distal end side while maintaining the engagement state between the hook member 77 and the central portion 14 of the arm member 11. At this time, the arm member 11 and the pressing tube 31 being engaged with each other may move to the distal end side integrally with the operation wire 62. As shown in FIG. 7A, by the operator pushing the slider 102, the loop portion 73 and the hook 77 connected to the operation wire 62 are positioned at the distal end side more than the connection member 63 and the distal opening of and the coil sheath 66. At this time, the enlarged diameter portion 72 connected to the operation wire 62 is located at the distal end side and apart from the proximal end portion 63B of the connection member 63.

As shown in FIG. 7B, when the loop portion 73 connected to the operation wire 62 and the hook 77 protrude from the opening at the distal end side of the coil sheath 66, the hook 77 may rotate in the direction D with respect to the loop portion 73. As shown in FIG. 7B, when the operator further pushes the slider 102 slightly to move the operation wire 62 to the distal end side, the inclined surface of the hook 77 comes in contact with the proximal end surface of the central portion 14 of the clip 10 ligating the target tissue T. Accordingly, the hook 77 is guided by the inclined surface of the hook 77 to rotate in the direction D, and the engagement between the hook 77 and the central portion 14 is released. At this time, as shown in FIG. 7C, the first locked portions 16, 17 of the first arm 12 and the second locked portions 21, 22 of the second arm 13 are engaged with the proximal end surface of the locking portion 32 of the pressing tube 31, and the closed configuration of the arm member 11 of the clip 10 is maintained.

As a result, the clip 10 ligating the target tissue T is indwelled inside the body.

After the clip 10 ligating the target tissue T is indwelled in the body, the operator pulls back the slider 102 to accommodate the hook 77 and the loop portion 73 in the sheath 61. Subsequently, the operator pulls out the endoscope clip 1 from the channel of the endoscope and takes the channel of the endoscope out from the body of the patient. Finally, the operator takes necessary measures and finishes the series of procedures.

(Second Open Configuration of Arm Member 11)

When the arm member 11 is in the first open configuration, the first distance W1 as the maximum opening width between the first arm 12 and the second arm 13 may be smaller than the size of the target tissue T. In this case, it is necessary to increase the opening width of the arm member 11 in order to reliably grasp the target tissue.

According to the present embodiment, the operator may move the slider 102 toward the distal end side after removing the limiting portion 64 from the slit 101$b$ of the operation portion main body 101 so as to further increase the opening width of the arm member 11. By such an operation, the operator may cause the arm member 11 to be transitioned from the half-opened state (first open configuration) to the fully-opened state (second open configuration).

Hereinafter, the operation of the arm member 11 being transitioned from the first open configuration to the second open configuration according to the present embodiment will be described. The operation of the arm member 11 being transitioned from the second open configuration to the closed configuration and the operation of indwelling the clip 10 in the body according to the present embodiment may be performed in the same manner with the above-described operation, and therefore description thereof will be omitted.

As shown in FIG. 8A, when the operator removes the limiting portion 64, the movable range of the slider 102 becomes a range capable of covering the whole length of the slit 101$b$ of the operation portion main body 101 in the longitudinal axis direction. In this state, the operator may push the slider 102 further toward the distal end side.

When the operator further pushes the slider 102 toward the distal end side with respect to the operation portion main body 101 in the state in which the limiting portion 64 is detached, the enlarged diameter portion 72, the loop portion 73, the hook 77, and the arm member 11 are moved to the distal end side along the axis C1 by the operation wire 62. As a result, the protrusions 18, 19, 23, 24 moves toward the distal end side with respect to the step portion 15 while the inclined surfaces at the distal end side of the protrusions 18, 19, 23, 24 is in contact with the inclined surface at the proximal end side of the step portion 15.

Figure 8C:
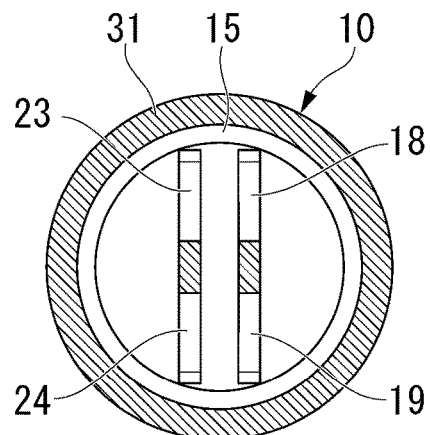
FIG. 8C is a cross-sectional view showing a broken pressing tube cut along the cutting line VIIIC-VIIIC and viewed from the proximal end of the endoscope clip shown in FIG. 8B.

As shown in FIGS. 8A and 8B, when the operator pushes the slider 102 toward the distal end side, the first arm 12 and the second arm 13 may climb on and overcome the step portion 15 in an elastically deformed state. As shown in FIG. 8C, in this process, when the arm member 11 is viewed from the proximal end side, the distance between the protrusions 18, 19 and the protrusions 23, 24 in the direction X becomes small respectively.

By the operation of the operator, in the process in which the protrusions 18, 19, 23, 24 overcomes the step portion 15 from the proximal end side, and the protrusions 18, 19, 23, 24 overcomes the step portion 15 to further move to the distal end side, the first arm 12 and the second arm 13 of the arm member 11 are also moved to the distal end side. As a result, the opening width between the first arm 12 and the second arm 13 is increased while the first arm 12 and the second arm 13 are in contact with the tapered surface 31$a$ on the distal end side of the pressing tube.

Figure 9A:
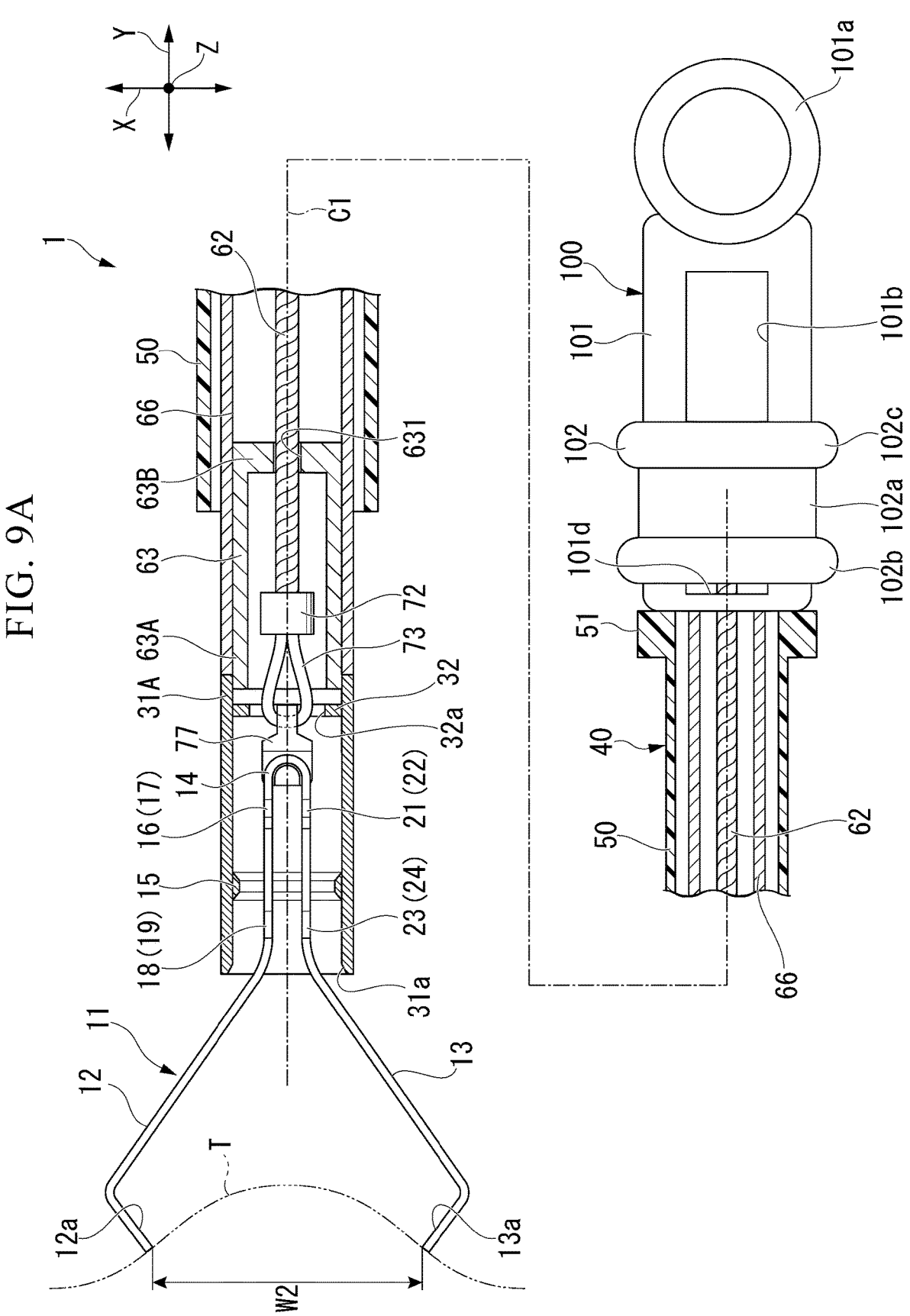
FIG. 9A is a cross-sectional side view schematically showing the endoscope clip according to the present embodiment.

As shown in FIG. 9A, when the operator advances the slider 102 until the slider 102 abuts on the distal end surface 101$d$ of the slit 101$b$ of the operation portion main body 101, the first arm 12 and the second arm 13 of the arm member 11 are substantially in a state of protruding from the pressing tube 31. In this state, the opening width of the first arm 12 and the second arm 13 of the arm member 11 becomes the maximum opening width.

According to the present embodiment, as shown in FIG. 9A, the fully-opened state in which the opening width of the arm member 11 becomes the maximum value is defined as the second open configuration of the arm member 11. The distance between the distal end of the first arm 12 and the distal end of the second arm 13 in the second open configuration is defined as a second distance W2. The second distance W2 is larger than the first distance W described above. According to this embodiment, for example, the second distance W2 may be approximately twice the first distance W1.

In the state in which the arm member 11 is in the second open configuration, the distance between the step portion (engaging portion) 15 and the protrusion portions (engaged portion) 18, 19, 23, 24 in the direction along the axis C1 (longitudinal axis) is smaller than the distance between the first locked portions 16, 17, or the second locked portions 21, 22 and the locking portion 32 in the direction along the axis C1 (longitudinal axis).

Subsequently, the operator can grasp the target tissue T by using the arm member 11 in the second open configuration following the operations similar to the above-described operations. Similar to the operation described above, the operator may pull the slider 102 toward the proximal end side to tightly bind the root of the target tissue T by the integrated arm member 11 and the pressing tube 31. More specifically, when the operator pulls back the slider 102 toward the proximal end side, similar to the operations to the arm member 11 in the first open configuration described above, the distance between the first arm 12 and the second arm 13 of the arm member 11 decreases. At the same time, the protrusions 18, 19, 23, 24 climb on and overcome the step portion 15 again from the distal end side and are located at a position at the proximal end side than the step portion 15. When the operator further pulls the slider 102 back toward the proximal end side, the first locked portions 16, 17 and the second locked portions 21, 22 climb on and overcome the locking portion 32 of the pressing tube 31 to be locked to the locking portion 32 at the proximal end side more than the locking portion 32.

In other words, when the operator pulls back the slider 102 to the proximal end side, the arm member 11 connected to the operation wire 62 may be moved to the proximal end side, and at the same time, the arm member 11 may be transitioned from the second open configuration to the closed configuration.

Subsequently, similar to the above-described operations, the operator may release the engagement between the hook 77 and the central portion 14 to indwell the clip 10 ligating the target tissue T in the body. At this time, the clip 10 is maintained in the closed configuration.

(Effect of the Endoscope Clip 1)

Hereinafter, the effect of the endoscope clip 1 according to the present embodiment will be described.

The arm member 11 of the clip 10 according to the present embodiment has the first arm 12 and the second arm 13. The arm member 11 has the closed configuration in which the distal end portion (claw 12*a*) of the first arm 12 and the distal end portion (claw 13*a*) of the second arm 13 are in contact with each other, a first open configuration in which the distal end portion of the first arm 12 and the distal end portion of the second arm 13 are separated from each other by the first distance W1, and a second open configuration in which the distal end portion of the first arm 12 and the distal end portion of the second arm 13 are separated from each other by the first distance W2.

When the limiting portion 64 is arranged in the slit 101*b* of the operation portion main body 101 while covering the operation wire 62, the movable range of the slider 102 in the slit 101*b* is restricted by the limiting portion 64. When the limiting portion 64 is removed from the slit 101*b*, the slider 102 may advance and retract in the entire range of the slit 101*b*. That is, the limiting portion 64 is configured to limit the relative movement of the slider 102 with respect to the operation portion main body 101 in the slit 101*b* of the operation portion main body 101.

On the other hand, the step portion 15 is provided on the inner circumferential surface on the distal end side of the pressing tube 31. The protrusions 18, 19, 23, 24 of the arm member 11 come into contact with the step portion 15 such that the arm member 11 is not capable of advancing and retracting with respect to the holding pipe 31 unless an external operation is performed.

According to the present embodiment, when the slider 102 moves with respect to the operation portion main body 101, the operation wire 62 connected to the slider 102, the enlarged diameter portion 72, the loop section 73, the hook 77, and the arm member 11 connected to the operation wire move with respect to the operation unit main body 101. When the arm member 11 moves with respect to the operation portion main body 101, the arm member 11 also moves with respect to the pressing tube 31 of the treatment tool main body 40.

According to the present embodiment, when the limiting portion 64 is removed from the operation portion main body 101, the protrusions 18, 19, 23, 24 may climb on and overcome the step section 15 by the operator pushing the slider 102. In the state in which the limiting portion 64 is removed from the operation portion main body 101, the operator may enlarge the opening width between the first arm 12 and the second arm 13 of the arm member 11 from the first distance W1 to the second distance W2 larger than the first distance W1 and cause the arm member to be transitioned from the first open configuration to the second open configuration by pushing the slide 102.

In other words, according to the present embodiment, the first arm 12 and the second arm 13 of the arm member 11 may be transitioned to the first open configuration in which the first arm 12 and the second arm 13 are separated by the first distance W1 or the second open configuration in which the first arm 12 and the second arm 13 are separated by the second distance W2 larger than the first distance W1 by the first arm 12 and the second arm 13 of the arm member 11 being moved with respect to the pressing tube 31. More specifically, according to the present embodiment, the arm member 11 may be transitioned from the first open configuration to the second open configuration by the first arm 12 and the second arm 13 of the arm member 11 being moved toward the distal end side (first direction) with respect to the pressing tube 31. According to the present embodiment, the first arm 12 and the second arm 13 of the arm member 11 that moves with respect to the pressing tube 31 are referred to as a movement portion of the arm member 11.

According to the present embodiment, the first locked portions 16, 17 formed on the first arm 12 of the arm member 11 and the second locked portions 21, 22 formed on the second arm 13 climb on and overcome the locking portion 32 formed at the proximal end side of the pressing tube 31 and is moved to the position at the proximal end side more than the locking portion 32 to be locked by the proximal end surface of the locking portion 32. As a result, the movement of the arm member 11 toward the distal end side with respect to the pressing tube 31 is restricted, and the target tissue T is grasped by the first arm 12 and the second arm 13 of the arm member 11 in the desired state. In the state in which the first locked portions 16, 17 and the second locked portions 21, 22 partially enter the locking portion 32 while being in contact with the locking portion 32, the operator may grasp the target tissue T again by pushing the slider 102 to the distal end side.

According to the present embodiment, the movement of the arm member 11 toward the distal end side may be restricted by both the limiting portion 64 provided in the operation portion main body 101 and the step portion 15 provided in the pressing tube 31 so as to change the opening width of the arm member 11 in stages.

According to the endoscope clip 1 according to the present embodiment, it is impossible for the protrusions 18, 19, 23, 24 of the arm member 11 to climb on and overcome the step portion 15 in the pressing tube 31 unless the limiting portion 64 disposed in the operation portion main body 101 is removed. Accordingly, the opening width of the first arm 12 and the second arm 13 of the arm member 11 is limited to be equal to or less than the first distance W1. As a result, by providing the limiting portion 64 corresponding to the size of the target tissue T that is most often treated as the treatment target, during the actual treatment, when the orientation and the opening width of the clip 10 are adjusted corresponding to the target tissue T, the operation for the operator to adjust the endoscope clip 1 may be shortened such that the maneuverability, the operation time, and the efficiency may be improved.

According to the endoscope clip 1 according to the present embodiment, when the limiting portion 64 provided in the operation portion main body 101 is removed, the protrusions 18, 19, 23, 24 may climb on and overcome the step portion 15 by the operator pushing the slider 102. Accordingly, the limiting portion 64 may be used as an indicator of an operation amount (pushing amount) of the slider 102 by the operator for causing the protrusions 18, 19, 23, 24 of the arm member 11 to climb on and overcome the step portion 15. That is, the operator may more reliably cause the arm member 11 to be transitioned from the first open configuration to the second open configuration by pushing the slider 102 after removing the limiting portion 64.

Figure 9B:
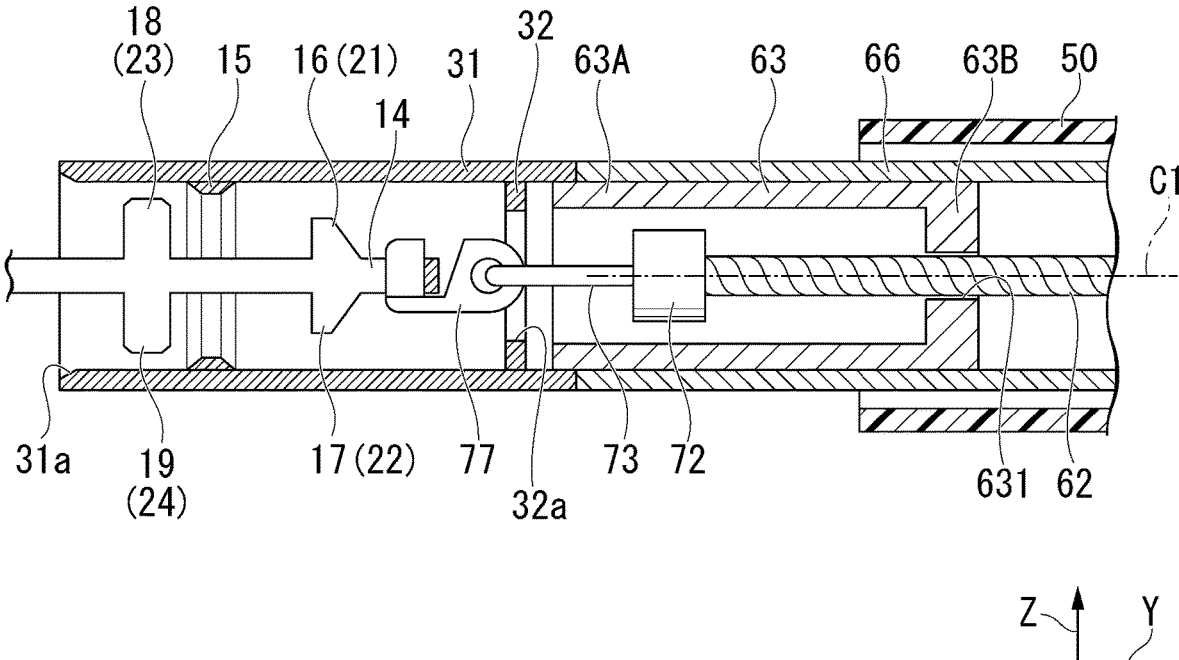
FIG. 9B is a cross-sectional planar view schematically showing the distal end portion of the endoscope clip according to the present embodiment shown in FIG. 8A.

According to the endoscope clip 1 according to the present embodiment, when the arm member 11 is in the second open configuration, as shown in FIGS. 9A and 9B, the distance between the protruding portions 18, 19, 23, 24 of the arm member 11 and the step portion 15 is smaller than the distance between the first locked portions 16, 17 or the second locked portions 21, 22 and the locking portion 32 in the direction of the axis C1 (first direction). Accordingly, when the operator pulls back the slider 102 to the proximal end side, at a timing earlier than the first locked portions 16, 17 or the second locked portions 21, 22 come in contact with the locking portion 32, the protrusions 18, 19, 23, 24 of the arm member 11 and the step portion 15 may come in contact with each other. As a result, the transition of the arm member 11 from the second open configuration to the first open configuration may be performed more reliably.

When the endoscope clip 1 according to the present embodiment is manufactured, if the relationship of the dimension of the limiting portion 64, the position of the step portion 15, and the opening width of the arm member 11 is checked in advance, it is possible to prepare several variations of the endoscope clip 1 corresponding to the various sizes of the target tissue T as the treatment target is determined so as to realize the quick response with respect to different treatment targets.

The pressing tube 31 having the limiting portion 64 and the step portion 15 has a simple configuration and is easy to be manufactured such that the endoscope clip 1 applicable to various treatment targets may be configured at low cost.

Modification

Hereinafter, a modification of the arm member 11 of the clip 10 according to the present embodiment will be described with reference to FIGS. 10A to 10D.

According to the present embodiment, the protrusions formed on the first arm 12 and the second arm 13 of the arm member 11 only has to be engageable with the step portion 15 formed on the inner circumferential surface of the pressing tube 31, the shape thereof is not particularly limited. That is, In FIGS. 10A to 10D, the examples of the configuration of the arm member 11 of the clip 10 according to the present embodiment is described; however, the configuration of the arm member 11 of the clip 10 according to the present invention is limited thereto. In FIGS. 10A to 10D, only the configuration of the engaged portion provided on the arm member 11 for engaging with the step portion (engaging portion) 15 of the pressing tube 31 is described; however, similarly, the first locked portions 16, 17 and the second locked portions 21, 22 are formed in each of the first arm 12 and the second arm 13.

Figure 10A:
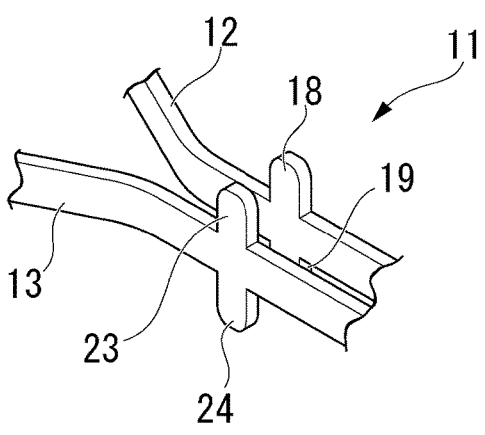
FIG. 10A is a perspective view schematically showing a configuration of the arm member of the endoscope clip according to the present embodiment.

FIG. 10A is a view showing a partial configuration of the arm member 11 of the clip 10 according to the present embodiment. As shown in FIG. 10A, two protrusions 18, 19 protruding from the lateral surface of the first arm 12 are formed in a direction perpendicular to the longitudinal direction in which the first arm 12 extends. Similarly, two protrusions 23, 24 are formed in the second arm 13. According to the present embodiment, the example in which the first arm 12 and the second arm 13 each has two protrusions has been described; however, the first arm 12 and the second arm 13 each may have only one protrusion.

Figure 10B:
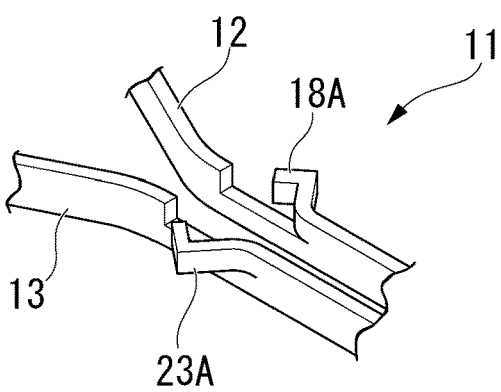
FIG. 10B is a perspective view showing a configuration of a modification of the arm member of the endoscope clip according to the present embodiment.

FIG. 10B is a view showing a partial configuration of a modification of the arm member 11 of the clip 10 according to this embodiment. As shown in FIG. 10B, the arm member 11 of the clip 10 according to the present modification may have the protrusion 18A and the protrusion 23A formed by cutting part of the first arm 12 and the second arm 13 along the longitudinal direction in which the first arm 12 and the second arm 13 extend and then bending the part being cut outwardly from the longitudinal direction.

Figure 10C:
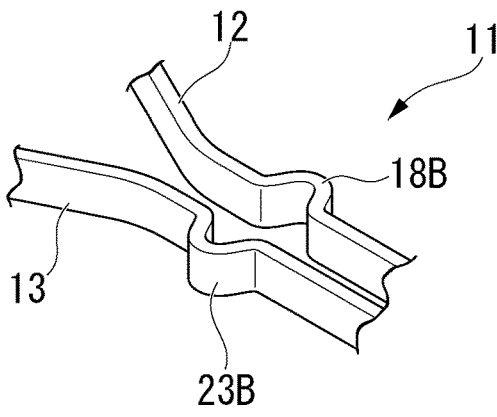
FIG. 10C is a perspective view showing a configuration of a modification of the arm member of the endoscope clip according to the present embodiment.

FIG. 10C is a view showing a partial configuration of another modification of the arm member 11 of the clip 10 according to the present embodiment. As shown in FIG. 10C, the arm member 11 of the clip 10 according to the present modification may have the protrusion 18B and the protrusion 23B formed by bending part of the first arm 12 and the second arm 13 extending along the longitudinal direction outwardly from the longitudinal direction.

Figure 10D:
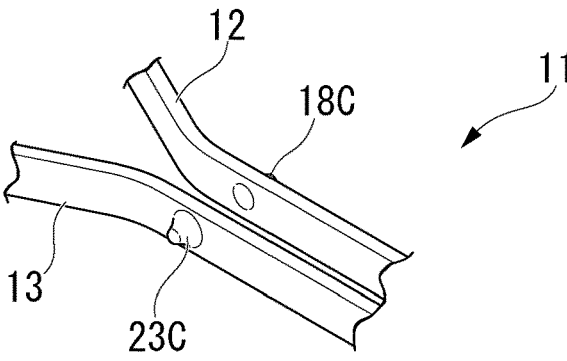
FIG. 10D is a perspective view showing a configuration of a modification of the arm member of the endoscope clip according to the present embodiment.

FIG. 10D is a view showing a partial configuration of a further modification of the arm member 11 of the clip 10 according to the present embodiment. As shown in FIG. 10D, the arm member 11 of the clip 10 according to the present modification may have the protrusion 18C and the protrusion 23C formed by pressing part of the first arm 12 and the second arm 13 outwardly from the longitudinal direction in which the first arm 12 and the second arm 13 extend.

In FIGS. 10B to 10D described above, the example in which one protrusion is formed in each of the first arm 12 and the second arm 13 has been described; however, only one of the protrusion may be formed in either of the first arm 12 or the second arm 13.

Hereinafter, with reference to FIGS. 11A to 11D, modifications of the pressing tube 31 according to the present embodiment will be described. Similar to the description above, examples of the configuration of the pressing tube 31 of the clip 10 according to the present embodiment are shown in FIGS. 11A to 11D; however, the configuration of the pressing tube 31 of the clip 10 according to the present invention is not limited thereto.

Figure 11A:
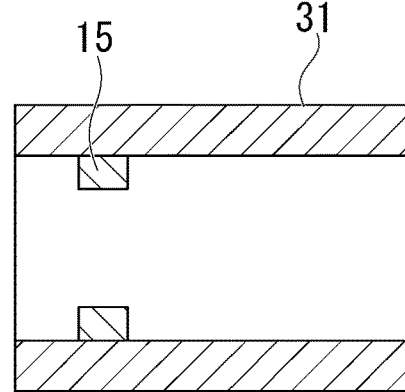
FIG. 11A is a perspective view showing a configuration of a modification of the pressing tube of the endoscope clip according to the present embodiment.

As shown in FIG. 11A, in the pressing tube 31 of the clip 10 according to the present embodiment, the step portion 15 is formed by processing part of the inner circumferential surface thereof. According to the present embodiment, the method of processing the step portion 15 is not particularly limited. For example, the step portion 15 may be formed by a method such as bonding, welding or the like on part of the inner circumferential surface of the pressing tube 31 along the direction of the axis C1. The step portion 15 may be formed on the inner circumferential surface of the pressing tube 31 by an integral molding method. According to the present embodiment, the example in which the step portion 15 is formed over the entire circumference along the circumferential direction of the inner circumferential surface of the pressing tube 31 has been described; however, the present invention is not limited only to the configuration. For example, the step portion 15 may be formed in part of the inner circumferential surface of the pressing tube 31 in the circumferential direction.

Figure 11B:
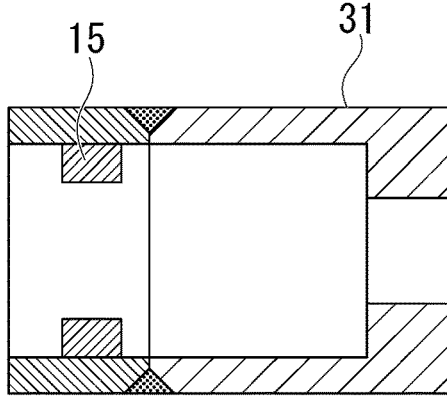
FIG. 11B is a perspective view showing a configuration of a modification of the pressing tube of the endoscope clip according to the present embodiment.

FIG. 11B shows a configuration of the pressing tube 31 of a modification of the clip 10 according to the present embodiment. As shown in FIG. 11B, the pressing tube 31 of the clip 10 according to the present modification is formed by connecting two similar tubular members by a method such as welding, bonding or the like. Each of the two tubular members forming the pressing tube 31 has an end portion protruding from the inner circumferential surface toward the central axis. The two tubular members forming the pressing tube 31 may be used as pressing tubes, respectively. In the pressing tube 31 of the clip 10 according to the present modification, the end portion of either tubular member functions as the step portion 15 of the pressing tube 31.

Figure 11C:
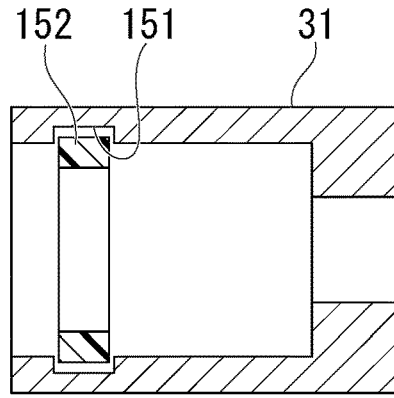
FIG. 11C is a perspective view showing a configuration of a modification of the pressing tube of the endoscope clip according to the present embodiment.
Figure 11D:
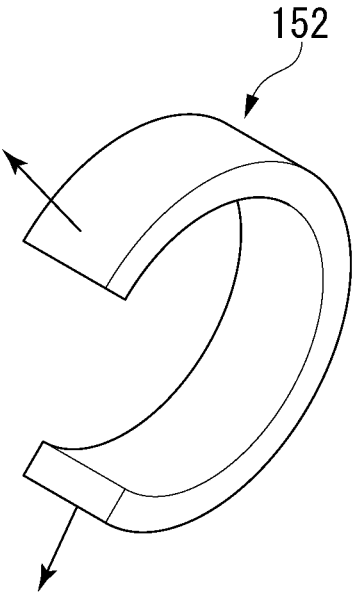
FIG. 11D is a perspective view showing a configuration of a modification of the pressing tube of the endoscope clip according to the present embodiment.

FIGS. 11C and 11D show a configuration of a pressing tube 31 according to another modification of the clip 10 according to the present embodiment. As shown in FIG. 11C, the pressing tube 31 of the clip 10 according to the present modification is formed by fitting an O-shaped ring 152 formed of rubber or a C-shaped ring 152 formed of metal or resin shown in FIG. 11D into a concave portion 151 formed on an inner circumferential surface of a tubular member. As shown in FIG. 11C, the concave portion 151 is formed by cutting off part of the inner circumferential surface of the pressing tube 31. The concave portion 151 may be formed by the integral molding method.

FIG. 11D shows the C-shaped ring member 152 provided to be fitted into the concave portion 151 of the pressing tube 31 of the clip 10 according to the present modification. The ring member 152 may be formed, for example, by cutting off part of a tubular member.

As shown in FIG. 11C, in the natural state in which no external force applies, a space having an inner diameter smaller than the inner diameter of the pressing tube 31 is formed inside the ring member 152. When the external force is applied to the ring member 152 according to the present modification, the space formed therein may be expanded and elastically deformed.

As shown in FIG. 11C, in the ring member 152, an outer diameter which is the maximum width in the radial direction with respect to the axis C1 is equal to or larger than the inner diameter of the pressing tube 31 excluding the region where the concave portion 151 is formed, and is equal to or smaller than the inner diameter of the pressing tube 31 in the region where the concave portion 151 is formed. That is, according to the present modification, the ring member 152 is configured so as to not to slip off from the concave portion 151 formed in the inner circumferential surface of the pressing tube 31 even the ring member 152 is not elastically deformed. In a case in which the ring member 152 is elastically deformed, the outer circumferential surface of the ring member 152 is contactable with the inner circumferential surface of the pressing tube 31 in the region where the concave portion 151 is formed. In the pressing tube 31 according to the present modification, the configuration by combining the ring member 152 and the concave portion

151 has the same effect with the step portion according to the above-described modifications.

Second Embodiment

An endoscope clip 1A according to a second embodiment of the present disclosure will be described below with reference to FIGS. 12 and 13. Hereinafter, the point different from the first embodiment will be mainly described. The same configurations as those of the endoscope clip 1 according to the first embodiment described above are designated by the same reference numerals, and the description thereof will be omitted.

(Configuration of Endoscope Clip 1A)

Figure 12:
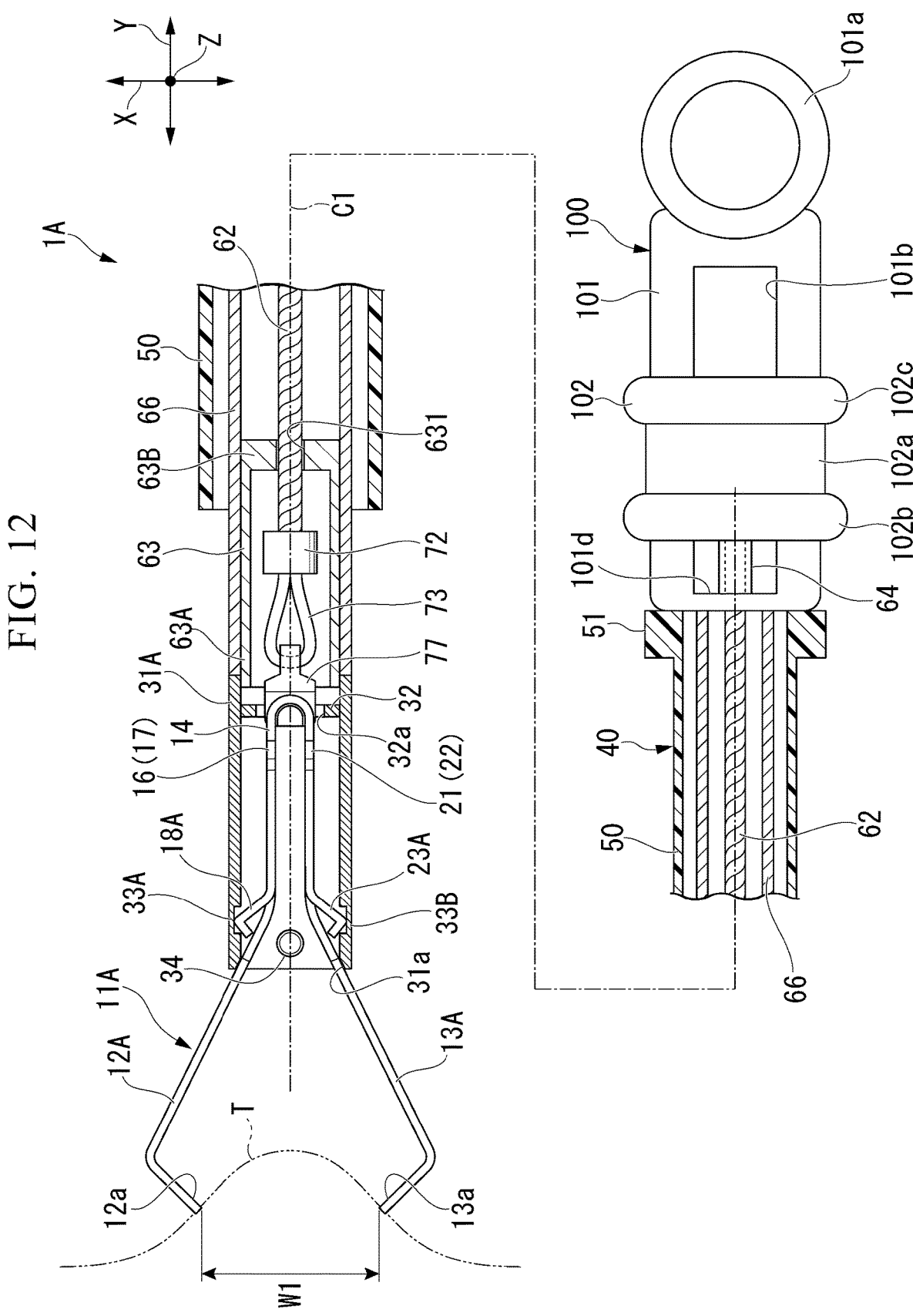
FIG. 12 is a cross-sectional perspective view schematically showing a configuration of an endoscope clip according to a second embodiment of the present disclosure.

FIG. 12 is a cross-sectional side view of the endoscope clip 1A according to the present embodiment when the arm member 11A is in the first open configuration. FIG. 13 is a cross-sectional side view of the endoscope clip 1A according to the present embodiment when the arm member 11A is in the second open configuration.

The endoscope clip 1A according to the present embodiment is different from the endoscope clip 1 according to the above-described first embodiment in the embodiment of the engagement of the arm member 11A and the pressing tube 31A.

As shown in FIG. 12, the endoscope clip 1A according to the present embodiment is configured to include a clip 10A and a treatment tool main body (applicator) 40. The clip 10A according to the present embodiment has an arm member 11A including a first arm 12A and a second arm 13A, and a central portion 14 provided between the first arm 12A and the second arm 13A. In the arm member 11A, the first arm 12A is formed with a protrusion 18A having the shape as shown in FIG. 10B along the longitudinal direction in which the first arm 12A itself extends. That is, the first arm 12A has a protrusion 18A formed by bending a portion cut along the longitudinal direction in which the first arm 12A itself extends outwardly with respect to the longitudinal direction. Similarly, the second arm 13A has a protrusion 23A having the same shape as the protrusion 18A.

On the other hand, on the inner circumferential surface of the pressing tube 31A according to the present embodiment, the notches 33A, 33B are formed by cutting off a portion of the inner circumferential surface of the pressing tube 31A corresponding to the protrusion 18A and the protrusion 23A. In the side view shown in FIG. 12, the notches 33A, 33B are line-symmetric with respect to the axis C1 of the pressing tube 31. The notches 33A, 33B have a depth that the notches 33A, 33B and the protrusion 18A or the protrusion 23A may be engaged with each other by at least part of the protrusion 18A or the protrusion 23A entering the notches 33A, 33B. The dimension of the notches 33A, 33B in the longitudinal direction along the axis C1 of the pressing tube 31 is not particularly limited; however, it is preferable that the protrusion 18A and the protrusion 19 have the dimension so as to not to easily slip from the notches 33A, 33B when engaged with the notches 33A, 33B, respectively.

In the endoscope clip 1 according to the first embodiment described above, the step portion 15 is provided over the entire circumference along the circumferential direction of the inner circumferential surface of the pressing tube 31. Compared with such a configuration, the endoscope clip 1A according to the present embodiment is configured to have the notch 33A, 33B by cutting off only a portion along the circumferential direction of the inner circumferential surface of the pressing tube 31A. Accordingly, in the endoscope clip 1A according to the present embodiment, it is preferable to determine the relative positional relationship between the arm member 11A and the pressing tube 31A in advance so as to correspond the protrusion 18A and the protrusion 23A with the notches 33A, 33B respectively.

As described above, in the endoscope clip 1 according to the first embodiment, by rotating the operation wire 62 with respect to the sheath 61, the arm member 11 may be rotated around the axis C1 with respect to the pressing tube 31. Similarly, according to the present embodiment, when the operation wire 62 is unintentionally rotated with respect to the sheath 61, in the circumferential direction of the inner circumferential surface of the pressing tube 31A, it is possible that the relative positional relationship between the protrusion 18A and the notch 33A, and the relative positional relationship between the protrusion 23A and the notch 33B are displaced.

According to the present embodiment, in the circumferential direction of the inner circumferential surface of the pressing tube 31A, a rotation prevention member 34 may be provided inside the pressing tube 31A to prevent displacement of the relative positional relationship between the protrusion 18A and the notch 33A, and the relative positional relationship between the protrusion 23A and the notch 33B. In the side view in FIG. 12, the rotation prevention member 34 is provided between the first arm 12A and the second arm 13A of the arm member 11A. According to the present embodiment, the rotation prevention member 34 may be, for example, a pin that penetrates the pressing tube 31A in a direction perpendicular to the axis C1 direction of the pressing tube 31A. The rotation prevention member 34 only has to be provided between the first arm 12A and the second arm 13A to restrict the rotation of the arm member 11 with respect to the pressing tube 31A and with the axis C1 as a rotation center, and the position thereof in the direction of the axis C1 of the pressing tube 34 is not particularly limited. For example, the rotation prevention member 34 may be formed near the distal end opening of the pressing tube 31A so as not to disturb the advancement and retraction of the arm member 11A with respect to the pressing tube 31A.

The other configurations of the endoscope clip 1A according to the present embodiment is the same as that of the endoscope clip 1 according to the above-described first embodiment. For example, as shown in FIG. 12, the endoscope clip 1A according to the present embodiment is an integrated configuration in which the pressing tube 31A and the sheath 66 are connected and integrated by the connection member 63. That is, the pressing tube 31A and the sheath 66 are fixed by the connection member 63 in the direction of the axis C1 of the pressing tube 31A. For example, the first locked portions 16, 17 formed on the first arm 12A and the second locked portions 21, 22 formed on the second arm 13A are configured to climb on and overcome the locking portion 32 and locked by the proximal end surface of the locking portion 32 such that the movement of the arm member 11A toward the distal end side with respect to the pressing tube 31A is restricted, and the target tissue T is grasped by the first arm 12A and the second arm 13A of the arm member 11A in a desired state. In the state in which the first locked portions 16, 17 and the second locked portions 21, 22 are in contact with the locking portion 32 while partially entering the locking portion 32, the operator may push the slider 102 toward the distal end side to grasp the target tissue T again.

(Operation of Endoscope Clip 1A)

Hereinafter, the operation of the endoscope clip 1A according to the present embodiment will be described focusing on the process in which the arm member 11A of the endoscope clip 1A according to the present embodiment is transitioned from the first open configuration to the second open configuration.

FIG. 12 shows the configuration when the arm member 11A of the endoscope clip 1A according to the present embodiment is in the first open configuration. As shown in FIG. 12, when the arm member 11A is in the first open configuration, the protrusion 18A of the first arm 12A enters the notch 33A, and the protrusion 18A and the notch 33A are engaged with each other. The protrusion 23A of the second arm 13A enters the notch 33B, and the protrusion 23A and the notch 33B are engaged with each other. In this state, the protrusion 18A and the protrusion 23A may be elastically deformed. At this time, in the operation portion 100 at the proximal end side, the distal end surface of the slider 102 contacts the proximal end surface of the limiting portion 64, and the slider 102 and the limiting portion 64 are engaged. Inside the connection member 63, the enlarged diameter portion 72 is located apart from the proximal end portion 63B of the connection member 63 and is located at the distal end side more than the proximal end portion 63B.

In this state, the arm member 11A is biased toward a direction in which the arm member 11A protrudes from the pressing tube 31A due to the elastic restoring force of the first arm 12A and the second arm 13A. However, since the protrusion 18A and the protrusion 23A are engaged with the notch 33A and the notch 33B, respectively, and the slider 102 at the proximal end side is in contact and engaged with the limiting portion 64, it is impossible for the arm member 11A to overcome the region where the notch 33A and the notch 33B are provided in the pressing tube 31A and move to the distal end side. Accordingly, the first arm 12A and the second arm 13A of the arm member 11A come into contact with the tapered surface 31a at the distal end portion of the pressing tube 31A, and the opening width between the first arm 12A and the second arm 13A is the first distance W1.

According to the present embodiment, as shown in FIG. 12, the slider 102 comes in contact with the limiting portion 64 and is positioned at the most distal position with respect to the operation portion main body 101, that is, the neutral position. When the slider 102 is at the neutral position, the operation wire 62 connected to the slider 102 and the arm member 11A connected to the operation wire 62 are also in a state in which they cannot be advanced with respect to the operation portion main body 101. Accordingly, the state in which the opening width between the first arm 12A and the second arm 13A of the arm member 11A is the first distance W1 is maintained. In other words, according to the present embodiment, the protrusion 18A and the protrusion 23A are engaged with the notch 33A and the notch 33B, respectively, and the slider 102 on the proximal end side is in contact and engaged with the limiting portion 64 such that the transition of the arm member 11A from the first open configuration to the second open configuration is restricted.

The operator may use the arm member 11A in the first open configuration to treat the target tissue T by the similar operations as the operations when using the endoscope clip 1 according to the first embodiment.

When the arm member 11A of the clip 10A according to the present embodiment is in the first open configuration, the first distance W1 as the opening width between the first arm 12A and the second arm 13A is smaller than the size of the target tissue T, it is necessary for the operator to cause the arm member 11A to be transitioned from the first open configuration to the second open configuration, and enlarges the opening width between the first arm 12A and the second arm 13A to the second distance W2 which is the maximum opening width.

At this time, the operator may remove the limiting portion 64 from the slit 101b of the operation portion main body 101, and then moves the slider 102 to the distal end side so as to further enlarge the opening width between the first arm 12A and the second arm 13A of the arm member 11A.

Figure 13:
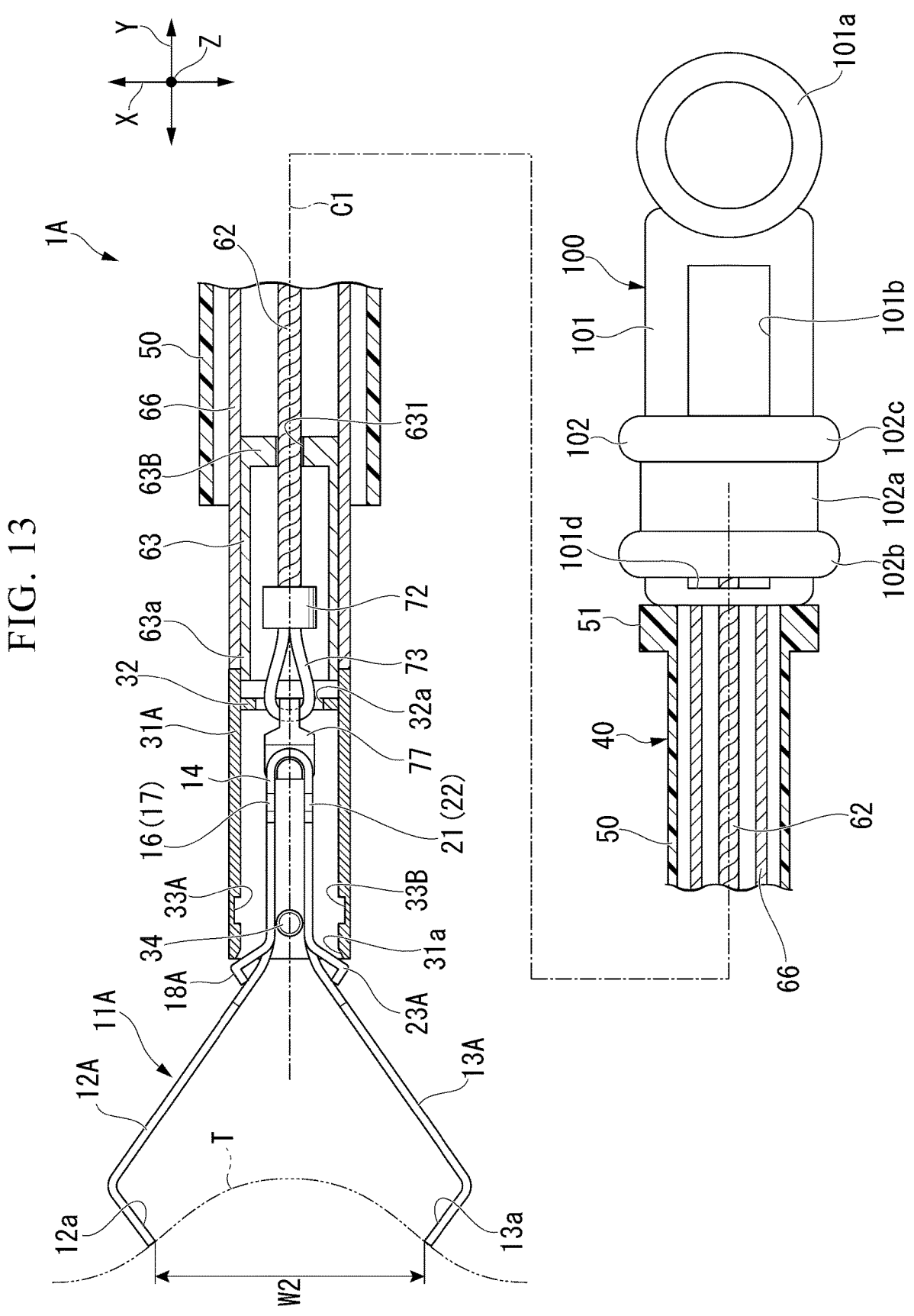
FIG. 13 is a cross-sectional perspective view schematically showing the configuration of the endoscope clip according to the present embodiment.

In FIG. 13, the configuration of the endoscope clip 1A in the second open configuration is shown. According to the present embodiment, the operator pushes the slider 102 with the limiting portion 64 removed such that the enlarged diameter portion 72, the loop portion 73, the hook 77, and the arm member 11A move toward the distal end side along the axis C1. As a result, the protrusion 18A and the protrusion 23A climb on and overcome the notch 33A and the notch 33B and positioned at the distal end side more than the notch 33A and the notch 33B. That is, when the operator removes the limiting portion 64 and pushes the slider 102 toward the distal end side, the arm member 11A of the clip 10A may be transitioned from the first open configuration to the second open configuration.

As shown in FIG. 13, when the operator advances the slider 102 until the slider 102 comes in contact with the distal end surface 101d of the slit 101b of the operation portion main body 101, the first arm 12A and the second arm 13A of the arm member 11A are in a state of almost protruding from the pressing tube 31A. In this state, the opening width between the first arm 12A and the second arm 13A of the arm member 11A becomes the second distance W2 as the maximum opening width. In this state, the distance between the protruding portion 18A or the protruding portion 23A and the notch 33A or the notch 33B in the direction of the axis C1 is smaller than the distance between the first locked portions 16, 17 or the second locked portions 21, 22 and the locking portion 32.

Subsequently, the operator may use the arm member 11A in the first open configuration to grasp and treat the target tissue T by the same operation as the operations when using the endoscope clip 1 according to the first embodiment.

According to the endoscope clip 1A according to the present embodiment, similarly to the endoscope clip 1 according to the above-described first embodiment, in the operation portion main body 101, since the slider 102 is engaged with the limiting portion 64, and the portion 18A and the protrusion 23A are engaged with the notch 33A and the notch 33B provided in the pressing tube 31A respectively, the movement of the arm member 11A toward the distal end side may be restricted. Accordingly, the opening width between the first arm 12A and the second arm 13A of the arm member 11A may be changed in stages. As a result, by providing the limiting portion 64 corresponding to the size of the target tissue T that is most often treated as the treatment target, during the actual treatment, when the orientation and the opening width of the clip 10 are adjusted corresponding to the target tissue T, the operation for the operator to adjust the endoscope clip 1 may be shortened such that the maneuverability, the operation time, and the efficiency may be improved.

Third Embodiment

Hereinafter, an endoscope clip 1B according to a third embodiment of the present invention will be described with reference to FIGS. 14 to 16. Hereinafter, differences from the above-described embodiments will be mainly described. The same components as those of the endoscope clip according to each of the above-described embodiments are designated by the same reference numerals, and the description thereof will be omitted.

(Configuration of Endoscope Clip 1B)

Figure 14:
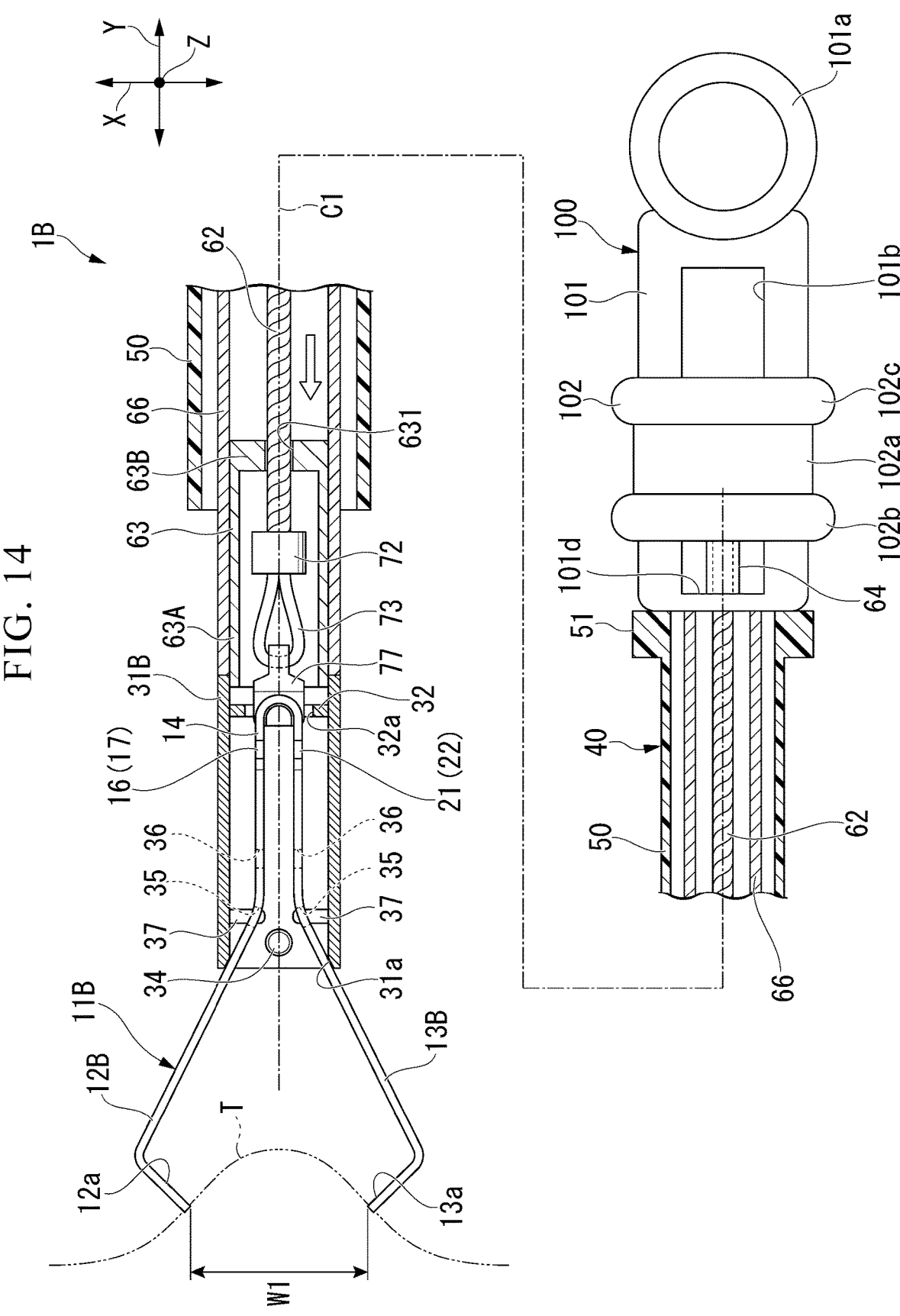
FIG. 14 is a cross-sectional perspective view schematically showing a configuration of an endoscope clip according to a third embodiment of the present disclosure.

FIG. 14 is a cross-sectional side view of the endoscope clip 1B according to the present embodiment when the arm member 11B is in the first open configuration. FIG. 15 is a cross-sectional side view of the endoscope clip 1B according to the present embodiment when the arm member 11B is in the second open configuration. FIG. 16 is a perspective view schematically showing a partial configuration of the arm member 11B according to the embodiment.

The endoscope clip 1B according to the present embodiment differs from the above-described embodiments in the embodiment of the engagement between the pressing tube 31B and the arm member 11B.

As shown in FIG. 14, the endoscope clip 1B according to the embodiment includes a clip 10B and a treatment tool body (applicator) 40.

The clip 10B according to the present embodiment has an arm member 11B including a first arm 12B and a second arm 13B, and a central portion 14 provided between the first arm 12B and the second arm 13B. In each of the first arm 12B and the second arm 13B in the arm member 11B, two circular holes are formed along the longitudinal direction in which the arm member 11B itself extends.

Figure 16:
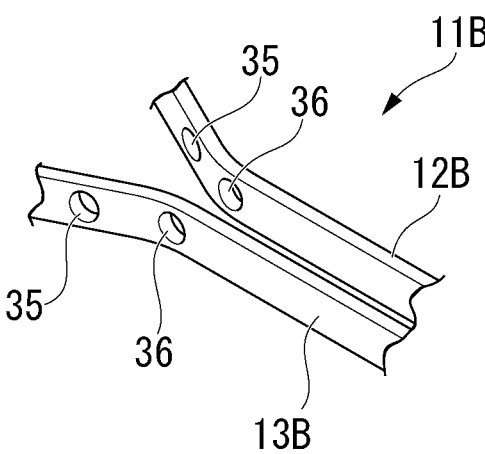
FIG. 16 is a perspective view schematically showing part of a configuration of the arm member of the endoscope clip according to the present embodiment.

More specifically, as shown in FIG. 16, along the longitudinal direction in which the first arm 12B extends, a circular first hole (first engaged portion) 35 and a second hole (second engaged portion) with the same size are formed. As shown in FIG. 14, the first hole 35 is formed at the distal end side more than the second hole 36 along the longitudinal direction in which the first arm 12B extends. Similarly, the first hole 35 and the second hole 36 are formed in the second arm 13B. According to the present embodiment, the first hole 35 and the second hole 36 are formed as through holes with dimensions suitable for pins 37 described below to enter and engage therewith. In the arm member 11B according to the present embodiment, in the first arm 12B or the second arm 13B, the first locked portions 16, 17 or the second locked portions 21, 22 are provided at the proximal end side more than the second hole 36.

Figure 15:
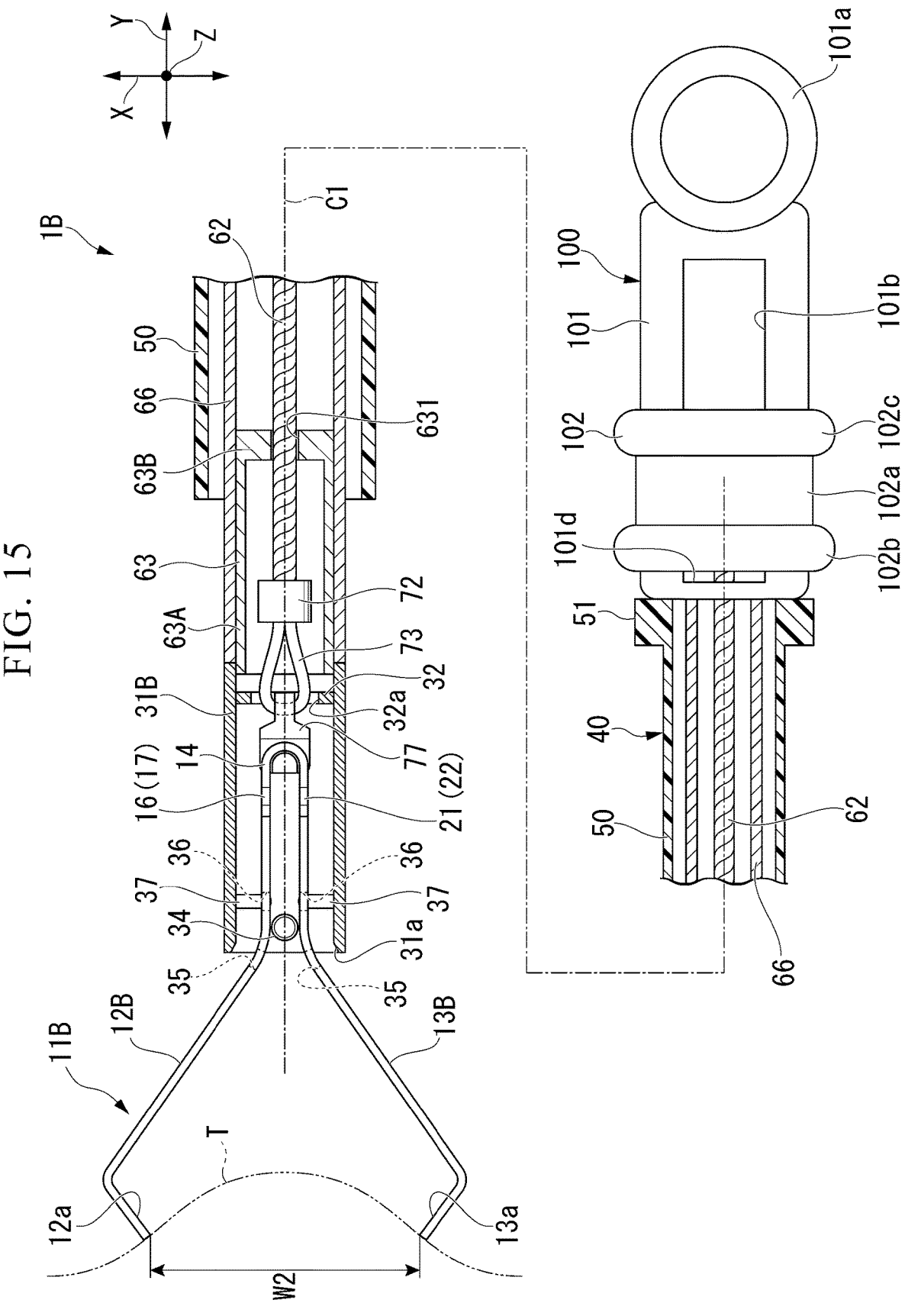
FIG. 15 is a cross-sectional perspective view schematically showing the configuration of the endoscope clip according to the present embodiment.

As shown in FIGS. 14 and 15, the clip 10B according to the present embodiment has a pair of pins (engaging members) 37 formed to protrude from the inner circumferential surface of the pressing tube 31B toward the axis C1. The pair of pins 37 are formed in line symmetry with respect to the axis C1 of the pressing tube 31B. According to the present embodiment, the pair of pins 37 only have to be formed in a shape capable of engaging with the above-described first hole 35 and second hole 36, and the specific shape is not limited. For example, the pair of pins 37 may be formed in a cylindrical shape having an outer diameter smaller than the diameters of the first hole 35 and the second hole 36. The length of the pair of pins 37 protruding inwardly from the inner circumferential surface of the pressing tube 31B is not particularly limited. For example, the distance between the distal ends of the pair of pins 37 may be smaller than the distance between the first arm 12B and the second arm 13B disposed inside the pressing tube 31B.

According to the present embodiment, as shown in FIG. 14, similar to the above-described second embodiment, the rotation prevention member 34 is provided inside the pressing tube 31B. By providing the rotation prevention member 34 in the pressing tube 31B, it is possible to restrict the rotation of the arm member 11B around the axis C1 with respect to the pressing tube 31B. Accordingly, in the clip 10B, it is possible to prevent the relative positional relationship between the pin 37 with the first hole 35 and the second hole 36 from displacing in the circumferential direction of the inner circumferential surface of the pressing tube 31B. As shown in FIG. 14 and FIG. 15, similar to the above-described first and second embodiments, the locking portion 32 is formed at the proximal end side of the pair of pins 37 and at a position at the distal end side more than the proximal end opening of the pressing tube 31B by a predetermined distance.

(Operation of Endoscope Clip 1B)

Hereinafter, the operations of the endoscope clip 1B according to the present embodiment will be described by focusing on the process in which the arm member 11B of the endoscope clip 1B according to the present embodiment is transitioned from the first open configuration to the second open configuration.

FIG. 14 is a view showing the configuration of the arm member 11B of the endoscope clip 1B according to the present embodiment when the arm member 11B is in the first open configuration. As shown in FIG. 14, a pair of engaged members 37 are locked in the first hole 35 of the arm 12B and the first hole 35 of the arm 13B, respectively. In this state, the arm member 11B is biased in a direction protruding from the pressing tube 31B due to the elastic restoring force of the first arm 12B and the second arm 13B. However, since the pair of pins 37 are engaged in the first hole 35 and the slider 102 at the proximal end side is in contact with the limiting portion 64, the arm member 11B does not further move toward the distal end side from the position where the pair of pins 37 are provided. It does not move further to the distal end side. Accordingly, the first arm 12B and the second arm 13B of the arm member 11B are in contact with the tapered surface 31a at the distal end portion of the pressing tube 31B, and the opening width therebetween is the first distance W1.

As shown in FIG. 14, according to the present embodiment, the slider 102 is in contact with the limiting portion 64 and is at the most distal position with respect to the operation portion main body 101, that is, at the neutral position. When the slider 102 is at the neutral position, the operation wire 62 connected to the slider 102 and the arm member 11B are also in a state in which they are impossible to advance with respect to the operation portion main body 101. Accordingly, the state in which the opening width between the first arm 12B and the second arm 13B of the arm member 11B is the first distance W1 is maintained. In other words, according to the present embodiment, in the state in which the pair of pins 37 are locked in the first hole 35, the transition of the arm member 11B from the first open configuration to the second open configuration is restricted.

The operator may use the arm member 11B in the first open configuration to grasp and treat the target tissue T by the same operations when using the endoscope clip 1 according to the first embodiment.

When the arm member 11B of the clip 10B according to the present embodiment is in the first open configuration, and the first distance W1 as the opening width between the first arm 12B and the second arm 13B is smaller than the size of the target tissue T, it is necessary for the operator to cause the arm member 11B to be transitioned from the first open configuration to the second open configuration to enlarge the opening width between the first arm 12B and the second arm 13B to the second distance W2 which is the maximum opening width.

At this time, the operator may remove the limiting portion 64 from the slit 101b of the operation portion main body 101 and then move the slider 102 to the distal end side so as to further enlarge the opening width between the first arm 12B and the second arm 13B of the arm member 11B.

FIG. 15 is a view showing the configuration when the endoscope clip 1B according to the present embodiment is in the second open configuration. According to the present embodiment, the operator pushes the slider 102 toward the distal end side with the limiting portion 64 removed, such that the enlarged diameter portion 72, the loop portion 73, the hook 77, and the arm member 11B are moved toward the distal end side along the axis C1. As a result, the first arm 12B and the second arm 13B of the arm member 11B are elastically deformed toward the axis C1 along the direction in which the pin 37 extends. The pin 37 may be removed from the first hole 35 by reducing the distance between the first arm 12B and the second arm 13B of the arm member 11B. At this time, the rotation prevention member 34 restricts the relative rotation of the arm member 11B with respect to the pressing tube 31B with the axis C1 as the rotation center.

Accordingly, in the state in which the pin 37 is removed from the first hole 35, the first arm 12B and the second arm 13B move to the distal end side while the pin 37 contacting the lateral surfaces of the first arm 12B and the second arm 13B of the arm member 11B by the user further pushing the slider 102 toward the distal end side. In other words, the pin 37 moves to the proximal end side with respect to the first arm 12B and the second arm 13B while contacting the first arm 12B and the second arm 13B of the arm member 11B.

When the operator pushes the slider 102 toward the distal end side, the engaged member 37 is removed from the first hole 35 and relatively moves toward the proximal end side with respect to the first arm 12B and the second arm 13B so as to enter the second hole 36 and engage with the second hole 36. According to the present embodiment, as shown in FIG. 15, when the operator advances the slider 102 until it contacts on the distal end surface 101d of the slit 101b of the operation portion main body 101, the engaged member 37 moves to the position of the second hole 36 with respect to the first arm 12B and the second arm 13B. At this time, the pin 37 enters the second hole 36 and engage with the second hole 36 due to the elastic restoring force of the first arm 12B and the second arm 13B.

According to the present embodiment, in the state in which the slider 102 is in contact with the distal end surface 101d of the slit 101b of the operation portion main body 101 and the pin 37 is locked in the second hole 36, the arm member 11B is not further advanceable with respect to the pressing tube 31. That is, the opening width between the first arm 12B and the second arm 13B of the arm member 11B is impossible to further enlarged. In this state, the arm member 11B of the clip 10B is in the second open configuration. That is, the opening width of the arm member 11B between the first arm 12B and the second arm 13B is the second distance W2. In this state, the distance between the pair of pins 37 and the pair of first holes 35 along the direction of the axis C1 is smaller than the distance between the first locked portions 16, 17 or the second locked portions 21, 22 and the locking portion 32. In other words, according to the arm member 11B according to the present embodiment, the distance between the first hole 35 and the second hole 36 formed in the first arm 12B or the second arm 13B along the direction of the axis C1 is set to be smaller than the distance between the first locked portions 16, 17 or the second locked portions 21, 22 and the locking portion 32.

According to the present embodiment, the operator removes the limiting portion 64 and pushes the slider 102 until the slider 102 comes into contact with the distal end surface 101d of the slit 101b of the operation portion main body 101 such that the arm member 11B of the clip 10B may be transitioned from the first open configuration to the second open configuration.

Subsequently, the operator may uses the arm member 11B in the second open configuration to grasp and treat the target tissue T by the same operation as using the endoscope clip 1 according to the first embodiment.

According to the endoscope clip 1B according to the present embodiment, similar to the endoscope clip 1 according to the above-described first embodiment, in the state in which the slider 102 is engaged with the limiting portion 64 and the arm member 11 is locked in the first hole 35, the movement of the arm member 11B toward the distal end side may be restricted. In other words, the transition of the arm member 11B from the first open configuration to the second open configuration may be restricted.

According to the endoscope clip 1B according to the present embodiment, the operator removes the limiting portion 64 and pushes the slider 102 until the slider 102 comes into contact with the distal end surface 101d of the slit 101b of the operation portion main body 101 such that the arm member 11B may be transitioned from the first open configuration to the second open configuration.

Accordingly, the opening width between the first arm 12B and the second arm 13B of the arm member 11B of the endoscope clip 1B according to the present embodiment may be changed in stages. As a result, the endoscope clip 1B according to the present embodiment has the same effect as the endoscope clip according to each of the above embodiments of the present disclosure.

According to the present embodiment, the positions where the first hole 35 and the second hole 36 are formed in the longitudinal direction in which the first arm 12B and the second arm 13B extend are not particularly limited. For example, as described above, in the state in which the first arm 12B and the second arm 13B are extended in a substantially linear shape, the distance between the first hole 35 and the second hole 36 is may be set to be smaller than the distance between the engaged portions 16, 17 or the second locked portions 21, 22 and the locking portion 32.

According to the present embodiment, an example in which the first hole 35 and the second hole 36 are formed as through holes has been described; however, the configuration of the endoscope clip 1B according to the present embodiment is not limited thereto. The first hole 35 and the second hole 36 only have to be formed in a shape capable of being engaged with the pin 37 and may be formed as non-through holes. For example, each of the first arm 12B and the second arm 13B of the arm member 11B may have a concave portion on the outer surface facing the position where the pin 37 is provided, and the concave portion may have a dimension suitable for at least the tip end portion of the pin 37 to enter.

Fourth Embodiment

Hereinafter, an endoscope clip 1C according to a fourth embodiment of the present disclosure will be described with reference to FIGS. 17A to 19. Hereinafter, differences from the above-described embodiments will be mainly described. The same configuration as those of the endoscope clip according to each of the above-described embodiments are designated by the same reference numerals, and the description thereof will be omitted.

(Configuration of Endoscope Clip 1C)

Figure 17A:
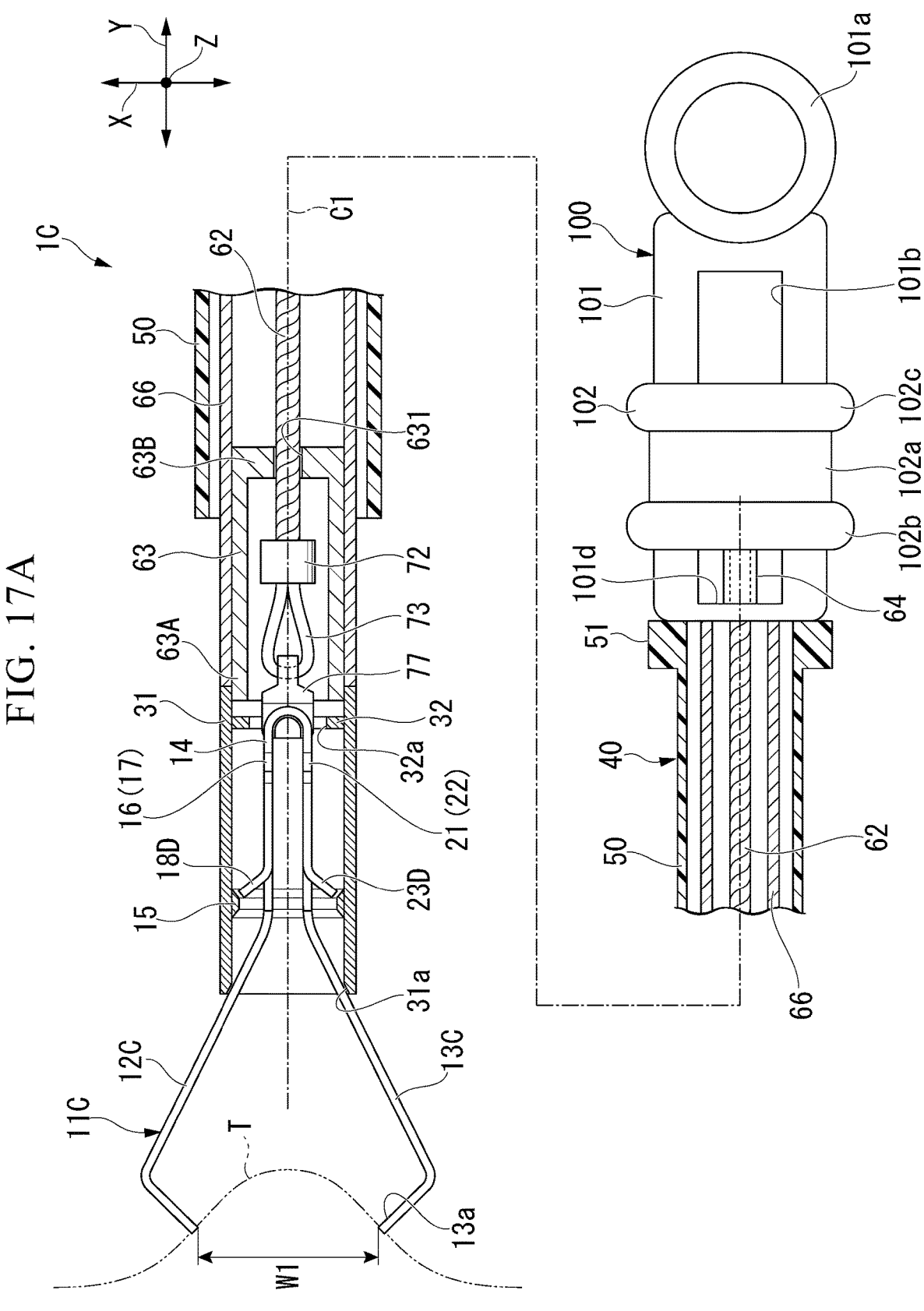
FIG. 17A is a cross-sectional side view schematically showing a configuration of an endoscope clip according to a fourth embodiment of the present disclosure.
Figure 17B:
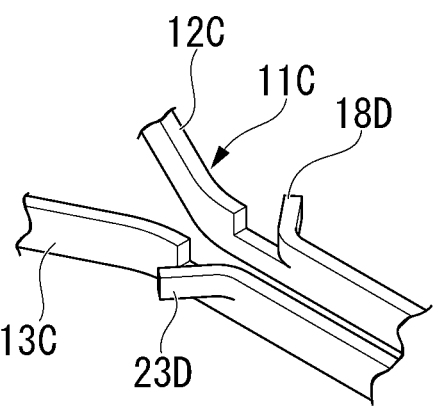
FIG. 17B is a perspective view schematically showing part of a configuration of the arm member of the endoscope clip according to the present embodiment.
Figure 18A:
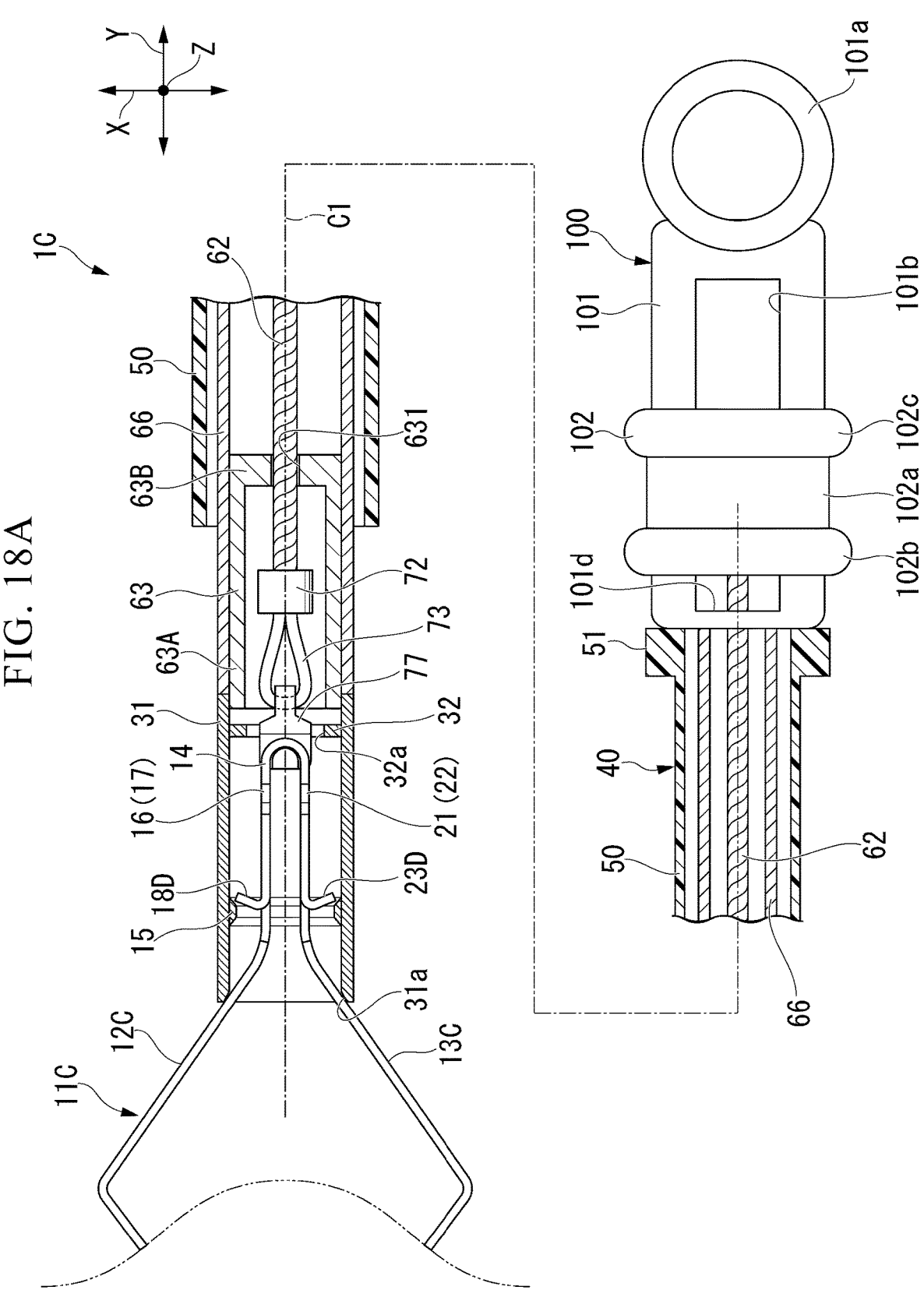
FIG. 18A is a cross-sectional side view schematically showing the configuration of the endoscope clip according to the present embodiment.
Figure 18B:
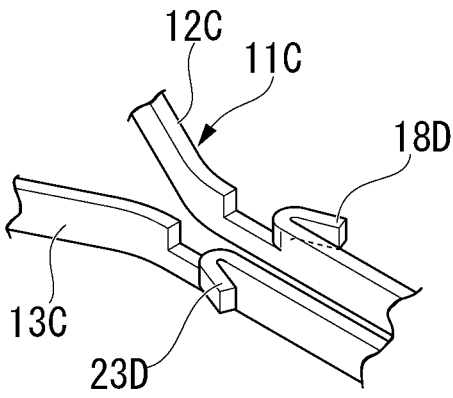
FIG. 18B is a perspective view schematically showing part of a configuration of the arm member of the endoscope clip according to the present embodiment.
Figure 19:
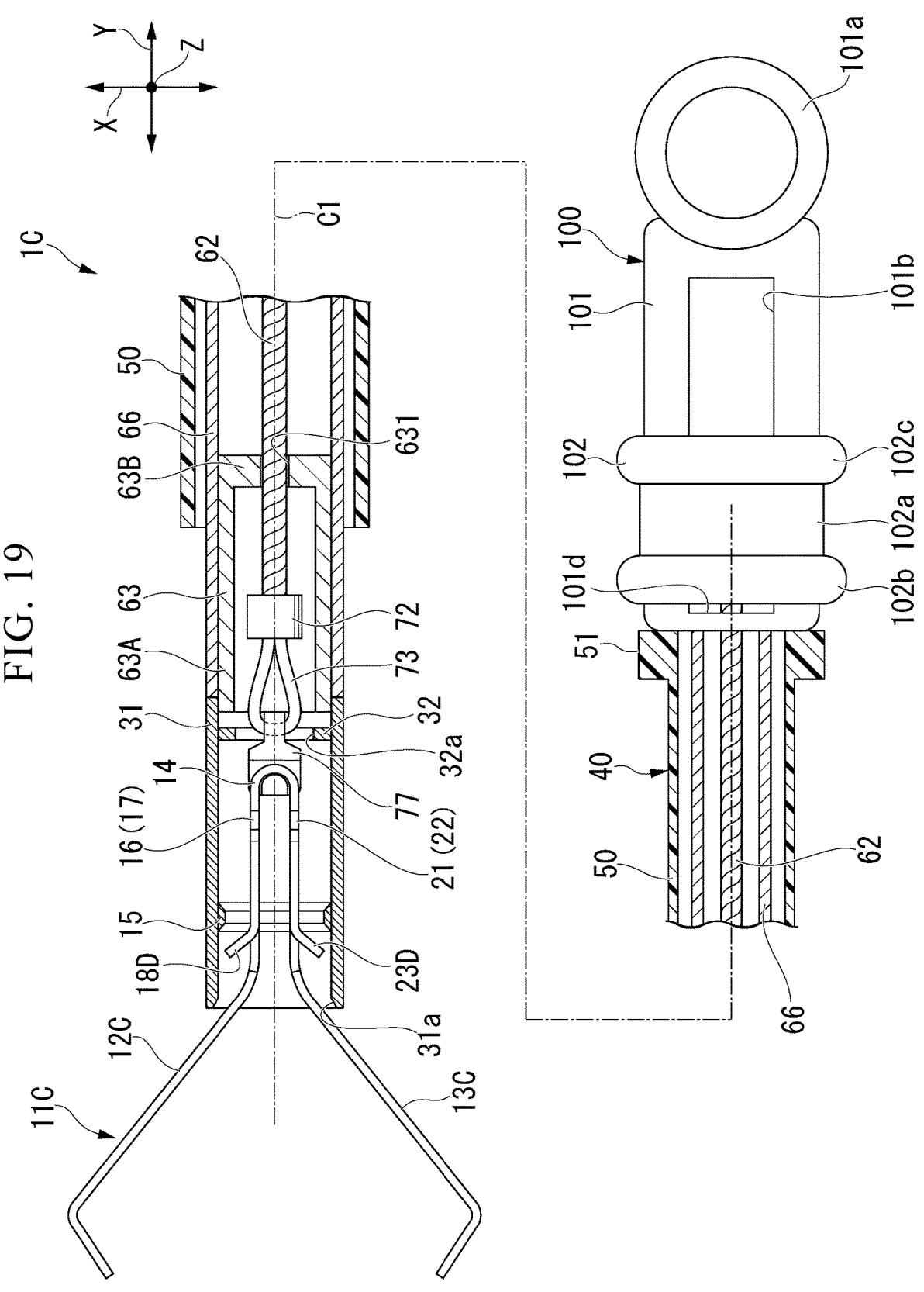
FIG. 19 is a cross-sectional side view schematically showing the configuration of the endoscope clip according to the present embodiment.

FIG. 17A is a cross-sectional side view showing a first open configuration of the arm member 11C of the endoscope clip 1C according to the present embodiment. FIG. 17B is a perspective view showing a partial configuration of the arm member 11C of the endoscope clip 1C according to the present embodiment. FIG. 18A is a cross-sectional side view showing the operation of the arm member 11C of the endoscope clip 1C according to the present embodiment. FIG. 18B is a perspective view showing a partial configuration of the arm member 11C of the endoscope clip 1C in FIG. 18A. FIG. 19 is a cross-sectional side view showing a second open configuration of the arm member 11C of the endoscope clip 1C.

As shown in FIG. 17A, in the endoscope clip 1C according to the present embodiment, compared with the endoscope clip 1 according to the first embodiment, the first arm 12C and the second arm 13C of the arm member 11C have a pair of arm notch portions (engaged portions) 18D and 23D formed by cutting off a portion of the first arm 12C and the second arm 13C respectively.

As shown in FIG. 17B, the pair of arm notches 18D, 23D according to the present embodiment provide the elastically restoring force outwardly from the longitudinal direction of the first arm 12C and the second arm 13C respectively. Accordingly, in the natural state in which the external force does not apply on the arm member 11C, the pair of arm notches 18D, 23D are elastically deformed and bent outward from the longitudinal direction of the first arm 12 and the second arm 13. That is, in the endoscope clip 1C according to the present embodiment, as shown in FIG. 17A, the distal ends of the pair of the arm notches 18D, 23D may come in contact with the step portion 15 provided in the pressing tube 31. In the endoscope clip 1C according to the present embodiment, the pair of arm notches 18D, 23D are formed to have a flap shape to be elastically deformable.

Other configurations of the clip 10C of the endoscope clip 1C according to the present embodiment are the same as the configurations of the clip 10 of the endoscope clip 1 according to the first embodiment described above. Specifically, according to the present embodiment, the treatment tool main body 40 including the operation portion 100 at the proximal end side has the same configuration as the endoscope clip 1 according to the first embodiment. That is, the endoscope clip 1C according to the present embodiment has the operation portion 100 including the operation portion main body (handle) 101, the slider 102, and the limiting portion 64.

(Operation of Endoscope Clip 1C)

Hereinafter, the operation of the endoscope clip 1C according to the present embodiment will be described by focusing on the process in which the arm member 11C of the endoscope clip 1C according to the present embodiment is transitioned from the first open configuration to the second open configuration.

FIG. 17A is a view showing configuration of the endoscope clip 1C when the arm member 11C of the endoscope clip 1C according to the present embodiment is in the first open configuration. As shown in FIG. 17A, when the arm member 11C is in the first open configuration, the slider 102 is in contact with the limiting portion 64, and the pair of arm cutouts 18D, 23D are in contact with the step portion 15. In this state, due to the elastically restoring force of the first arm 12C and the second arm 13C of the arm member 11C, the arm member 11C is biased in a direction of protruding from the pressing tube 31. The pair of arm notches 18D, 23D are in contact and locked by the step portion 15; however, the pair of arm notches 18D, 23D does not climb on and overcome the step portion 15.

Accordingly, the first arm 12C and the second arm 13C of the arm member 11C come into contact with the tapered surface 31a of the distal end portion of the pressing tube 31, and the opening width between the first arm 12C and the second arm 13C is the first distance W1.

According to the present embodiment, as shown in FIG. 17A, the slider 102 is in contact with the limiting portion 64 and at the most distal position with respect to the operation portion main body 101, that is, at the neutral position. When the slider 102 is at the neutral position, the operation wire 62 connected to the slider 102 and the arm member 11C are also in a state in which they are not advanceable with respect to the operation portion main body 101. Accordingly, the state in which the opening width between the first arm 12C and the second arm 13C of the arm member 11C is the first distance W1 is maintained. In other words, according to the present embodiment, the arm member 11C is restricted from being transitioned from the first open configuration to the second open configuration in the state where the pair of arm notches 18D, 23D are in contact with and locked by the step portion 15.

The operator uses the arm member 11C in the first open configuration to grasp and treat the target tissue T with the normal size by the same operations as the operations when using the endoscope clip 1 according to the first embodiment.

When the arm member 11C of the clip 10C according to the present embodiment is in the first open configuration, and the first distance W1 as the opening width between the first arm 12C and the second arm 13C is smaller than the size of the target tissue T, it is necessary for the operator to cause the arm member 11C to be transitioned from the first open configuration to the second open configuration to enlarge the opening width between the first arm 12C and the second arm 13C to the second distance W2 which is the maximum opening width.

At this time, the operator removes the limiting portion 64 provided at the proximal end side of the operation portion 100 of the endoscope clip 1A and then pushes the slider 102 toward the distal end side to move the arm member 11C to the distal end side and enlarge the opening width between the first arm 12C and the second arm 13C.

As shown in FIGS. 18A and 18B, when the arm member 11C moves toward the distal end side with respect to the pressing tube 31, the pair of arm notches 18D, 23D are elastically deformed and folded while contacting the step portion 15. That is, the arm member 11C may advance with respect to the pressing tube 31, and at the same time the pair of arm notches 18D, 23D may climb on and overcome the step portion 15. At this time, the first arm 12C and the second arm 13C of the arm member 11C are in contact with the tapered surface 31a at the distal end portion of the pressing tube 31 while the opening width between the first arm 12C and the second arm 13C is enlarged to a value larger than the first distance W1.

When the operator further pushes the slider 102, the pair of arm notches 18D, 23D may climb on and overcome the step portion 15 in a folded state. At this time, due to the elastically restoring force of the pair of arm notches 18D, 23D, the pair of arm notches may restore the initial shape as shown in FIG. 17B again.

As shown in FIG. 19, when the operator pushes the slider 102, in the state in which the slider 102 comes into contact with the distal end surface 101d of the slit 101b of the operation portion main body 101, it is impossible for the arm member 11C to further advance with respect to the pressing tube 31. That is, the first arm 12C and the second arm 13C of the arm member 11C are in the second open configuration in which the opening width therebetween is the second distance W2 as the maximum opening width.

In the present embodiment, by the operator removing the limiting portion 64 and pushing the slider 102 until the slider 102 comes in contact with the distal end surface 101d of the slit 101b of the operation portion main body 101, the arm member 11C of the clip 10C may be transitioned from the first open configuration to the second open configuration. In the arm member 11C transitioned to the second open configuration, the opening width between the first arm 12C and the second arm 13C is the second distance W2 that is larger than the first distance W1 such that it is possible to handle cases in which the size of the target tissues is large. As shown in FIG. 19, according to the endoscope clip 1C of the present embodiment, along the direction of the axis C1, the distance between the pair of arm notches 18D and 23D and the step portion 15 is smaller than the distance between the engaged portions 16, 17 or the second locked portions 21, 22 and the locking portion 32.

Subsequently, the operator may pull back the slider 102 to the proximal end side in a state of grasping the target tissue T using the endoscope clip 1C by the same operations as that according to the first embodiment. When the arm member 11C in the second open configuration moves to the proximal end side and climbs on and overcomes the step portion 15 from the distal end side, the proximal end portions of the pair of arm notches 18D, 23D are pressed. Accordingly, the pair of arm notches 18D, 23D are elastically deformed so as to approach the longitudinal direction of the first arm 12C and the second arm 13C, respectively. In this manner, the pair of arm notches 18D, 23D may smoothly overcome the step portion 15 from the distal end side without being caught by the step portion 15.

According to the endoscope clip 1C of the present embodiment, similar to the endoscope clip 1 according to the first embodiment, the treatment to the target tissue T having a size between the first distance W1 and the second distance W2 may be efficiently performed.

Fifth Embodiment

Hereinafter, an endoscope clip 1D according to the fifth embodiment of the present disclosure will be described with reference to FIGS. 20 and 21. Hereinafter, differences from the above-described embodiments will be mainly described. The same components as those of the endoscope clip according to each of the above-described embodiments are designated by the same reference numerals, and the description thereof will be omitted.

(Configuration of Endoscope Clip 1D)

Figure 20:
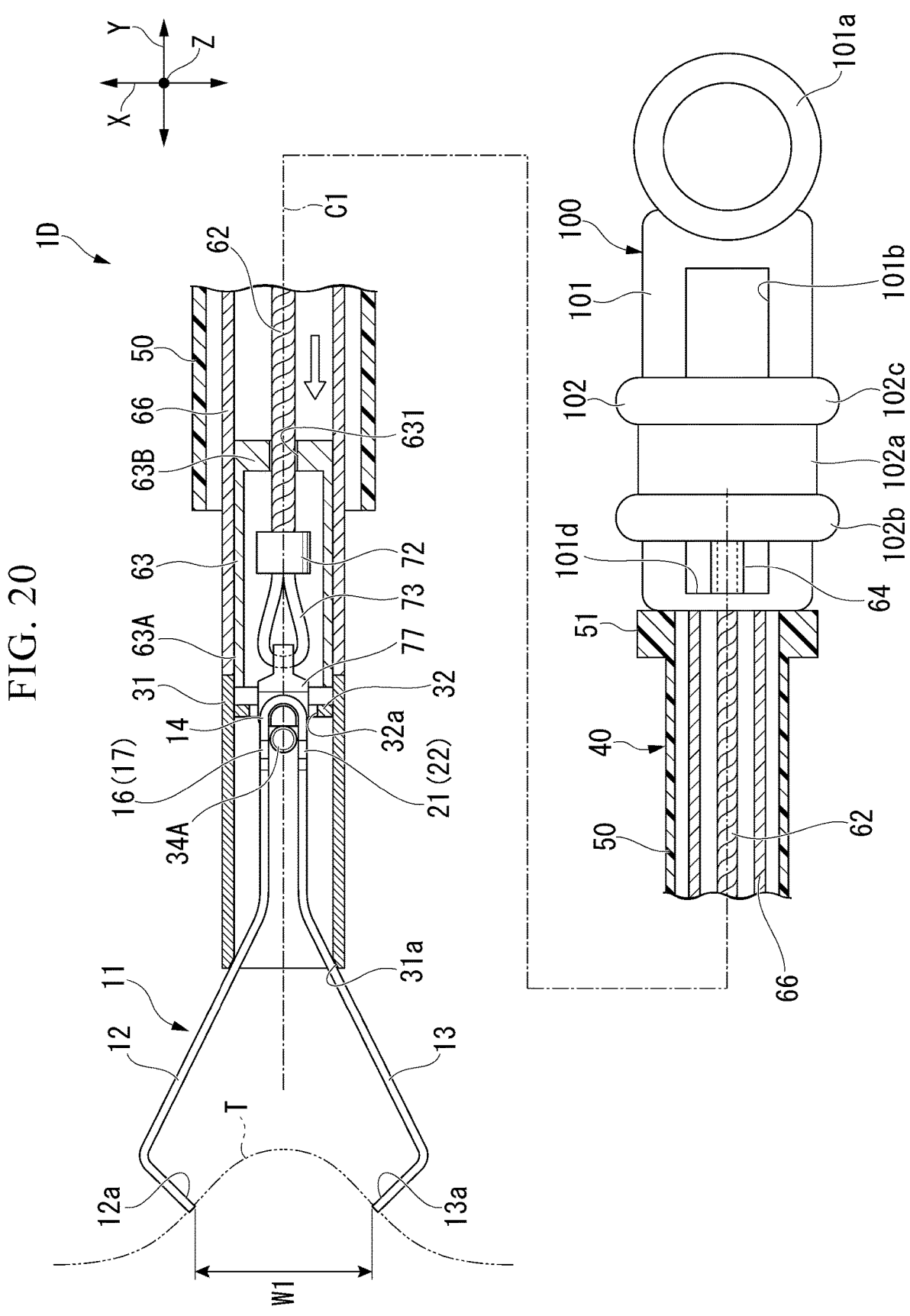
FIG. 20 is a cross-sectional side view schematically showing a configuration of an endoscope clip according to a fifth embodiment of the present disclosure.
Figure 21:
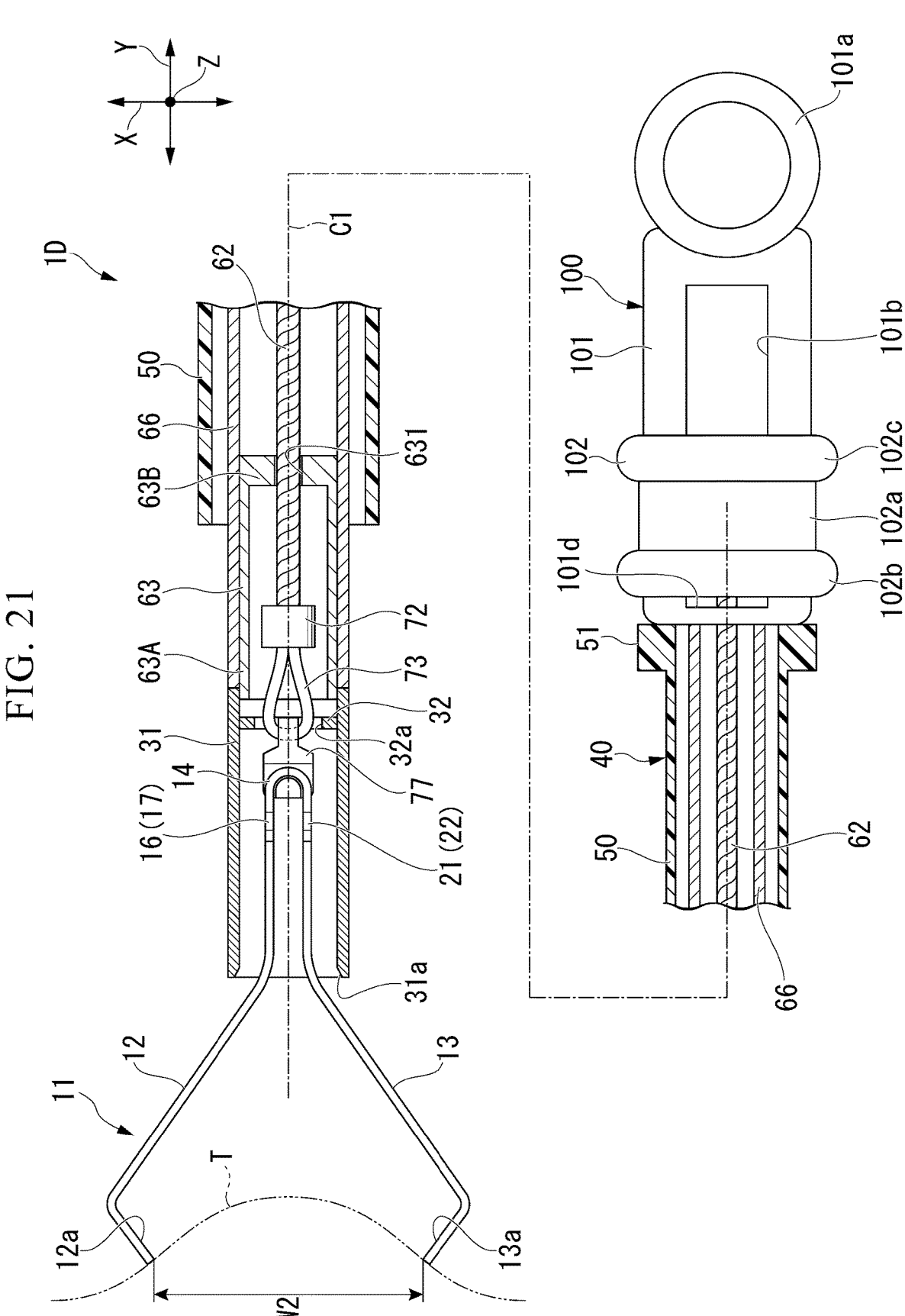
FIG. 21 is a cross-sectional side view showing the configuration of the endoscope clip according to the present embodiment.

FIG. 20 is a cross-sectional side view showing the first open configuration of the arm member 11 of the endoscope clip 1D according to the present embodiment. FIG. 21 is a cross-sectional side view showing a second open configuration of the arm member 11 of the endoscope clip 1D according to the present embodiment.

The endoscope clip 1D according to the present embodiment is different from the endoscope clip 1 according to the first embodiment in the configuration of the pressing tube 31 of the clip 10D.

As shown in FIG. 20, the endoscope clip 1D according to the present embodiment has a pin (engaging portion) 34A that inserts through the pressing tube 31 in a direction orthogonal to the axis C1 direction of the pressing tube 31.

In the cross-sectional side view shown in FIG. 20, the pin 34A is provided between the first arm 12 and the second arm 13. According to the present embodiment, when the pin 34A are inserted into the pressing tube 31 and the pin 34 and the pressing tube 31 are engaged with each other, the advancement of the arm member 11 with respect to the pressing tube 31 is restricted. The position where the pin 34A is arranged in the pressing tube 31 along the axis C1 direction of the pressing tube 31 is not particularly limited. For example, the pin 34A may be arranged on the proximal end side in the pressing tube 31.

Other configurations of the endoscope clip 1D according to the present embodiment are the same as those of the endoscope clip 1 according to the above-described first embodiment. That is, the endoscope clip 1D according to the present embodiment may include the operation portion 100 having the operation portion main body (handle) 101, the slider 102, and the limiting portion 64.

(Operation of Endoscope Clip 1D)

Hereinafter, the operation of the endoscope clip 1D according to the present embodiment will be described, focusing on the process in which the arm member 11 of the endoscope clip 1D according to the present embodiment is transitioned from the first open configuration to the second open configuration.

As shown in FIG. 20, when the pin 34A is inserted into the pressing tube 31, the distal end surface of the slider 102 of the operation portion 100 at the proximal end side is in contact with the proximal end surface of the limiting portion 64. Inside the connection member 63, the enlarged diameter portion 72 is located apart from the proximal end portion 63B of the connection member 63 and located at the distal end side more than the proximal end portion 63B.

In this state, due to the elastic restoring force of the first arm 12 and the second arm 13, the arm member 11 is biased in a direction of protruding from the pressing tube 31. However, since the pin 34A is inserted through the pressing tube 31, the arm member 11 is impossible to move toward the distal end side beyond the range restricted by the pin 34A. Accordingly, the first arm 12 and the second arm 13 of the arm member 11 come into contact with the tapered surface 31a of the distal end portion of the pressing tube 31, and the opening width between the first arm 12 and the second arm 13 is the first distance W1.

According to the present embodiment, as shown in FIG. 20, the slider 102 comes into contact with the limiting portion 64 and is located at the most distal position with respect to the operation portion main body 101, that is, the neutral position. When the slider 102 is in the neutral position, the operation wire 62 connected to the slider 102 and the arm member 11 connected to the operation wire 62 are also in a state in which they are impossible to be advanced with respect to the operation portion main body 101. Accordingly, the state in which the opening width between the first arm 12 and the second arm 13 of the arm member 11 is the first distance W1 is maintained. In other words, according to the present embodiment, the pin 34A is inserted into the pressing tube 31 and the pin 34A and the pressing tube 31 are engaged with each other, such that the transition of the arm member 11 from the first open configuration to the second open configuration is restricted.

The operator may use the arm member 11 in the first open configuration to grasp and treat the target tissue T by the same operations as the operations using the endoscope clip 1 according to the first embodiment.

In the endoscope clip 1 according to the above-described first embodiment, the operator may rotate the arm member 11 with respect to the pressing tube 31 by operating the operation wire 62. Compared to this, in the endoscope clip 1D according to the present embodiment, since the arm member 11 and the pressing tube 31 are connected by the pin 34A, the arm member 11 and the pressing tube 31 may be integrally rotated.

According to the present embodiment, at the time of treating the target tissue T having a size larger than the normal size, it is necessary to enlarge the opening width between the first arm 12 and the second arm 13 to be equal to or larger than the first distance W1. At this time, as shown in FIG. 21, the operator removes both the limiting portion 64 and the pin 34A provided on the operation portion 100 at the proximal end side of the endoscope clip 1D, and then pushes the slider 102 toward the distal end side so as to move the arm member 11 to the distal end side by the transmission of the operation wire 62. According to the present embodiment, the pin 34A may be once removed from the pressing tube 31 and then inserted again into the pressing tube 31.

In this state, the operator may move the operation wire 62 and the arm member 11 connected to the operation wire 62 to the position at the most distal end side by continuously pushing the slider 102 until the slider 102 comes into contact with the distal end surface 101d of the slit 101b of the operation portion main body 101. At this time, the opening width between the first arm 12 and the second arm 13 of the arm member 11 becomes the second distance W2 as the maximum opening width. That is, the arm member 11 of the endoscope clip 1D may be transitioned from the first open configuration to the second open configuration similar to the first embodiment.

According to the present embodiment, since the opening width between the first arm 12 and the second arm 13 in the arm member 11 that has transitioned to the second open mode is the second distance W2 which is larger than the first distance W1, it is possible to handle cases in which the size of the target tissue is large.

Subsequently, the operator may use the arm member 11 in the second open configuration to grasp and treat the target tissue T by the same operations as the operations using the endoscope clip 1 according to the above-described first embodiment.

According to the endoscope clip 1D according to the present embodiment, the opening width between the first arm 12 and the second arm 13 of the arm member 11 may be changed in stages. As a result, similar to the endoscope clip 1 according to the first embodiment, it is possible to efficiently treat the target tissue T having a size between the first distance W1 and the second distance W2.

Sixth Embodiment

Hereinafter, an endoscope clip 1E according to a sixth embodiment of the present disclosure will be described below with reference from FIGS. 22A to 32. Hereinafter, differences from the above-described embodiments will be mainly described. The same configurations as those of the endoscope clip according to each of the above-described embodiments are designated by the same reference numerals, and the description thereof will be omitted.

Figure 22A:
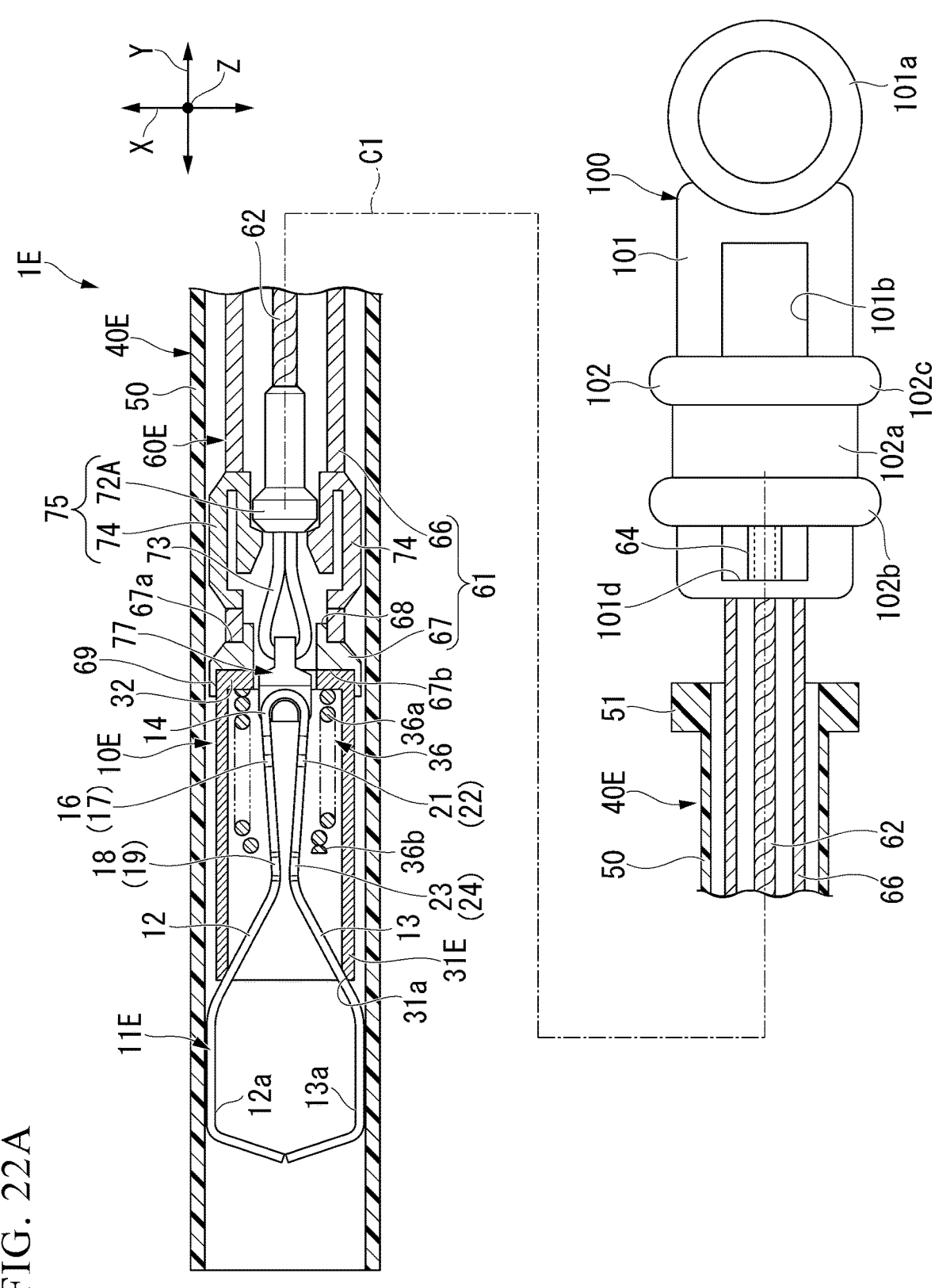
FIG. 22A is a cross-sectional side view schematically showing a configuration of an endoscope clip according to a sixth embodiment of the present disclosure.
Figure 22B:
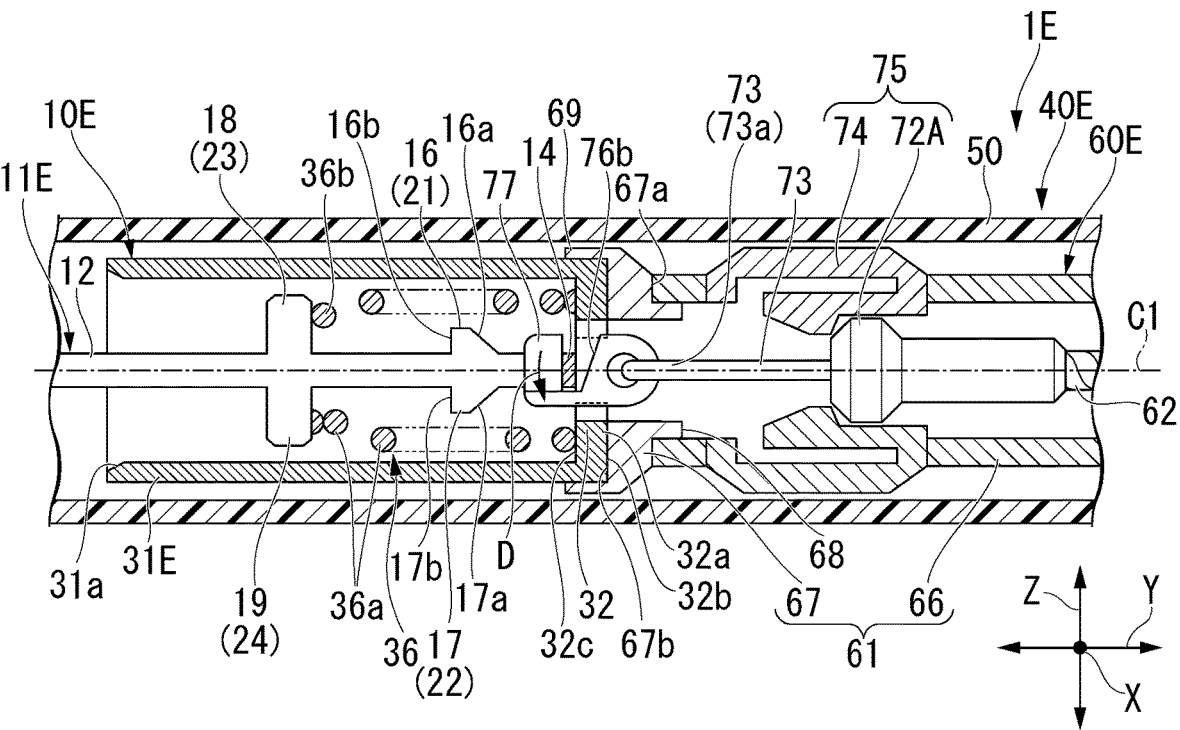
FIG. 22B is a cross-sectional planar view schematically showing a configuration of the distal end portion of the endoscope clip according to the present embodiment.
Figure 23:
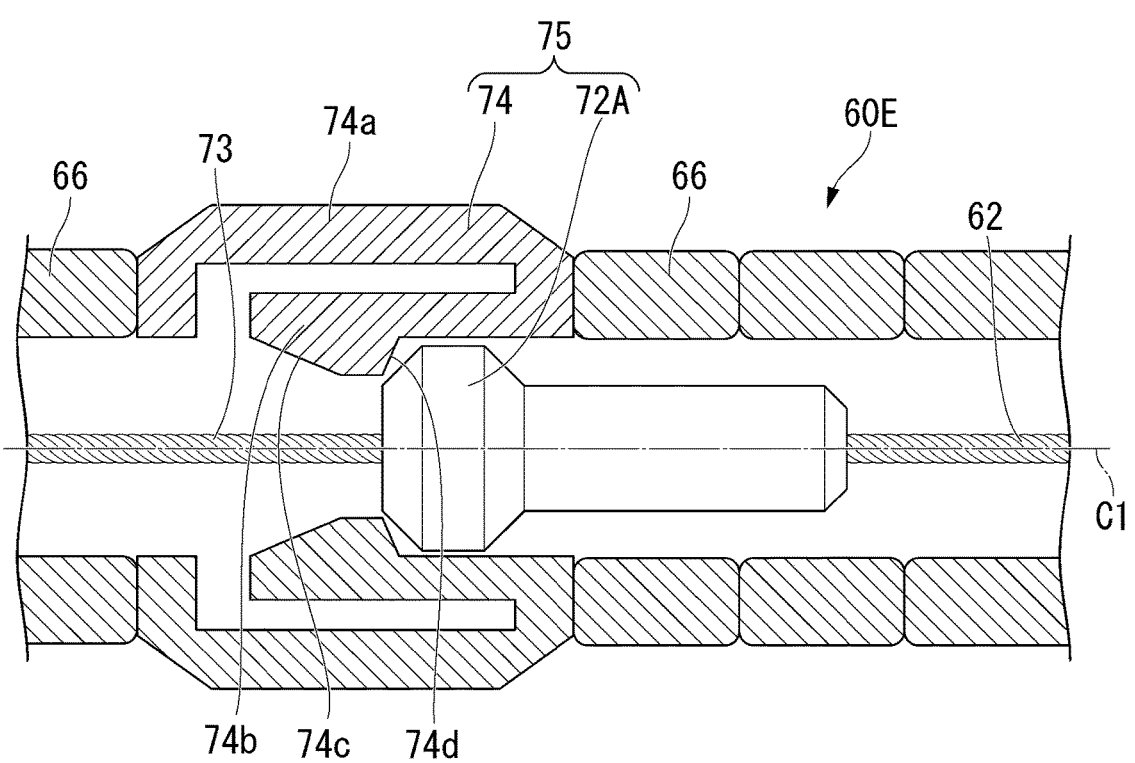
FIG. 23 is a cross-sectional side view schematically showing a configuration of part of the endoscope clip according to the present embodiment.
Figure 24:
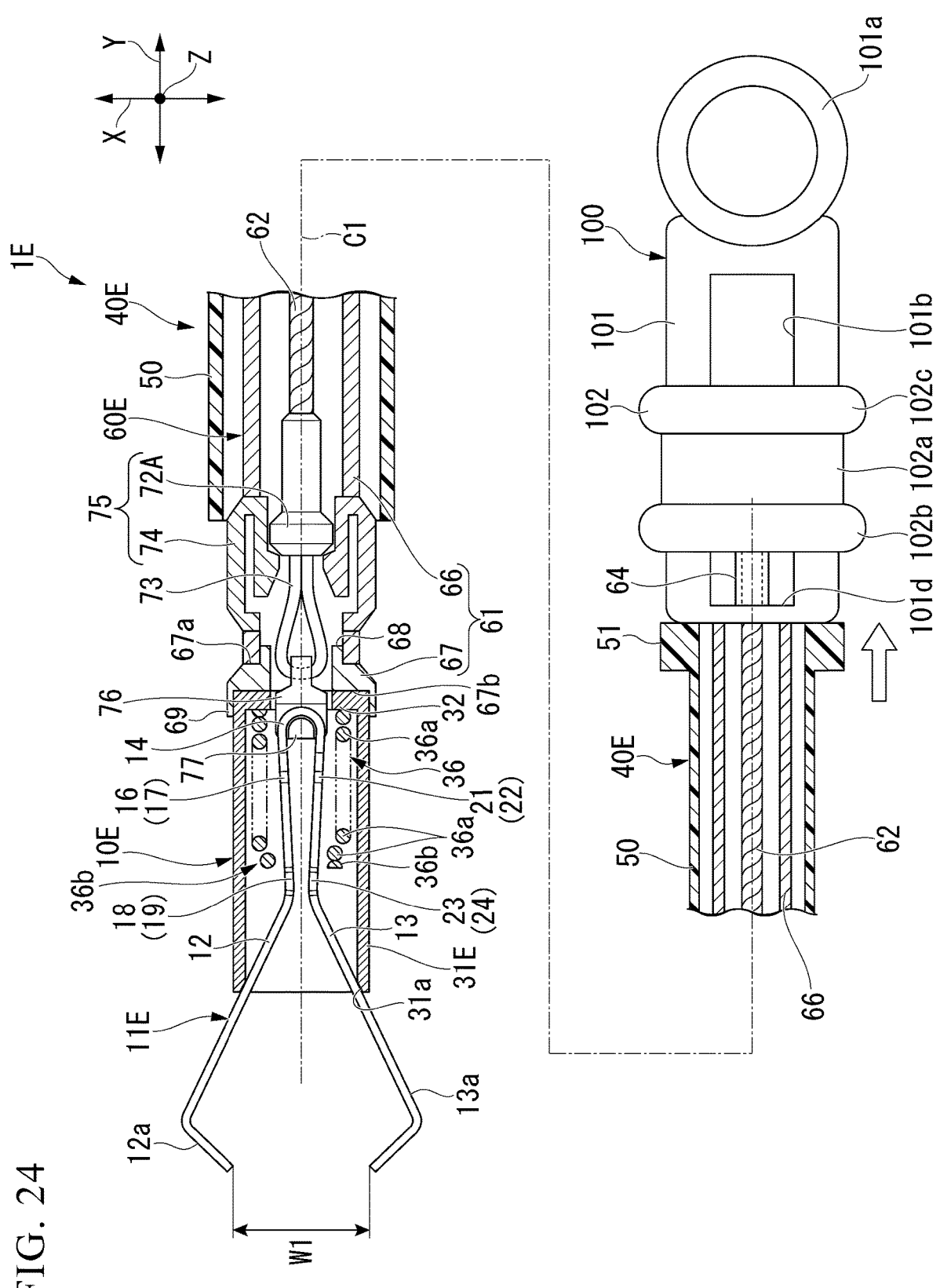
FIG. 24 is a cross-sectional side view schematically showing the configuration of the endoscope clip according to the present embodiment.
Figure 25:
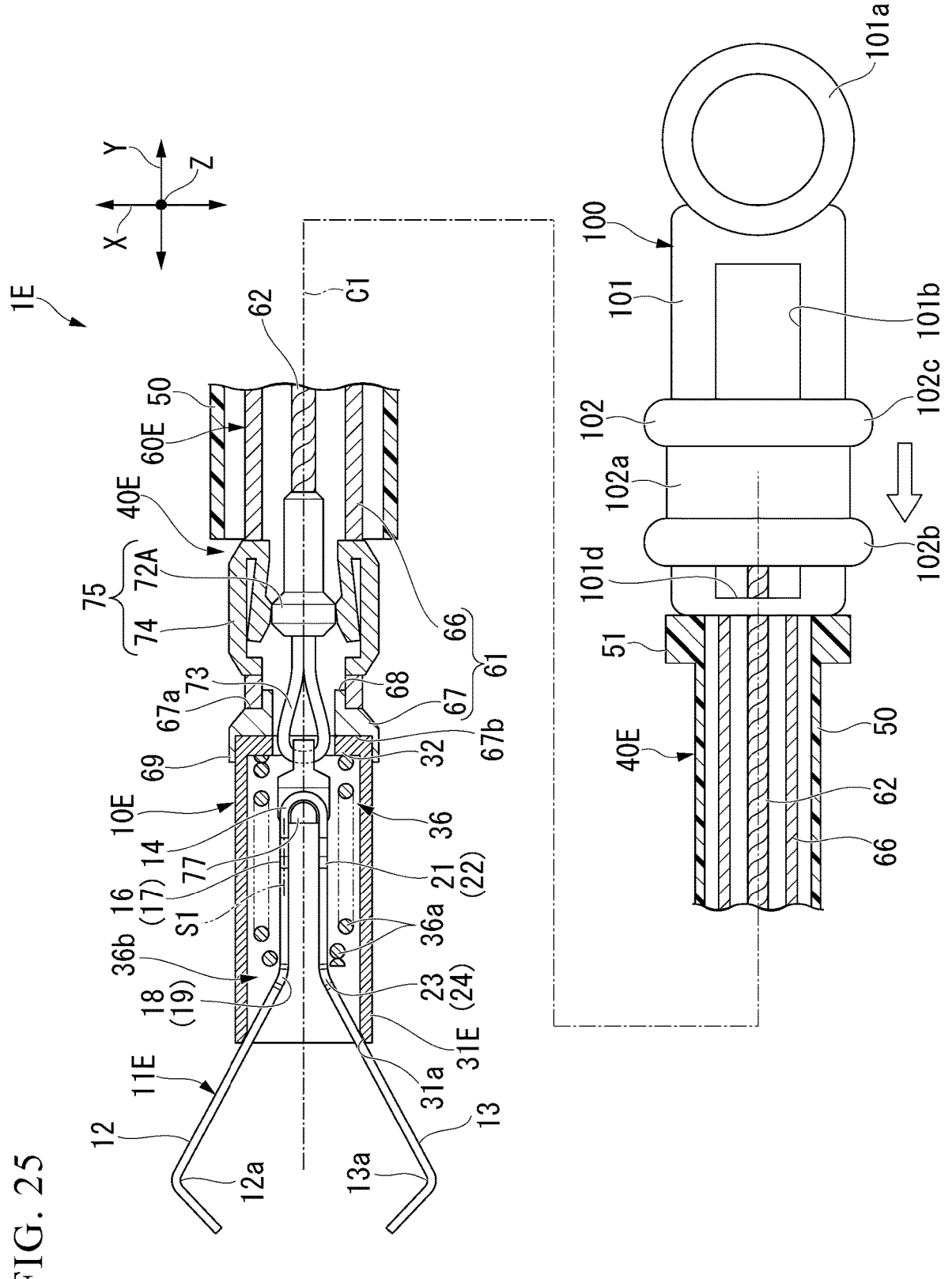
FIG. 25 is a cross-sectional side view schematically showing the configuration of the endoscope clip according to the present embodiment.
Figure 26:
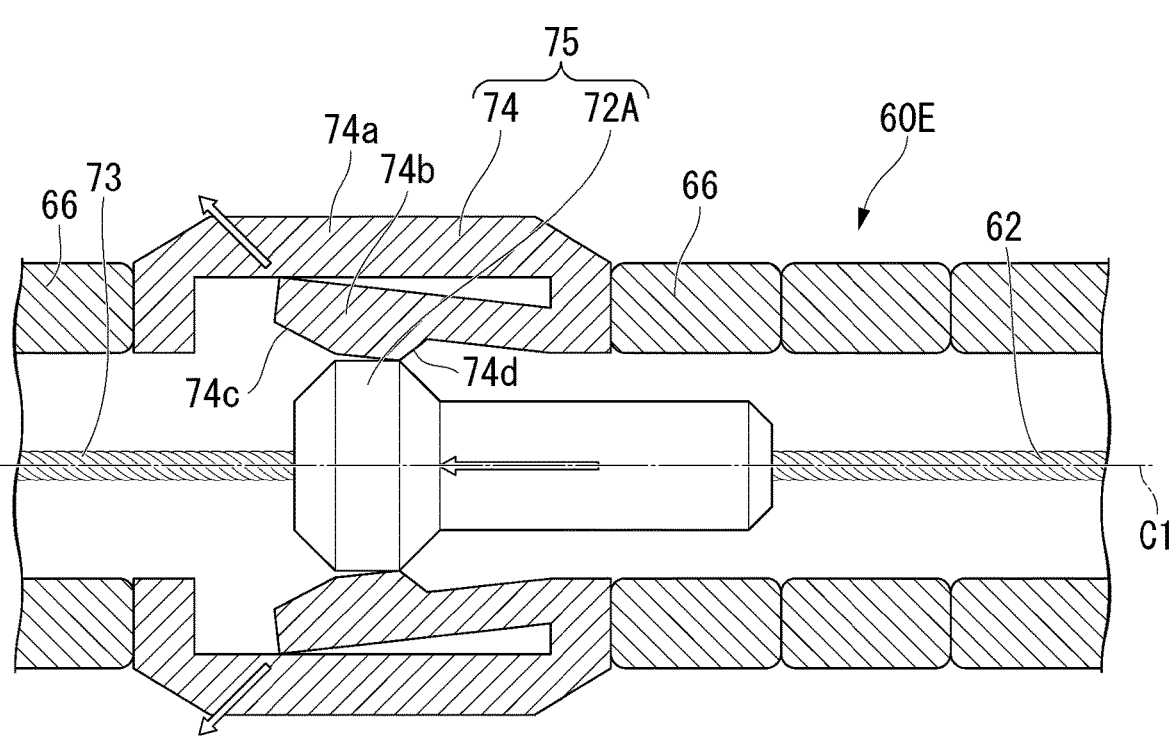
FIG. 26 is a cross-sectional side view schematically showing the configuration of part of the endoscope clip according to the present embodiment.
Figure 27:
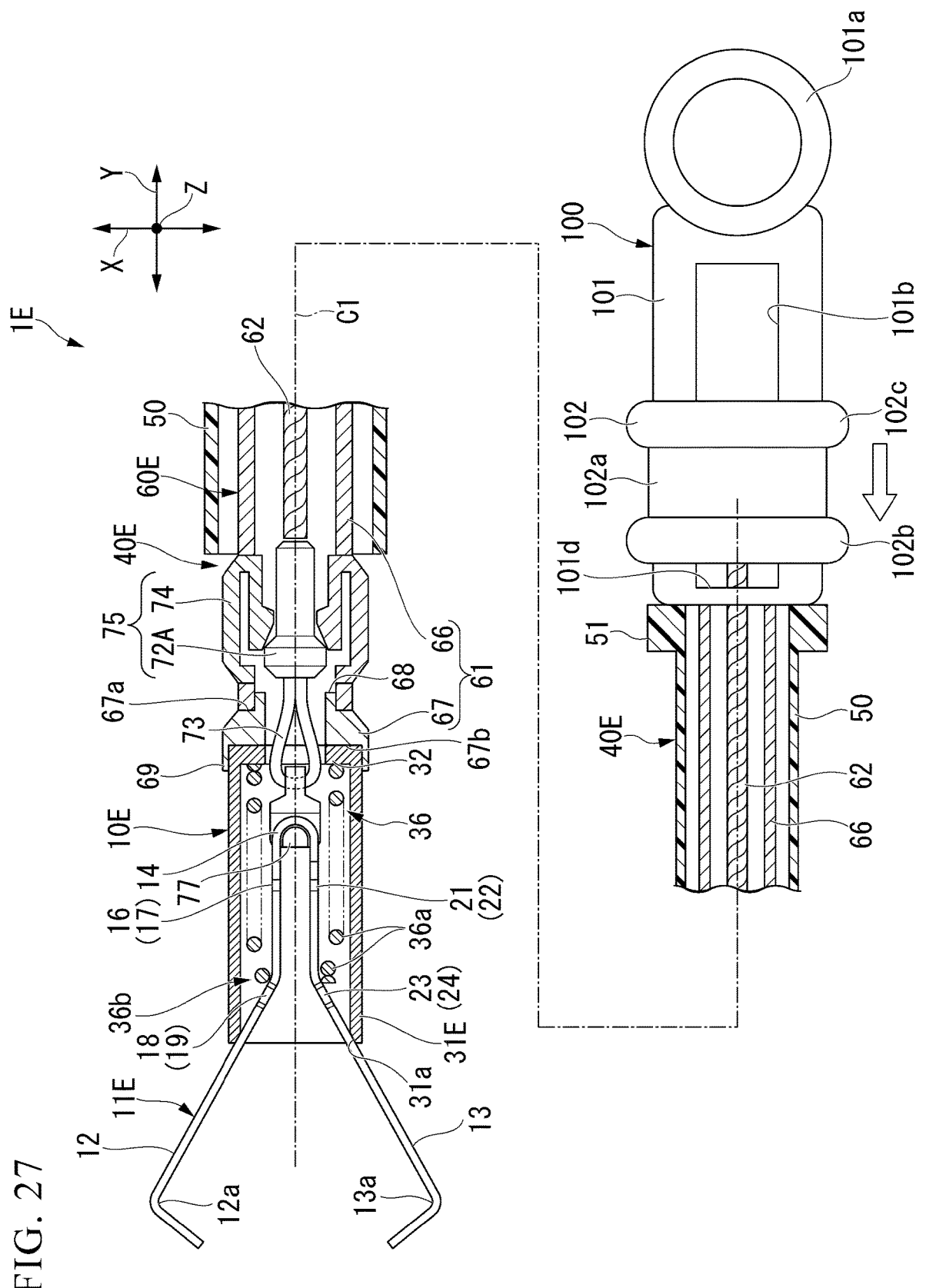
FIG. 27 is a cross-sectional side view schematically showing the configuration of the endoscope clip according to the present embodiment.
Figure 28:
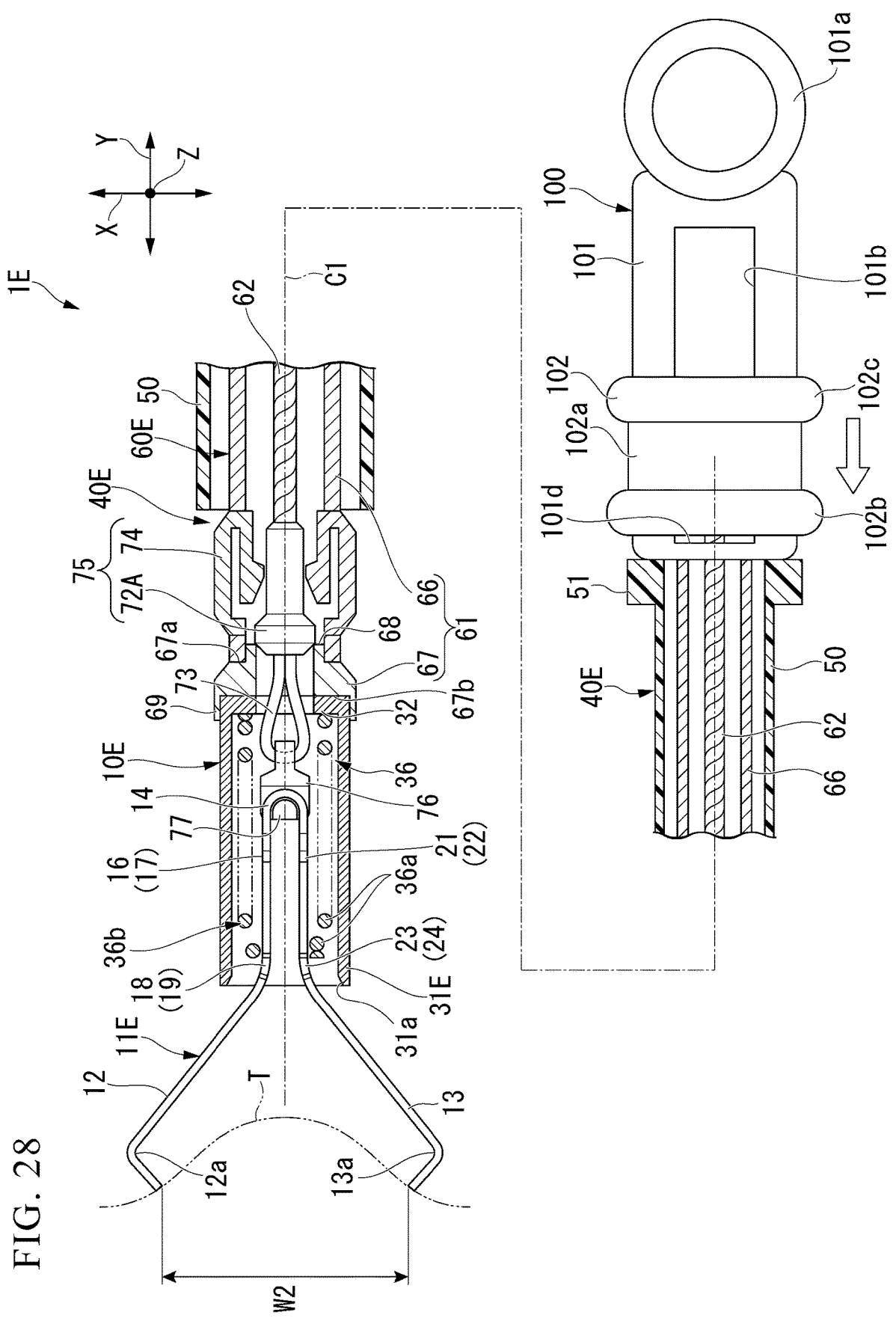
FIG. 28 is a cross-sectional side view schematically showing the configuration of the endoscope clip according to the present embodiment.
Figure 29:
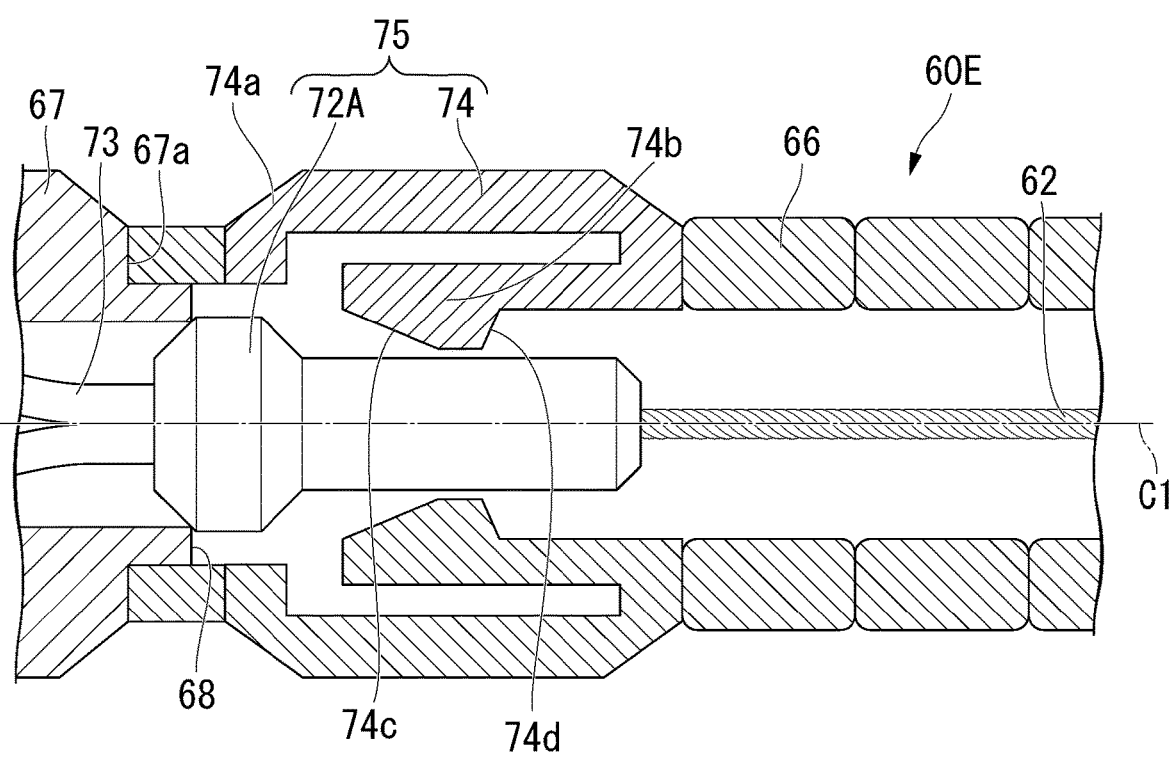
FIG. 29 is a cross-sectional side view schematically showing the configuration of part of the endoscope clip according to the present embodiment.
Figure 30:
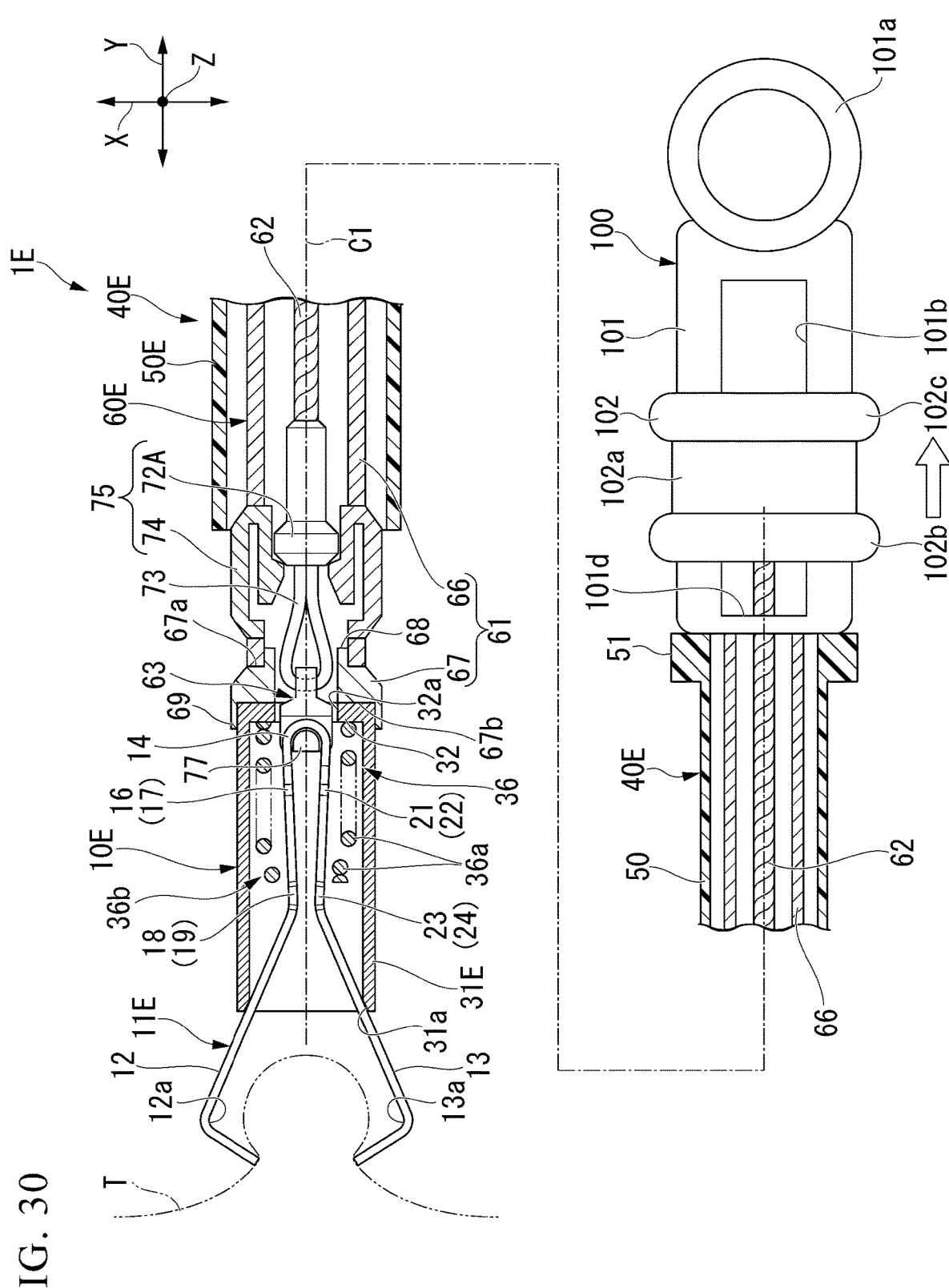
FIG. 30 is a cross-sectional side view schematically showing the configuration of the endoscope clip according to the present embodiment.
Figure 31A:
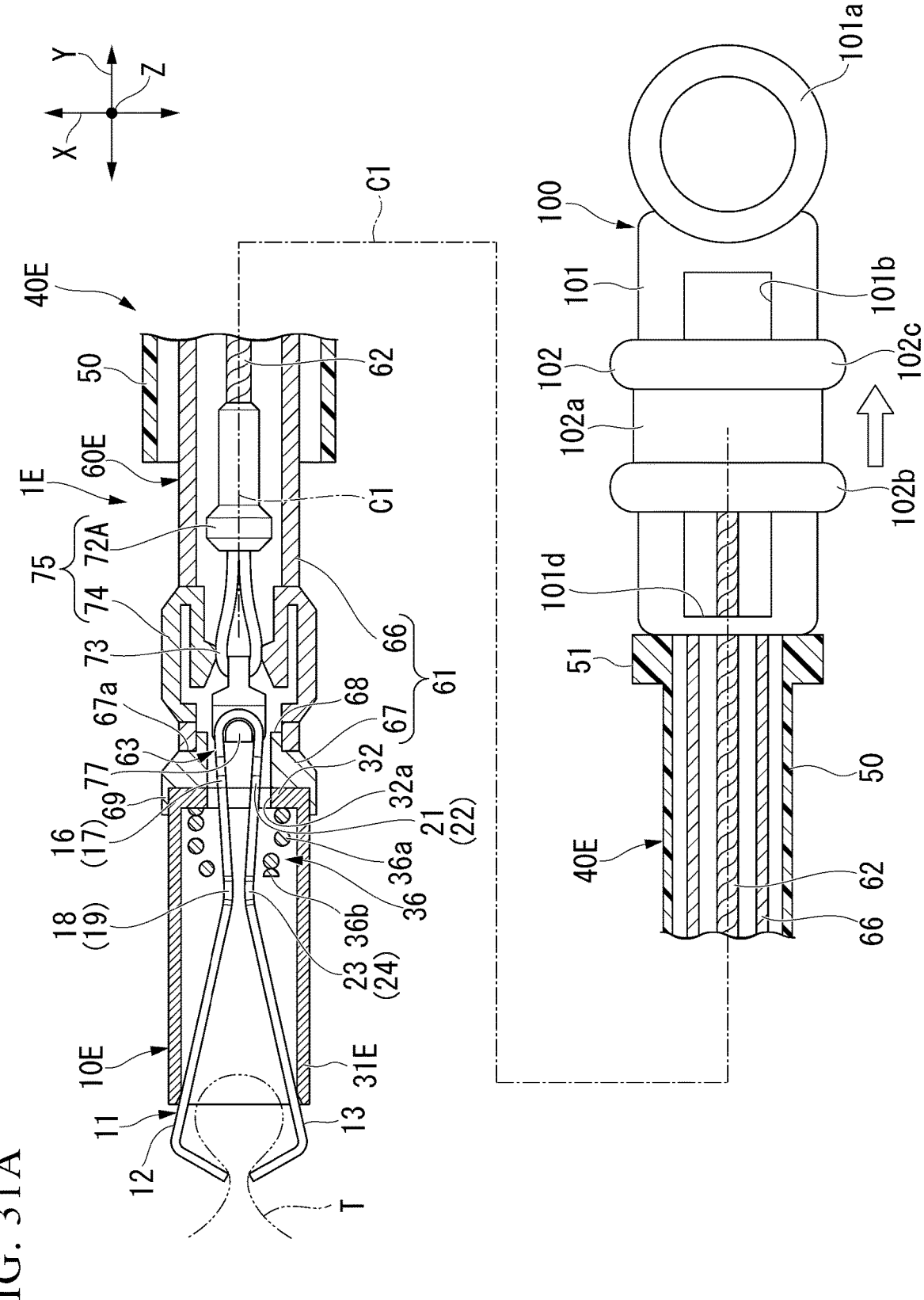
FIG. 31A is a cross-sectional side view schematically showing the configuration of the endoscope clip according to the present embodiment.
Figure 31B:
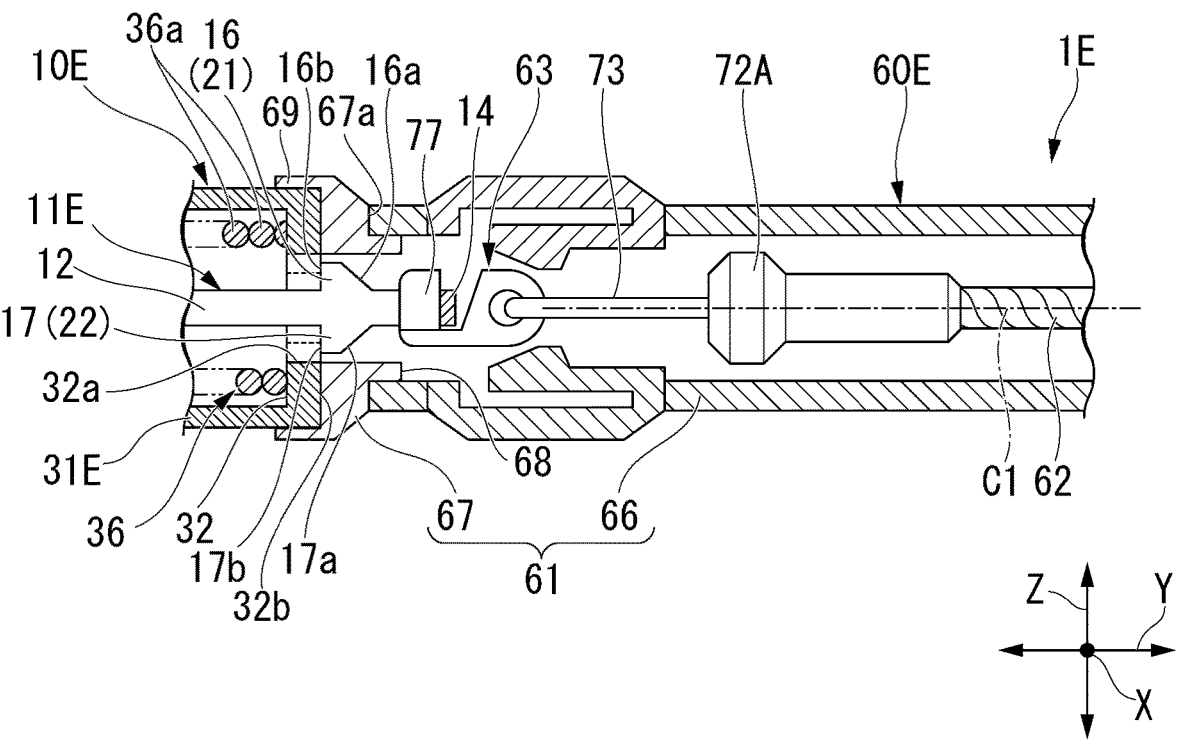
FIG. 31B is a cross-sectional side view schematically showing the configuration of part of the endoscope clip according to the present embodiment.
Figure 32:
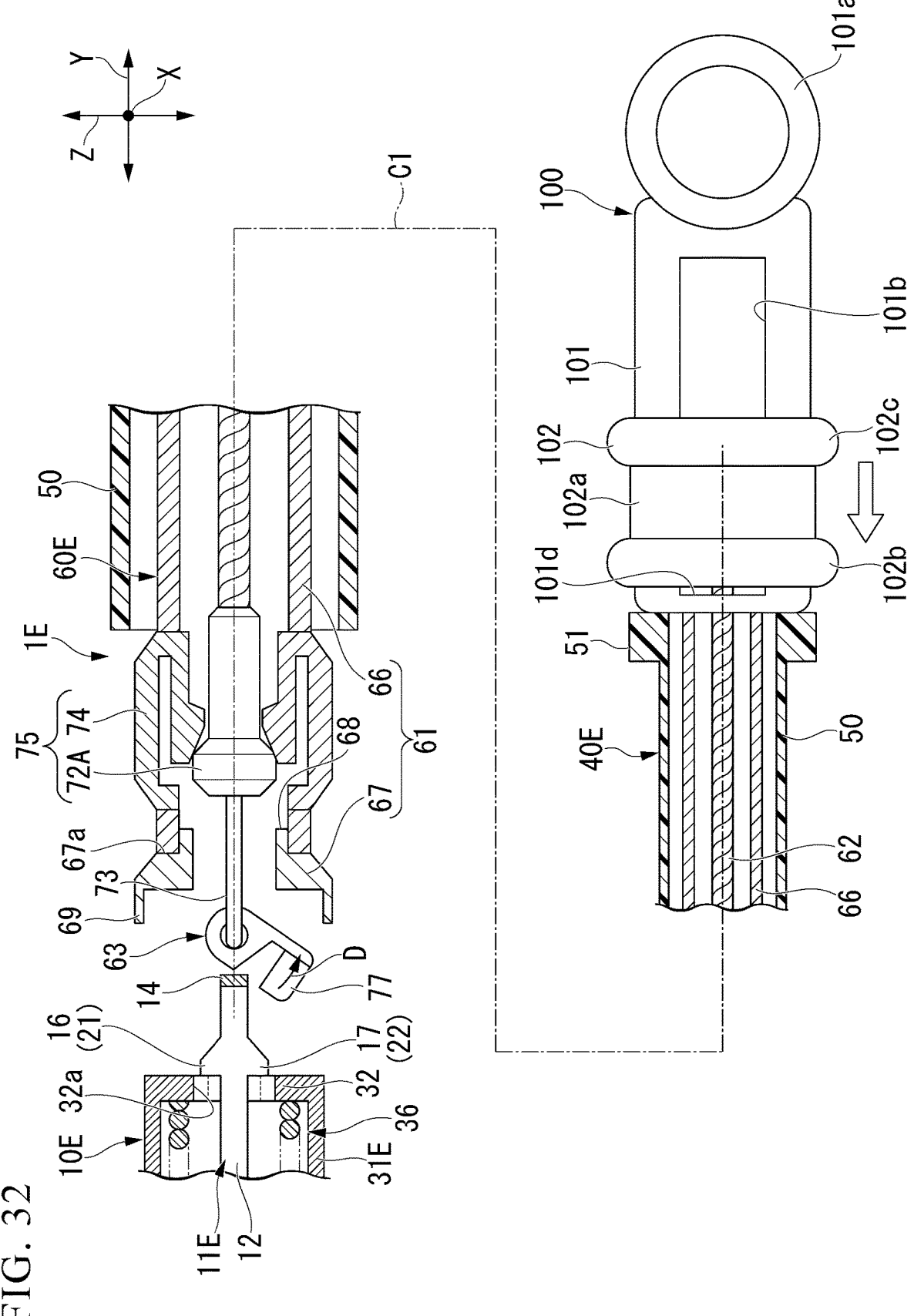
FIG. 32 is a cross-sectional side view schematically showing the configuration of the endoscope clip according to the present embodiment.

FIG. 22A is a cross-sectional side view showing an initial state of the endoscope clip 1E according to the present embodiment. FIG. 22B is a cross-sectional planar view showing the configuration of the distal end portion when the endoscope clip 1E according to the present embodiment is in the initial state. FIG. 23 is an enlarged cross-sectional view showing the configuration of the restriction portion 75 of the endoscope clip 1E according to the present embodiment. FIG. 24 is a cross-sectional side view showing the first open configuration of the endoscope clip 1E according to the present embodiment. FIG. 25 is a cross-sectional side view showing the operation of the endoscope clip 1E. FIG. 26 is an enlarged cross-sectional view showing a state of the restriction portion 75 of the endoscope clip 1E in FIG. 25. FIG. 27 is a cross-sectional side view showing the operation of the endoscope clip 1E. FIG. 28 is a cross-sectional side view showing the second open configuration of the endoscope clip 1E. FIG. 29 is an enlarged cross-sectional view showing the state of the restriction portion 75 of the endoscope clip 1E in FIG. 28. FIG. 30 is a cross-sectional side view showing the operation of the endoscope clip 1E. FIG. 31A is a cross-sectional side view showing an engagement state of the endoscope clip 1E. FIG. 31B is a cross-sectional side view showing the state of the distal end side of the endoscope clip 1E in FIG. 31A. FIG. 32 is a cross-sectional side view showing a release state of the endoscope clip 1E.

As shown in FIG. 22A, the endoscope clip 1E according to the present embodiment includes a clip unit (hereinafter, simply referred to as "clip") 10E and a treatment tool main body (applicator) 40E. The clip 10E is detachably connected to the distal end portion of the treatment tool main body 40E. The clip 10E includes an arm member 11E, a pressing tube 31E, and an elastic member (a spiral spring) 36. The treatment tool main body 40E includes an outer sheath 50, an insertion portion 60E, and an operation portion 100.

Similar to the above-described embodiments, the endoscope clip 1E according to the present embodiment has the limiting portion disposed in the operation portion of the endoscope clip, while restriction portion 75 configured to restrict the movement of the operation wire 62 toward the distal end side is disposed in the insertion portion 60E.
(Configuration of Restriction Unit 75)

As shown in FIGS. 22A to 23, in the insertion portion 60E of the endoscope clip 1E according to the present embodiment, the restriction portion 75 configured from the stopper 72 and the fixing member 74 is provided. The stopper 72 is referred to as an engaged portion of the restriction portion 75, and the fixing member 74 is referred to as an engaging portion of the restriction portion 75.

As shown in FIGS. 22A and 22B, in the state in which the stopper 72 is positioned at the proximal end side more than the fixing member 74 and the operator does not grasp the slider 102, the stopper 72 is biased toward the distal end side and in contact (engage) with the fixing member 74 due to the elastic force of the elastic member 36 disposed in the pressing tube 31E.
(Configuration of Stopper 72)

The stopper 72 is configured to be connected to the distal end of the operation wire 62. According to the present embodiment, the stopper 72 may advance and retract together with the operation wire 62. The loop portion 73 and the hook 77 are connected to the distal end portion of the stopper 72.

The stopper 72 is formed of, for example, metal in a cylindrical shape. The outer diameter of the stopper 72 is smaller than the inner diameter of the coil sheath 66 and larger than the inner diameter of a distal member 67. As described above, the outer diameter of the stopper 72 is larger than the width of the inner cavity formed inside the fixing member 74. The stopper 72 may have a distal end surface and a proximal end surface along the axial direction Y that are formed in a tapered shape.

According to the present embodiment, since the stopper 72 has the above-described configuration, in the state in which the operation force by the operator is not applied, due to the elastic force of the elastic member 36 provided in the pressing tube 31E, the stopper 72 may be biased toward the distal end side and engaged with the fixing member 74. When the operator pushes the slider 102 of the operation section 100, the stopper 72 may move to the distal end side and overcome the fixing member 74. When the operator pushes the slider 102 of the operation section 100 and the stopper 72 comes in contact with the step portion 68 of the distal member 67, the arm member 11E of the clip 10E may be transitioned to the second open configuration that the opening width between the first arm 12 and the second arm 13 is the maximum value.
(Configuration of Fixing Member 74)

As shown in FIG. 22A, the fixing member (engaged portion of the restriction portion) 74 is provided on the inner circumferential surface on the distal end side of the sheath 61 and protrudes toward the axis C1. For example, the fixing member 74 may be fixed by welding the distal end and the proximal end along the axial direction Y to the strand wire forming the coil sheath 66. The fixing member 74 may be formed integrally with the coil sheath 66.

However, the configuration of the fixing member 74 is not limited thereto. For example, the fixing member 74 may be fixed by welding, bonding or the like to the inner circumferential surface at the distal end side of the coil sheath 66 formed by tightly winding the strand in the axial direction Y. The fixing member 74 is not limited to the example configured by being sandwiched between the strand wires forming the coil sheath 66 as shown in FIG. 23. For example, the fixing member 74 may be arranged at the distal end side more than the coil sheath 66, and the proximal end of the fixing member 74 along the axial direction Y may fixed to the strand forming the coil sheath 66 by a method such as welding, bonding or the like. According to the present embodiment, the material forming the fixing member 74 is not particularly limited. For example, in order to ensure durability, the fixing member 74 may be formed of the same metal material as that of the pressing tube 31E.

As shown in FIG. 23, the fixing member 74 according to the present embodiment has a support portion 74a and a deforming portion 74b. The support portion 74a is formed radially outward of the deforming portion 74b with respect to the axis C1. The strand wire forming the coil sheath 66 is fixed to the distal end and the proximal end of the support portion 74a.

The deforming portion 74b has a proximal end portion connected to the proximal end portion of the support portion 74a, and a portion disposed on the distal end side more than the proximal end portion is formed to be separated from the support portion 74a by a certain distance from the support portion 74a. That is, the deforming portion 74b forms a gap with the support portion 74a at the certain distance outwardly in the radial direction with respect to the axis C1.

The outer diameter of the fixing member 74 is defined by the maximum width of the support portion 74a in the radial direction orthogonal to the central axis C1. According to the present embodiment, the outer diameter of the fixing member 74 may be slightly larger than the outer diameter of the coil sheath 66, for example.

As shown in FIG. 23, at least a part of the deforming portion 74b of the fixing member 74 is formed to protrude toward the axis C1. In other words, at least apart of the deforming portion 74b of the fixing member 74 is formed to protrude inwardly in the radial direction around the axis C1. The deforming portion 74b is configured by a pair of claws that are arranged at positions opposite to each other with the axis C1 sandwiched therebetween. A distance between the pair of claws (that is, the width of the space between the pair of claws) is smaller than the inner diameter of the coil sheath 66 and the outer diameter of the stopper 72. In other words, the fixing member 74 has an inner cavity with a width smaller than the inner diameter of the coil sheath 66 and the outer diameter of the stopper 72 described below.

According to the present embodiment, an example in which the deforming portion 74*b* is configured by a pair of claws has been described; however, the present disclosure is not limited thereto. For example, the deforming portion 74*b* may be configured by a single claw. In this case, the width of the inner cavity of the fixing member 74 (the inner cavity having a width smaller than the inner diameter of the coil sheath 66 and the outer diameter of the stopper 72 described later) is defined by the single claw. As shown in FIG. 23, the deforming portion 74*b* of the fixing member 74 has a distal end 74*c* and a proximal end 74*d* formed as an inclined surface so as to engage with the stopper 72 described below.

The deforming portion 74*b* may be elastically deformed by rotating outwardly in the radial direction with the connection portion between the supporting portion 74*a* and the deforming portion 74*b* as a fulcrum by the operator pushing the slider 102 of the operation portion 100 to cause the deforming portion 74*b* to be pressed by the stopper 72 in a state in which the fixing member 74 and the stopper 72 are in contact (engaged).

According to the present embodiment, it is preferable that the fixing member 74 is disposed at the proximal end side more than the elastic member 36 disposed inside the pressing tube 31E. More preferably, the fixing member 74 of the restriction portion 75 is disposed at a position at the proximal end side more than the distal end opening of the sheath 61. For example, according to the present embodiment, the fixing member 74 of the restriction portion 75 may be arranged at a position within about 1 centimeter from the distal end opening of the sheath 61 toward the proximal end side. On the other hand, as described above, the stopper 72 of the restriction portion 75 may move to the distal end side until the stopper 72 comes into contact with the step portion 68 formed at the proximal end side of the distal member 67.

By disposing the fixing member 74 of the restriction portion 75 in this manner, the distance between the position where the stopper 72 engages with the fixing member 74 and the position of the arm member 11E becomes smaller. Since the endoscope clip 1E according to the present embodiment has such a configuration, even when the endoscope clip 1E is inserted into the luminous cavity having a complicated shape and the coil sheath 66 of the sheath 61 is meandering, a change in the path length between the stopper 72 and the arm member 11E may be suppressed. As a result, the first open configuration of the arm member 11E may be more reliably maintained by the engagement of the fixing member 74 and the stopper 72.

(Configuration of Clip 10E)

As shown in FIGS. 22A and 22B, the clip 10E according to the present embodiment is different from the above-described embodiments in that the elastic member 36 is provided inside the pressing tube 31E.

(Configuration of Elastic Member 36)

An end turn portion 36*b* is provided at the distal end portion of the elastic member 36. The end turn portion 36*b* is formed to have an inner diameter smaller than that of the other portion of the elastic member 36. In a state in which the elastic member 36 is accommodated in the pressing tube 31E, a distal end portion thereof is locked by the protrusions 18, 19, 23, 24 and a proximal end portion thereof is locked by the locking portion 32. The proximal end portion of the elastic member 36 and the locking portion 32 may be fixed by welding or the like.

A portion of the first arm 12 at the proximal end more than the protrusions 18 and 19, a portion of the second arm 13 at the proximal end more than the protrusions 23 and 24, and the central portion 14 may be inserted into the elastic member 36.

According to the present embodiment, when the protrusions 18, 19, 23, 24 move to the proximal end side, the protrusions 18, 19, 23, 24 are locked by the end turn portion 36*b* of the elastic member 36. When the protrusions 18, 19, 23, 24 move to the proximal end side, the elastic member 36 is compressed by the protrusions 18, 19, 23, 24 in the axial direction Y. When the elastic member 36 is compressed, an elastic force that pushes the arm member 11E from the pressing tube 31E in the axial direction Y is generated. Even when the elastic member 36 does not include the end turn portion 36*b*, the same effect can be achieved by attaching another member such as a washer or the like to the distal end of the elastic member 36.

(Configuration of Arm Member 11E)

According to the present embodiment, two protrusions 18, 19 are provided on the distal end side of the first locked portions 16, 17 of the first arm 12. As shown in FIG. 22B, the protrusions 18, 19 protrude from the lateral surface of the first arm 12 in the orthogonal direction Z. According to the present embodiment, the protrusion 18 and the protrusion 19 may be line-symmetric with respect to the axis C1 in the planar view of FIG. 22B. The length by which the protrusions 18, 19 protrude from the first arm 12 may be longer than the length by which the first locked portions 16, 17 protrude from the first arm 12 in the orthogonal direction Z.

Similar to the first locked portions 16, 17 and the protrusions 18, 19 disposed in the first arm 12, the second locked portions 21, 22 and protrusions 23, 24 are formed in the second arm 13. The first arm 12 and the second arm 13 of the arm member 11E have an elastic restoring force such that the distal ends thereof are separated from each other, that is, the direction in which the arm member 11E opens.

(Configuration of Locking Portion 32)

As shown in FIGS. 22A and 22B, the locking portion 32 is formed to protrude over the entire circumference on the inner wall of the proximal end portion of the pressing tube 31E. The edge portion 32*a* of the locking portion 32 at the axis C1 side is formed in a circular shape (not shown) coaxial with the pressing tube 31E. As shown in FIG. 22B, the proximal end surface 32*b* (proximal end side end surface) and the distal end surface 32*c* (distal end side end surface) of the locking portion 32 are orthogonal to the axial direction Y. A portion of the first arm 12 at the proximal end side more than the protrusions 18, 19, a portion of the second arm 13 at the proximal end side more than the protrusions 23, 24, and the central portion 14 are inserted into the locking portion 32.

(Configuration of Treatment Tool Body 40E)

The treatment tool main body 40E according to the present embodiment is different from the above-described embodiments both in that the above-described restriction portion 75 is included and in the connection embodiment of the treatment tool main body 40E and the clip 10E. More specifically, the treatment tool main body 40E according to the present embodiment is provided with the distal member 67 for supporting the pressing tube 31E of the clip 10E at the distal end side.

(Configuration of Distal Member 67)

According to the present embodiment, for example, the distal member 67 may be formed of stainless steel in a cylindrical shape. The inner diameter of the distal member 67 is smaller than the inner diameter of the coil sheath 66. The outer diameter of the distal member 67 is larger than the outer diameter of the coil sheath 66 and the pressing tube 31E. On the outer circumferential surface of the proximal end portion of the distal member 67, a concave portion 67a is formed by reducing the outer diameter thereof. The distal member 67 and the coil sheath 66 are fixed by laser welding or the like with the distal end of the coil sheath 66 engaged with the concave portion 67a.

On the inner circumferential surface of the distal end portion of the sheath 61, a step portion 68 is formed in the connecting portion between the coil sheath 66 and the distal member 67 by reducing the inner diameter of the distal member 67 at the distal end side more than the coil sheath 66 with respect to the coil sheath 66. The inner diameter of the distal member 67 may be large such that the distal member 67 and the first locked portions 16, 17, the second locked portions 21, 22 do not engage with each other when the clip 10E described below is locked by the locking portion 32.

A step portion is formed on the inner circumferential surface of the distal end portion of the distal member 67 over the entire circumference. In the step portion, the surface facing the distal end side is the distal end support surface (distal end surface) 67b. A support portion 69 is formed at the distal end side more than the distal end support surface 67b. According to the present embodiment, the support portion 69 is formed in a cylindrical shape. The inner diameter of the support portion 69 is slightly larger than the outer diameter of the pressing tube 31E so as to be capable of receiving the proximal end of the pressing tube 31E. The distal end support surface 67b may contact the proximal end surface of the pressing tube 31E. The clip 10E is disposed at the distal end side of the sheath 61. The support portion 69 may support the outer circumferential surface of the pressing tube 31E that is in contact with the distal end support surface 67b.

According to these configurations, the unstableness of the clip 10E with respect to the support portion 69 may be suppressed as small as possible, and the inclination of the clip 10E with respect to the support portion 69 may be acceptable. Accordingly, the endoscope clip 1E may be smoothly inserted into the channel of the endoscope or the like even formed in a bent shape.

(Configuration of Operation Portion 100)

As shown in FIG. 22A, the endoscope clip 1E according to the present embodiment has the operation portion 100 including the operation portion main body (handle) 101, the slider 102, and the limiting portion 64. The operation portion 100 according to the present embodiment has the same configuration as the operation unit of the endoscope clip according to each of the above-described embodiments.

(Operation of Endoscope Clip 1E)

Hereinafter, the operation of treating the target tissue T using the endoscope clip 1E according to the present embodiment will be described.

(Closed Configuration)

As shown in FIGS. 22A to 23, in the initial state of the endoscope clip 1E according to the present embodiment, the pressing tube 31E is retained by the distal member 67 due to the elastic force of the elastic member 36 in a state in which the proximal end surface thereof contacts the distal end support surface 67b of the distal member 67.

In this state, the elastic force of the elastic member 36 applies on the arm member 11E of the clip 10E to push the arm member 11E out of the pressing tube 31. That is, when the elastic force of the elastic member 36 is applied to the arm member 11, the stopper 72 is about to be moved toward the distal end side. However, in this state, the slider 102 is in contact with the limiting portion 64 in the operation portion 100 on the proximal end side. Accordingly, the state in which the stopper 72 and the fixing member 74 are in contact with each other is maintained. At this time, the stopper 72 and the fixing member 74 may be pressed against each other such that the deforming portion 74b of the fixing member 74 is slightly elastically deformed. The stopper 72 and the fixing member 74 may only be in contact with each other and not in a state of pressing against each other.

In the first arm 12 and the second arm 13 of the arm member 11E, a portion between the distal end and the proximal end thereof is in contact (engage) with the tapered surface 31a of the distal end portion of the pressing tube 31 and the inner wall of the outer sheath 50. The arm member 11E is in the closed configuration in which the distal end of the first arm 12 and the distal end of the second arm 13 are in contact with each other, or the distance between the distal end of the first arm 12 and the distal end of the second arm 13 is substantially zero.

(First Open Configuration)

As shown in FIG. 24, the operator operates the outer sheath operating portion 51 and pulls the outer sheath 50 back with respect to the insertion portion 60E of the treatment tool main body 40E so as to protrude the first arm 12 and the second arm 13 of the arm member 11E from the distal end portion of the channel of the endoscope.

At this time, the restriction to the first arm 12 and the second arm 13 by the outer sheath 50 is released. The first arm 12 and the second arm 13 of the arm member 11E are separated from each other by their elastic restoring force. As described above, the arm member 11E is biased toward the direction of itself protruding from the pressing tube 31E by the elastic restoring force of the first arm 12 and the second arm 13.

However, in the endoscope clip 1E according to the present embodiment, the sum of the fixing force F1 generated when the inner diameter of the fixing member 74 becomes substantially the same as the outer diameter of the stopper 72 and the fixing force F2 by the limiting portion 64 is set to be equal to or more than the elastic force of the elastic member 36. Accordingly, even when the restriction by the outer sheath 50 is released, the arm member 11E does not move any further. That is, the opening width between the first arm 12 and the second arm 13 of the arm member 11E does not enlarge any further.

As a result, movement of the arm member 11E together with the operation wire 62 to the distal end side is restricted. The configuration in which the first arm 12 and the second arm 13 of the arm member 11E are spaced apart from each other by a certain distance is maintained. That is, as shown in FIG. 24, the slider 102 is located at the neutral position, and the arm member 11E becomes the first open configuration in which the opening width between the first arm 12 and the second arm 13 is the first distance W1.

The operator may use the arm member 11E in the first open configuration to grasp and treat the target tissue T by the same operations as the operations of using the endoscope clip 1 according to the first embodiment.

(Second Open Configuration)

When the arm member 11E of the clip 10E according to the present embodiment is in the first open configuration, in a case in which the first distance W1 as the opening width between the first arm 12 and the second arm 13 is smaller than the size of the target tissue T, the operator may cause the arm member 11E to be transitioned from the first open configuration to the second open configuration, and enlarges the opening width between the first arm 12 and the second arm 13 to the second distance W2 as the maximum opening width.

At this time, the operator may remove the limiting portion 64 from the slit 101b of the operation portion main body 101 and push the slider 102 toward the distal end side. When the operator pushes the slider 102 toward the distal end side, the stopper 72A provided at the distal end side of the operation wire 62 presses the fixing member 74.

Accordingly, as shown in FIG. 25, the deforming portion 74b of the fixing member 74 rotates radially outward with respect to the axis C1 and is elastically deformed. More specifically, as shown in FIG. 26, the stopper 72 is in contact with the elastically deformed deforming portion 74b of the fixing member 74 and is pressed into the inner cavity of the fixing member 74 by the operator pushing the slider 102. As shown in FIG. 27, the stopper 72 may pass through the inner cavity of the fixing member 74 while the deforming portion 74b of the fixing member 74 is elastically deformed. At this time, the engagement state between the stopper 72 and the fixing member 74 is released, and the deforming portion 74b of the fixing member 74 is restored to the initial shape.

At this time, the arm member 11E connected to the distal end side of the operation wire 62 moves to the distal end side together with the operation wire 62. The arm member 11E is transitioned to a configuration in which the distance between the first arm 12 and the second arm 13 becomes a distance larger than the first distance W1. In this process, similar to each of the above-described embodiments, the operator may pull the slider 102 toward the proximal end side to cause the arm member 11E to be transitioned to the first open configuration again. As a result, for example, the opening width of the arm member 11 may be adjusted corresponding to the target tissue T to be treated. For example, when treating different target tissues T to be treated, it is easy to handle the treatment tool while preventing the opened first arm 12 and the second arm 13 of the arm member 11 from unintentionally contacting the body wall.

As shown in FIGS. 28 and 29, when the stopper 72 comes into contact with the step portion 68 of the distal member 67 by the operator pushing the slider 102, the operation wire 62 and the arm member 11E are impossible to move further toward the distal end side. Accordingly, the arm member 11E is in the second open configuration in which the opening width between the first arm 12 and the second arm 13 is the second distance W2.

After that, the operator uses the arm member 11E in the second open configuration to grasp and treat the target tissue T by the same operations as the operations when using the endoscope clip 1 according to the first embodiment.
(Locked State)

When the operator confirms that the target tissue T is located between the first arm 12 and the second arm 13, the operator may grasp the operation portion main body 101 and pulls back the slider 102. At this time, the first arm 12 and the second arm 13 are moved to the proximal end side together with the operation wire 62. The opening width between the first arm 12 and the second arm 13 is reduced, and the target tissue T may be grasped. As shown in FIG. 30, in a state in which the target tissue T is grasped by the first arm 12 and the second arm 13 of the arm member 11E, the operator further pulls back the slider 102 such that the stopper 72 may be moved from the distal end side to overcome the inner cavity of the fixing member 74 again. At this time, since the stopper 72 and the fixing member 74 are engaged with each other, the state in which the target tissue T is grasped may be maintained even if the operator does not grasp the slider.

Subsequently, the operator further pulls the slider 102 back to the proximal end side such that the first locked portions 16, 17 and the second locked portions 21, 22 of the arm member 11 may overcome the locking portion 32 of the pressing tube 31E again and move to the position at the proximal end side more than the locking portion 32.

As shown in FIGS. 31A and 31B, at this time, both the distal end surface 16b of the first locked portion 16 and the distal end surface 17b of the first locked portion 17 contact the proximal end surface 32b of the locking portion 32, and the first locked portion 16 and the first locked portion 17 are locked by the locking portion 32. Similarly, both the distal end surface (not shown) of the second engaged portion 21 and the distal end surface (not shown) of the second engaged portion 22 contact the proximal end surface 32b of the locking portion 32, and the second engaged portion 21 and the second engaged portion 22 are locked by the locking portion 32. At this time, the arm member 11E is in the closed configuration in which the distance between the first arm 12 and the second arm 13 is substantially zero. That is, the root of the target tissue T is tightly bound by the first arm 12 and the second arm 13 of the arm member 11E.

When the clip 10E is in the locked state, the elastic member 36 provided in the pressing tube 31E is in a tightly wound state in which the strands 36a adjacent to each other in the axial direction Y are substantially in close contact with each other. The stopper 72 is located at a position apart from the fixing member 74 at the proximal end side of the fixing member 74. In this state, in the clip 10E, the locking force generated when the first locked portions 16, 17 are locked to the proximal end surface 32b of the locking portion 32 and the elastic force of the elastic member 36 are in balance. Accordingly, the support portion 69 formed at the distal end side of the distal member 67 does not support the outer circumferential surface of the pressing tube 31E that is in contact with the distal end support surface 67b.

As a result, when the operator pushes the slider 102, both the operation wire 62 and the clip 10E may move to the distal end side.
(Release State)

When the operator pushes the slider 102, the arm member 11E and the pressing tube 31E are integrated and moved to the distal end side. As shown in FIG. 32, when the connection structure between the hook 77 and the central portion 14 of the arm member 11E is positioned outside the pressing tube 31 by the operator pushing the slider 102, the hook 77 may rotate relative to the loop portion 73. When the operator operates the operation wire 62 and rotates the hook 77 in the direction D, the engagement between the hook 77 and the central portion 14 may be released.

As a result, the target tissue T can be indwelled in the body while being ligated by the clip 10E in the closed configuration. Subsequently, the operator performs necessary procedures such as accommodating the hook 77 in the sheath 61 and finishes the series of procedures.
(Effect of the Endoscope Clip 1E)

According to the endoscope clip 1E of the present embodiment, the movement of the operation wire 62 toward the distal end side may be restricted by the stopper 72 and the fixed portion 74 of the restriction portion 75 disposed in the insertion portion 60 being engaged with each other. In other words, according to the endoscope clip 1E of the present embodiment, the restriction portion 75 provided in the insertion portion 60E may restrict the transition of the arm member 11E from the first open configuration to the second open configuration.

Accordingly, similar to the endoscope clip according to each of the above-described embodiments, the opening width between the first arm 12 and the second arm 13 of the arm member 11E may be changed in stages. As a result, during the actual treatment, at the time of adjusting the orientation, the opening width, and the like of the clip 10E corresponding to the size of the target tissue T that is most often treated as the treatment target, the operation of adjusting the endoscope clip 1E may be shortened such that it is possible to improve the maneuverability, the procedure time, and the efficiency.

The restriction portion 75 has a simple configuration including the stopper 72 and the fixing member 74 and is easy to manufacture, such that the endoscope clip 1 may be configured at low cost.

(Modification of Restriction Unit 75)

According to the present embodiment, the configuration in which the restriction portion 75 of the endoscope clip 1E includes the stopper 72 and the fixing member 74 has been described as an example; however, the configuration is not limited thereto. For example, as shown in FIG. 33A, a restriction portion 85 including an engaged portion 84 and a stopper (engaging portion) 72 may be arranged in the insertion portion 60E of the endoscope clip 1E.

Figure 33A:
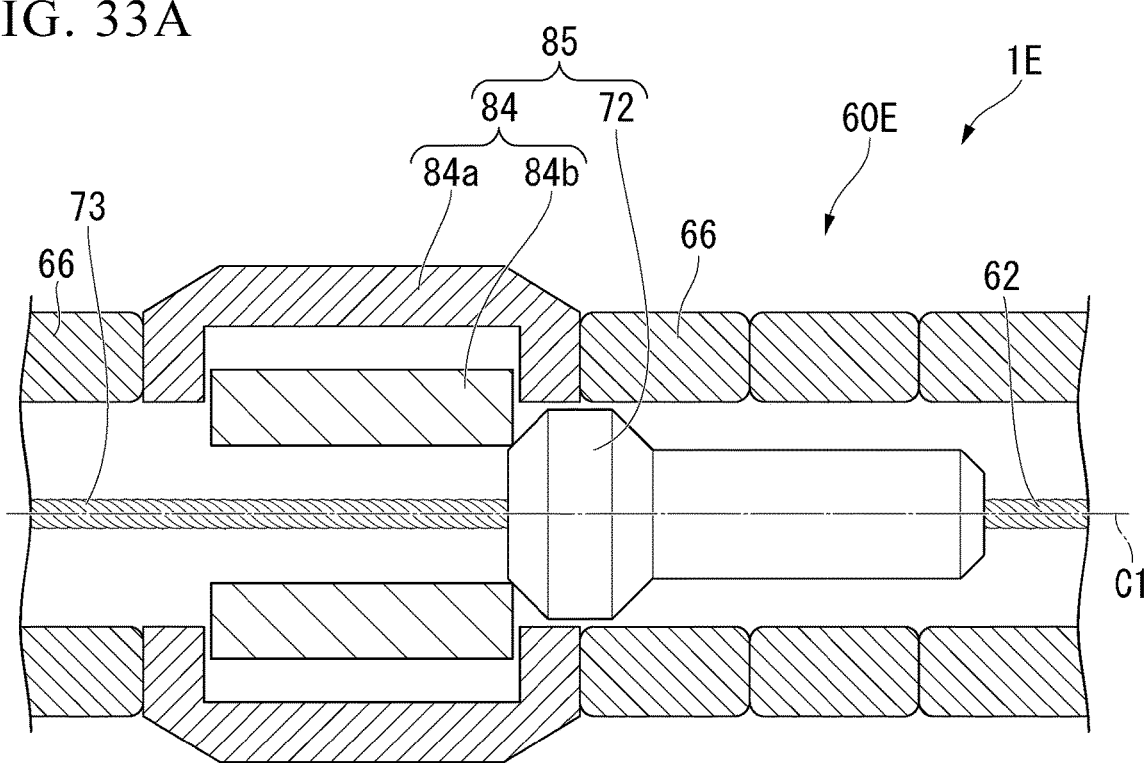
FIG. 33A is a cross-sectional side view schematically showing a configuration of an endoscope clip according to a modification of the present embodiment.

As shown in FIG. 33A, the engaged portion 84 of the restriction portion 85 according to the present modification includes a support member 84a and a C-shaped ring member (deforming portion) 84b. A distal end and a proximal end of the support member 84a is connected to the strand wire forming the coil sheath 66, and the support member 84 is formed integrally with the coil sheath 66. According to the present modification, the support member 84a may be integrally formed with the coil sheath 66 by a method such as welding or the like.

According to the present modification, as shown in FIG. 33A, the support member 84a is not limited to the example in which the support member 84a is sandwiched between the strand wires forming the coil sheath 66. For example, the support member 84a may be arranged at the distal end side more than the coil-sheath 66, and the proximal end of the support member 84a along the axial direction Y may be fixed to the strand wire forming the coil sheath 66 by a method such as welding, bonding or the like.

As shown in FIG. 33A, the outer diameter of the support member 84a of the engaged portion 84 in the radial direction with respect to the axis C1 may be slightly larger than the outer diameter of the coil sheath 66. The support member 84a is formed in a tubular shape, and has an inner cavity capable of accommodating the ring member 84b therein.

The ring member 84b may have the same configuration as that of the ring member 152 shown in FIG. 11D, for example. However, the ring member 84b is not limited to this configuration. For example, the ring member 84b may be formed by cutting a part of a tubular member.

As shown in FIG. 33A, in the natural state in which no external force applies, a space having an inner diameter smaller than the outer diameter of the stopper 72 is formed inside the ring member 84b. The engaged portion 84 is configured by combining the ring member 84b and the support member 84a such that the ring member 84b is rotatable in the inner cavity of the support member 84a and the ring member 84b does not slip from the inner cavity thereof.

Figure 33B:
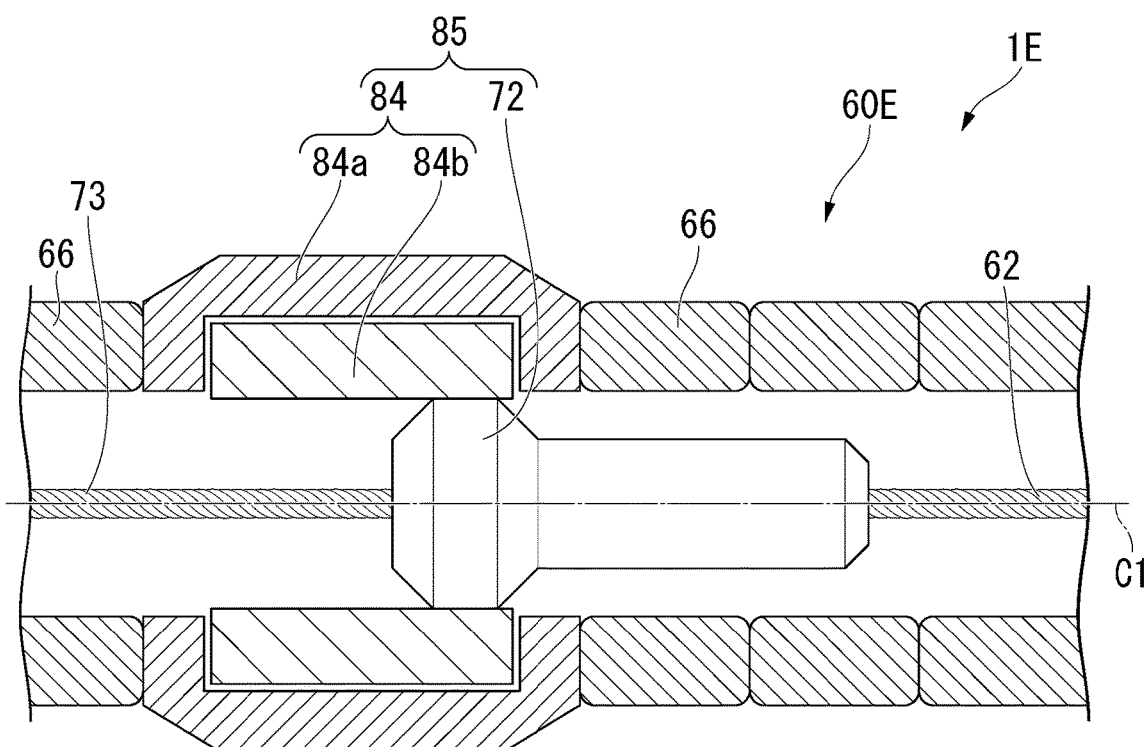
FIG. 33B is a cross-sectional side view schematically showing the configuration of the endoscope clip according to the modification of the present embodiment.

As shown in FIG. 33B, when the operator pushes the slider 102, the stopper 72 moves toward the distal end side with respect to the ring member 84b, and when the stopper member 72 overcomes the ring member 84, the restriction to the movement of the operation wire 62 toward the distal end side by the restriction portion 85 is released and the restriction to the restriction of the arm member 11 from the first open configuration to the second open configuration by the restriction portion 85 is also released. Subsequently, the target tissue T may be treated by the same operations as the operations using the endoscope clip 1E according to the sixth embodiment described above.

Figure 34A:
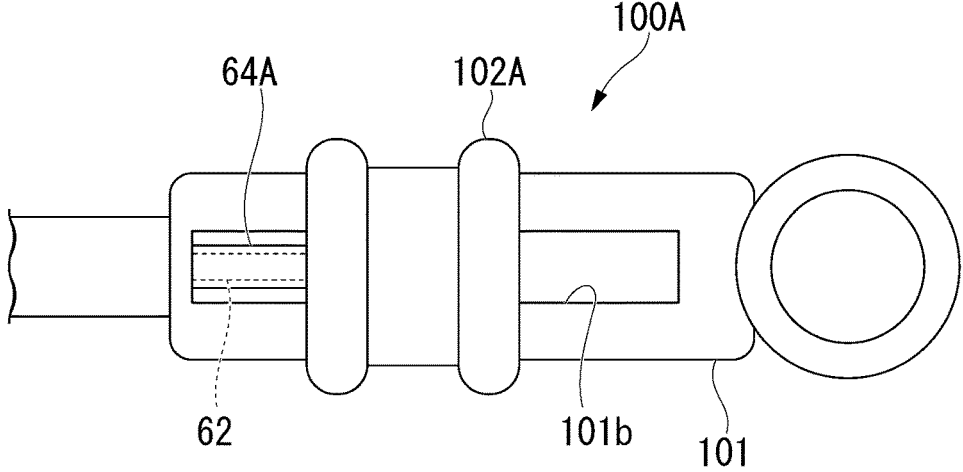
FIG. 34A is a side view showing a configuration of an operation portion of an endoscope clip according to a first modification of the present disclosure.
Figure 34B:
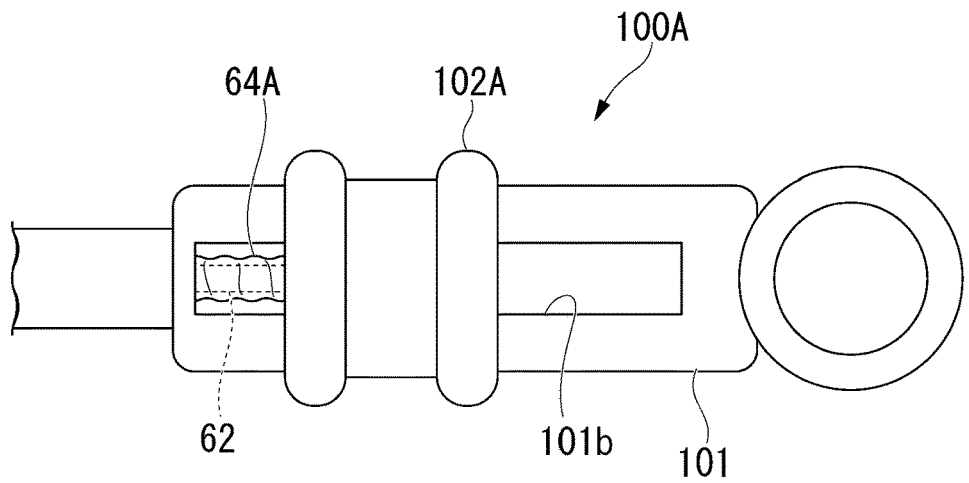
FIG. 34B is a side view showing movement of the operation portion according to the present modification.
Figure 35A:
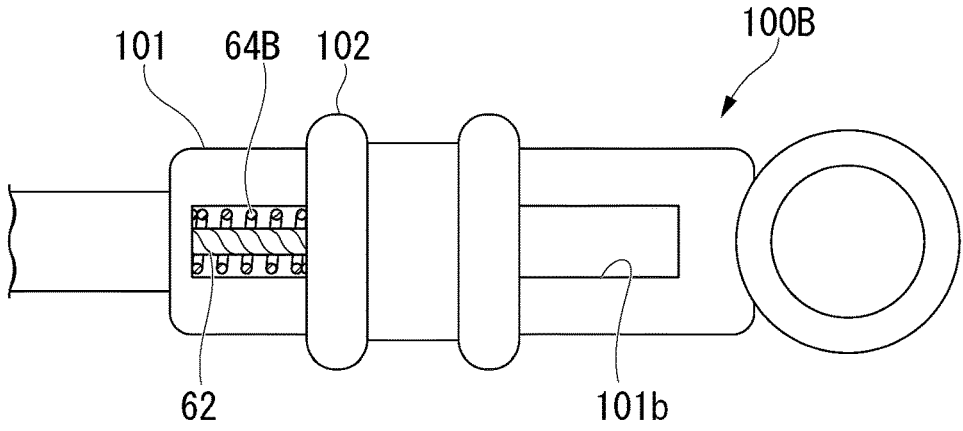
FIG. 35A is a side view showing a configuration of an operation portion of an endoscope clip according to a second modification of the present disclosure.

Hereinafter, with reference to FIG. 34A to FIG. 38, modifications of the operation portion of the endoscope clip according to each embodiment of the present invention will be described. FIGS. 34A and 34B are side views schematically showing the configuration of a first modification of the operation unit. FIGS. 35A and 35B are side views schematically showing the configuration of a second modification of the operation unit. FIGS. 36A to 36C are side views schematically showing the configuration of a third modification of the operation unit. FIG. 37 is a side view schematically showing the configuration of a fourth modification example of the operation unit. FIG. 38 is a side view schematically showing the configuration of a fifth modification of the operation unit.

In the following description, different aspects from the configuration of the operation unit of the endoscope clip according to each embodiment of the present disclosure will be mainly described.

First Modification

FIG. 34A shows an operation portion 100A according to the first modification. As shown in FIG. 34A, the operation portion 100A includes a limiting portion 64A made of a material that is elastically deformable to a certain extent when receiving a pressure along the longitudinal axis of the operation portion 100A itself. According to the present modification, the limiting portion 64A is formed to have the same dimension as that of the limiting portion 64 according to each of the above-described embodiments in a state where no pressure is applied in the longitudinal axis direction. According to the present modification, in the state where the slider 102A is in contact with the limiting portion 64A, the endoscope clip is in the first open configuration in which the opening width between the first arm 12 and the second arm 13 of the arm member 11 is the first distance W1.

Different from the endoscope clip 1 according to the above-described first embodiment, in this modification, the operator may further push the slider 102A even when the slider 102A is in contact with the limiting portion 64A. When the operator pushes the slider 102A, the limiting portion 64A in contact with the slider 102A is compressed in the longitudinal axis direction and elastically deformed. As shown in FIG. 34B, since the dimension of the elastically deformed limiting portion 64A in the longitudinal axis direction is reduced, the movable range of the slider 102A in the slit 101b is increased by the amount of the decrease amount of the limiting portion 64A.

As a result, the first arm 12 and the second arm 13 of the arm member 11 may be further opened from the first open configuration. That is, the arm member 11 of the endoscope clip according to the present modification may be transitioned to a configuration having an opening width slightly larger than that of the first open configuration. However, the opening width of the arm member 11 at this time is smaller than the second distance W2 as the opening width according to the second open configuration. Accordingly, the endoscope clip including the operation portion 100A according to the present modification is applicable to the target tissue T having an intermediate dimension between the first distance W1 and the second distance W2.

According to the present modification, when the operator pushes the slider 102A, in a case in which the limiting portion 64A reaches the limit of elastic deformation; however, the opening width of the arm member 11 is still smaller than the dimension of the target tissue T, it is possible to remove the limiting portion 64A to correspond to the dimension of the target tissue T.

Second Modification

FIG. 35A is a side view schematically showing the operation portion 100B according to the present modification. As shown in FIG. 35A, the operation portion 100B according to the present modification is provided with an elastic member (spring) 64B that connects the distal end surface 101d of the slit 101b of the operation portion main body 101B and the distal end surface of the slider 102B. A method of connecting the elastic member 64B to the distal end surface 101d of the slit 101b of the operation portion main body 101B and the distal end surface of the slider 102B is not particularly limited, and various known methods can be used.

The elastic member 64B according to the present modification has a free length same as the length of the limiting portion 64 according to the first embodiment in the state where no external force applies. Accordingly, in the present modification, the slider 102B is at the same position as the position where the slider 102 contacts the limiting portion 64 according to the first embodiment when the operator does not operate the slider 102B. That is, according to the operation portion 100B according to the present modification, in this state, the first open configuration in which the opening width between the first arm 12 and the second arm 13 of the arm member 11 is the first distance W1 may be maintained.

In the above description, it is described that the slider 102B is at the same position as the position where the slider 102 contacts the limiting portion 64 in the first embodiment when the operator does not operate the slider 102B. Actually, the elastic force of the elastic member 36 provided inside the pressing tube 31 applies to the arm member 11 and biases the arm member 11 toward the distal end side such that the elastic member 64B is compressed along the direction of the axis C1. However, in this modification, the elastic member 64B is configured to have an elastic force larger than that of the elastic member 36. That is, in the natural state where no external force applies, the compression amount of the elastic member 64B only by the elastic force of the elastic member 36 is substantially zero. Accordingly, in this state, the slider 102B is considered to be at the same position as the position where the slider 102 contacts the limiting portion 64 according to the first embodiment.

As shown in FIG. 35B, when the operator pushes in the slider 102, the elastic member 64B is compressed along the direction of the axis C1. At the same time, the operation wire 62 connected to the slider 102 and the arm member 11 connected to the operation wire 62 can move forward with respect to the operation portion main body 101. That is, according to the endoscope clip having the operation portion 100B according to the present modification, the arm member 11 can be transitioned from the first open configuration to the second open configuration by pushing the slider 102B.

Third Modification

Hereinafter, an operation portion 100C according to a third modification will be described with reference to FIGS. 36A, 36B, and 36C.

As shown in FIGS. 36A and 36B, the operation portion 100C according to the present modification has a configuration to limit advancement of the slider 202 with respect to the operation unit main body 201 by using a ratchet mechanism.

More specifically, as shown in FIG. 36A and FIG. 36B, in the operating portion 100C according to the present modification, a protrusion (first protrusion) 201c is disposed on an inner circumferential surface of the slit 201b of the operating portion main body 201, and a ratchet mechanism 202a is provided in the slider 202. The ratchet mechanism 202a of the slider 202 has a button 202b, a spring 202c, and a protrusion (second protrusion) 202d.

As shown in FIG. 36B, the protrusion 201c has a right triangle shape in a cross section taken along a plane passing through the central axis of the slit 201b. The protrusion 201c has a wall portion 201d formed to be orthogonal to the inner circumferential surface of the slit 201b, and an inclined portion 201e formed in an inclined surface shape. The inclined portion 201e is sequentially separated from the inner circumferential surface of the slit 201b toward the proximal end of the operation portion main body 201. A connection portion between the wall portion 201d and the inclined portion 201e is located at a position having the largest distance from the inner circumferential surface of the slit 201b in the protrusion 201c. The distance from the inner circumferential surface of the slit 201b to the connecting portion between the wall portion 201d and the inclined portion 201e is defined as a height of the protrusion 201c. The distance from the wall 201d to the distal end surface of the slit 201b is equal to the length of the limiting portion 64 of the endoscope clip 1 in the longitudinal axis direction according to the first embodiment.

The protrusion 202d of the ratchet mechanism 202a has a wall portion 202e formed in parallel with the wall portion 201d of the protrusion 201c and an inclined portion 202f formed in a slope shape. The spring 202c of the ratchet mechanism 202a biases the protrusion 202d in the radial direction such that when the operator advances the slider 202 along the central axis direction of the endoscope clip 2, the wall portion 201d and the wall portion 202e are in contact with each other. In this state, even if the operator further pushes the slider 202 toward the distal end side, the slider 202 does not move forward due to the contact and engagement between the wall portion 201d and the wall portion 202e. That is, the advancement of the slider 202 along the central axis of the operation portion main body 201 is restricted by the protrusion 201c and the protrusion 202d engaging with each other.

In this state, the position of the slider 202 is the same as the position of the slider 102 when the arm member 11 of the endoscope clip 1 according to the first embodiment described above is in the first open configuration. That is, in the present modification, the protrusion 201c of the slit 201b and the protrusion 202d of the slider 202 are engaged with each other such that arm member 11 is in the first open configuration in which the opening width between the first arm 12 and the second arm 13 is the first distance W1, and the transition from the first open configuration to the second open configuration is restricted.

When the operator confirms that the distance between the first arm 12 and the second arm 13 is smaller than the dimension of the target tissue T, it is necessary for the operator to enlarge the opening width of the arm member 11. At this time, the operator has to further advance the slider 202 from the position of the protrusion 201c of the operation portion main body 201.

In the state in which the protrusion 201c of the slit 201b and the protrusion 202d of the slider 202 are engaged with each other, when the operator pushes the button 202b of the ratchet mechanism 202a, the protrusion 202d of the ratchet mechanism 202a moves in the radial direction of the operation portion main body 201 (the direction intersecting the longitudinal axis direction of the part). As a result, the engagement state between the protrusion 201c of the slit 201b and the protrusion 202d of the slider 202 is released, and the slider 202 may be advanced along the central axis of the operation portion main body 201.

As shown in FIG. 36C, the operator may further advance the slider 202 to enlarge the opening width of the first arm 12 and the second arm 13 to the second distance W2. By such an operation, the operator may cause the arm member 11 to be transitioned from the first open configuration to the second open configuration.

In the state in which the slider 202 exceeds the protrusion 201c of the slit 201b, the operator pulls the slider 202 toward the proximal end side such that the inclined portion 202f of the protrusion 202d may move to the proximal end side while contacting the inclined surface of the protrusion 201c. As a result, the arm member 11 may be transitioned from the second open configuration to the first open configuration again only by the operation of the operator pulling the slider 202 toward the proximal end side.

According to the present modification, an example in which the protrusion 201c of the slit 201b and the protrusion 202d of the slider 202 have the right triangle shape in cross section has been described; however, the configuration of the endoscope clip 2C is not limited thereto. The endoscope clip 2C according to the present modification only has to have a configuration in which the slider 202 cannot relatively advance with respect to the operation section body 201 due to the engagement between the operation portion main body 201 and the slider 202. The specific aspect of the engagement between the operation portion main body 201 and the slider 202 is not particularly limited.

Fourth Modification

Hereinafter, the operation portion 100D according to a fourth modification will be described with reference to FIG. 37.

As shown in FIG. 37, in the operation portion 100D according to the present modification, a plurality of small protrusions (first protrusions) 301c and a large protrusion (third protrusion) 301d are formed on the inner circumferential surface of the slit 301b of the operation portion main body 301 along the longitudinal axis direction of the operation portion main body 301. Each of the plurality of small protrusions 301c has the same configuration as the protrusion 201c of the endoscope clip 2C according to the third modification. The large protrusion 301d has a cross-section in a right-angled triangular shape that is taken along a plane passing through the central axis of the slit 301b, and has a height higher than that of the small protrusions 301c. For example, the large protrusion 301d may have the height twice of that of the small protrusion 301c. According to the present modification, the distance from the wall portion of the large protrusion 301d to the distal end surface of the slit 301b is equal to the length of the limiting portion 64 of the endoscope clip 1 in the longitudinal axis direction according to the first embodiment.

The slider 302 according to the present modification has a ratchet mechanism 302a. The ratchet mechanism 302a has a button 302b, a spring 302c, and a protrusion (second protrusion) 302d. According to the present modification, the button 302b of the ratchet mechanism 302a may be pushed in two stages. For example, when the operator half-presses the button 302b of the ratchet mechanism 302a according to the present modification with a force equivalent to the force of pushing the button 202b of the ratchet mechanism 202a according to the second modification, the engagement between the protrusion 302d of the ratchet mechanism 302a and the small protrusions 301c of the operation portion main body 301 may be released. The operator may release the engagement between the protrusion 302d of the ratchet mechanism 302a and the large protrusion 301d of the operation portion main body 301 by fully pressing the button 302b of the ratchet mechanism 302a.

According to the endoscope clip having the operation portion 100D according to the present modification, when the operator once half-presses the button 302b of the ratchet mechanism 302a, the slider 302 may be advanced along the longitudinal axis direction of the operation portion main body 301 until the protrusion 302d of the ratchet mechanism 302a contacts the next small protrusion 301c. Accordingly, when the plurality of small protrusions 301c are continuously disposed on the inner circumferential surface of the operation portion main body 301, the slider 302 may advance at only a certain distance for each time when the operator half-presses the button 302b.

On the other hand, the operator may advance the slider 302 along the longitudinal axis direction of the operation section body 301 by continuing half-pressing the button 302b of the ratchet mechanism 302a. In this case, the operator may advance the slider 302 until the protrusion 302d of the ratchet mechanism 302a contacts the large protrusion 301d. When the protrusion 302d of the ratchet mechanism 302a comes into contact with the large protrusion 301d, similar to the endoscope clip 1 according to the above-described embodiment 1, the opening width between the first arm 12 and the second arm 13 becomes the first distance, and the arm member 11 is in the first open configuration.

Even if the operator pushes the slider 302 along the longitudinal axis direction of the operation section main body 301 in a state in which the arm member 11 is in the first open configuration, due to the engagement of the protrusion 302d of the ratchet mechanism 302a and the large protrusion 301d of the operation section main body 301, the movement of the slider 302 toward the distal end side is restricted, and the transition of the arm member 11 from the first open configuration to the fully open second open configuration is restricted.

In this case, by the operator fully pushing the button 302b of the ratchet mechanism 302a, the protrusion 302d of the ratchet mechanism 302a moves in the radial direction of the operation section main body 301 and climbs on and overcomes the large protrusion 301d of the operation section main body 301. At this time, the engagement of the protrusion 302d of the ratchet mechanism 302a and the large protrusion 301*d* of the operation portion main body 301 is released, and the operator may further advance the slider 302.

As a result, in the endoscope clip having the operation portion 100D according to the present modification, the opening width between the first arm 12 and the second arm 13 of the arm member 11 may be further enlarged from the first distance W1 to the second distance W2. That is, the operator may cause the arm member 11 having the operation portion 100D according to the present modification to be transitioned from the first open configuration to the second open configuration.

According to the endoscope clip having the operation portion 100D according to the present modification, the slider 302 can move forward substantially the same distance each time the operator half-presses the button 302*b* of the ratchet mechanism 302*a* of the slider 302. Therefore, the operator can finely adjust the opening width of the arm member 11 by a simple operation.

Fifth Modification

Hereinafter, with reference to FIG. 38, an operation portion 100E according to a fifth modification of the present invention will be described. The operation portion 100E according to the present modification has a plurality of small protrusions (first protrusions) 301*c* and a single large protrusion (third protrusion) 301*d* formed on the inner circumferential surface of the slit 301*b* of the operation unit body 101C along the longitudinal axis direction of the operation portion main body 101C. The plurality of small protrusions 301*c* and the large protrusion 301*d* have a cross section in a substantially equilateral triangular shape. The slider 302 of the endoscope clip 2E according to the present modification includes a ratchet mechanism 302*a* having a protrusion (second protrusion) 302*d* formed in a substantially equilateral triangle shape.

According to the endoscope clip having the operation portion 100E according to the present modification, when the operator pushes the slider 302 toward the distal end side along the central axis direction of the operation portion main body 101C, the protrusion 302*d* of the slider 302 moves toward the distal end side along the inclined portion of the small protrusion 301*c* contacting the protrusion 302*d* of the slider 302 and climbs on and overcomes the small protrusion 301*c*.

In the endoscope clip having the operation portion 100E according to the present modification, the large protrusion 301*d* has a height such that it is impossible for the protrusion 302*d* to overcome the protrusion 301*d* due to the pressing force by the operator along the central axis direction of the operation portion main body 101C. Accordingly, when the slider 302 advances to a position to come in contact with the large protrusion 301*d*, it is necessary for the operator to fully push the button 302*b* of the ratchet mechanism 302*a*. When the operator fully pushes the button 302*b* of the ratchet mechanism 302*a* and advances the slider 302 toward the distal end side, the restriction due to the engagement of the protrusion 302*d* of the ratchet mechanism 302*a* and the large protrusion 301*d* may be released.

In the above description, the plurality of small protrusions 301*c* and the large protrusion 301*d* provided on the operation portion main body 101C and the protrusion 302*d* of the ratchet mechanism 302*a* have been described to have a substantially equilateral triangular cross-sectional shape; however, the configuration is not limited thereto. For example, each of the plurality of small protrusions 301*c*, the one large protrusion 301*d*, and the protrusion 302*d* may have a cross section formed in an isosceles triangle shape.

According to the endoscope clip having the operation unit 101C according to the present modification, there is no necessity to differentiate the half-pressing operation and the full-pressing operation to the button 302*b* of the ratchet mechanism 302*a*, and it is possible to prevent any operation error.

Although the respective embodiments and modifications of the present invention have been described above, the technical scope of the present invention is not limited to the above-described embodiments, and configurations in the respective embodiments and modifications within the scope not departing from the spirit of the present invention. It is possible to change the combination of elements, make various changes to each constituent element, or delete each constituent element. For example, the configuration of the clip unit in the endoscope clip according to any one of the first to fifth embodiments of the present invention may be appropriately combined with each modification of the operation section. The disclosure is not limited by the above description, but only by the appended claims.

In the first embodiment of the present invention, the example in which the limiting portion 64 is disposed on the distal side of the slider 102 has been described. However, the position where the limiting portion 64 is disposed is not particularly limited as long as the advanceable range of the slider 102 along the longitudinal axis direction of the operation portion 100 may be restricted by the engagement between the limiting portion 64 and the slider 102.

In the first embodiment of the present invention, the example in which the limiting portion 64 is made of a resin material has been described. However, the limiting portion 64 only has to be formed with a rigidity that the limiting portion 64 is not compressed even if a constant pressure in the longitudinal axis direction is applied to the limiting portion 64 itself. The material forming the limiting portion 64 is not particularly limited. For example, the limiting portion 64 may be a metallic tubular member.

According to the first embodiment of the present invention, the example in which the corresponding inclined surfaces are formed on each of the protrusions 18, 19, 23, 24 and the step portion 15 has been described. However, the protrusions 18, 19, 23, 24 and the step portion 15 only have to be configured such that the protrusions 18, 19, 23, 24 may easily climb on and overcome the step portion 15 due to the relative movement of the protrusions 18, 19, 23, 24 and the step portion 15. The inclined surfaces provided in the protrusions 18, 19, 23, 24 and the step portion 15 of the endoscope clip 1 according to the above-described first embodiment are not essential configurations.

In the first to sixth embodiments of the present disclosure, the example in which the limiting portion for restricting the forward movement of the operation wire is provided has been described. However, the configuration of the present invention is not limited to this. The endoscope clip of the present invention can achieve the same effect even when the limiting portion is not arranged on the operation portion. That is, in the endoscope clip of the present invention, it is not essential for the limiting portion to be arranged on the operation portion.

In a general endoscopic treatment tool, there are cases in which the stroke, the rotation torque or the like generated by the operator operating the slider of the operation portion at the hand side of the operator are absorbed during the process of being transmitted to the distal end side of the endoscope treatment tool due to the meandering state of the insertion portion of the endoscopic treatment tool. That is, there is a difference between the operation amount by the operator operating to the operation portion and the movement amount at the distal end side of the endoscopic treatment tool such that the operator has to operate the operation portion by increasing the operation amount so as to obtain a desired operation amount.

Taking such a situation into consideration, for example, in the case of the endoscope clip according to the present disclosure, the stroke amount for changing the state of the arm member at the distal end side changes in corresponding to the bending degree of the insertion portion (sheath). As a result, it is difficult for the operator to recognize an appropriate operation amount.

In the endoscope clip according to the present disclosure, due to the limiting portion disposed on the operation portion on the proximal end side, even if the slider is pushed until coming in contact with the limiting portion, the configuration of the arm member is not transitioned (for example, transition from the first open configuration to the second open configuration). On the other hand, in the state in which the operator removes the limiting portion from the operation portion and pushes the slider until the slider comes into contact with the distal end surface of the slit of the operation portion main body, the configuration of the arm member may be transitioned.

Accordingly, during the operation, the operator only has to confirm the state of the limiting portion disposed in the operation portion at the hand side to easily recognize the configuration of the endoscope clip and the appropriate operations.

Figure 39:
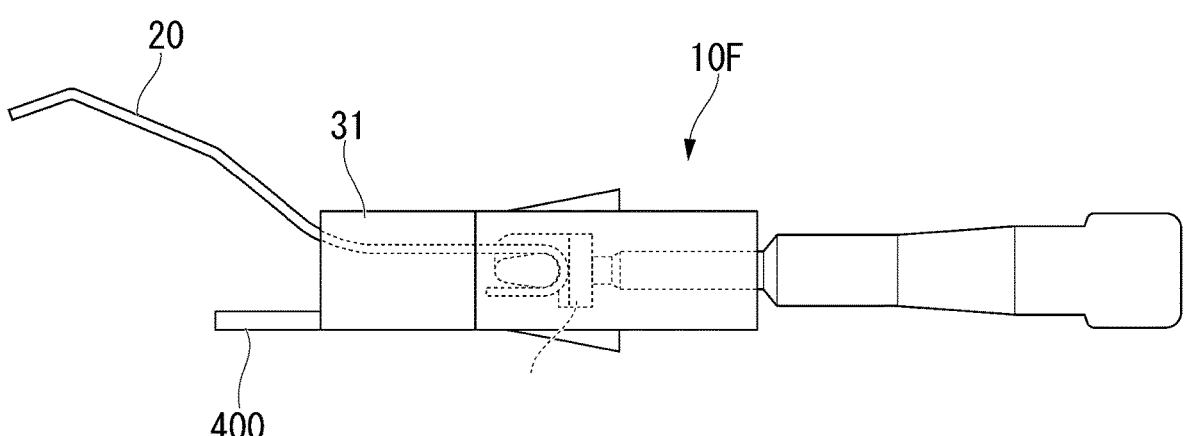
FIG. 39 is a view showing a configuration of a clip unit according to a modification of the present disclosure.

In each of the above-described embodiments, a configuration of the arm member having the pair of arms has been described as an example; however, the present disclosure is not limited only to this configuration. For example, as shown in FIG. 39, a clip unit having only one arm 20 may be configured. As shown in FIG. 39, a clip 10F has a rod-shaped member 400 fixed to the distal end surface of the pressing tube 31 and protruding from the distal end surface of the pressing tube 31 toward the distal end side.

According to the clip 10F configured in this manner, by advancing and retracting an operation wire (not shown), the arm 20 advances and retracts together with the operation wire while being in contact with the distal end surface of the pressing tube 31. For example, when the operator pulls back the operation wire to the proximal end side, the arm 20 connected to the operation wire is pulled back to the proximal end side together with the operation wire while contacting the distal end surface of the pressing tube 31. As a result, the distance between the arm 20 and the rod-shaped member 400 decreases as the arm 20 is pulled back.

In other words, in the clip 10F shown in FIG. 39, when the arm 20 and the rod-shaped member 400 are regarded as the first arm and the second arm of the arm members according to the above-described embodiments, respectively, the arm member may be transitioned from the open configuration to the closed configuration by only moving the arm member (first arm) 20 toward the proximal end side with respect to the pipe 31. Similarly, according to the clip 10F shown in FIG. 39, when the operator pushes the operation wire toward the distal end side, the arm member may be transitioned from the closed configuration to the open configuration by only pressing the arm (first arm) 20 toward the distal end side with respect to the pressing tube 31.

In the clip 10F, since only the arm 20 is movable with respect to the pressing tube 31, the arm 20 may be regarded as a moving portion of the arm member. The same effect may be achieved by applying the configuration of the clip 10F shown in FIG. 39 to each of the above-described embodiments and modifications.

What is claimed is:

1. An endoscope clip, comprising:
   a clip arm including a first arm and a second arm and extending along a longitudinal axis;
   an operation portion that includes a wire configured to cause the clip arm to transition between a closed configuration, a first configuration, and a second configuration,
   wherein:
   the first arm and the second arm are closed in the closed configuration,
   the first arm is spaced apart from the second arm at a first distance in the first configuration;
   the first arm is spaced apart from the second arm at a second distance that is larger than the first distance in the second configuration; and
   a stopper is configured to fix the clip arm in one of the first configuration or the second configuration and configured to release the clip arm to transition into a different configuration, wherein the wire is biased toward a distal side due to an elastic force, and the stopper is configured to apply a second force opposite the elastic force to fix the clip arm in one of the first configuration or the second configuration.

2. The endoscope clip according to claim 1, wherein when the clip arm is in the first configuration, the stopper is configured to apply a first force opposite to a moving direction of the clip arm in a first direction along the longitudinal axis to the clip arm so as to restrict movement of the clip arm in the first direction and to fix the clip arm in the first configuration.

3. The endoscope clip according to claim 2, further comprising a pressing tube having a longitudinal axis,
   wherein the stopper comprises:
   an engaging portion provided in the pressing tube; and
   an engaged portion disposed in the clip arm and configured to be engageable with the engaging portion,
   the clip arm is configured to transition from the first configuration to the second configuration in this sequence by relative movement with respect to the pressing tube, and
   when the clip arm is in the first configuration, the transition of the clip arm from the first configuration to the second configuration is restricted by an engagement of the engaging portion and the engaged portion.

4. The endoscope clip according to claim 3,
   wherein the engaging portion protrudes from an inner circumferential surface of the pressing tube toward an inner side of the pressing tube, and
   the engaged portion protrudes from at least one of the first arm and the second arm toward an outer surface of the pressing tube.

5. The endoscope clip according to claim 3,
   wherein the clip arm has a locked portion that protrudes from at least one of the first arm and the second arm toward an outer surface of the pressing tube,
   the pressing tube has a locking portion that protrudes from an inner circumferential surface of the pressing tube toward an inner side of the pressing tube,
   when the clip arm is in the closed configuration, the locking portion contacts the locked portion such that movement of the clip arm toward the pressing tube in the first direction is restricted and the clip arm is fixed in the closed configuration, and

when the clip arm is in the second configuration, a distance between the engaging portion and the engaged portion in the direction along the longitudinal axis is smaller than a distance between the locked portion and the locking portion in the direction along the longitudinal axis.

6. The endoscope clip according to claim 3,
wherein when the clip arm is in the first configuration, the first arm and the second arm is configured to engage with an inner circumferential surface of the pressing tube such that the clip arm is in a deformation state in which the first arm and the second arm approach each other, and
when the clip arm is in the second configuration, the engagement of the first arm and the second arm with the inner circumferential surface of the pressing tube is released respectively and the deformation state of the clip arm is released.

7. The endoscope clip according to claim 3, wherein the engaging portion is configured to detach from the pressing tube.

8. The endoscope clip according to claim 3, wherein the engagement of the engaging portion and the engaged portion is released by the clip arm moving along the first direction with respect to the pressing tube.

9. The endoscope clip according to claim 3, wherein at least one of the engaging portion and the engaged portion is a flap that is elastically deformable.

10. The endoscope clip according to claim 7,
wherein the engaging portion protrudes from an inner circumferential surface of the pressing tube toward an inner surface of the pressing tube, and
the engaged portion is a hole formed in a direction along the longitudinal axis and a part of the engaging portion is configured to penetrate the hole.

11. The endoscope clip according to claim 1,
wherein the operation portion comprises:
a handle; and
a slider configured to move with respect to the handle,

the clip arm is configured to transition to the closed configuration, the first configuration, and the second configuration due to movement of the slider,
the stopper is a limiting portion disposed in the handle and configured to restrict the movement of the slider.

12. The endoscope clip according to claim 11, wherein:
the limiting portion is disposed more distally than the slider,
when the movement of the slider is restricted by the limiting portion, the slider is configured to cause the clip arm to transition from the closed configuration to the first configuration by relative movement between the slider and the handle, and
when restriction to the movement of the slider is released, the slider is configured to transition the clip arm to the second configuration by the relative movement between the slider and the handle.

13. The endoscope clip according to claim 11,
wherein the limiting portion is configured to attach to and detach from the handle; and
when the limiting portion is attached to the handle, a movement range of the slider with respect to the handle is restricted, and when the limiting portion is detached from the handle, the restriction to the movement range of the slider with respect to the handle is released.

14. The endoscope clip according to claim 11,
wherein the slider is movable along a longitudinal axis of the handle,
the limiting portion comprises:
a first contact surface disposed in the handle;
a second contact surface disposed in the slider and configured to be in contact with the first contact surface; and
a slider configured to move at least one of the first contact surface and the second contact surface in a direction intersecting with the longitudinal axis of the handle, and
the movement range of the slider with respect to the handle is restricted when the first contact surface contacts the second contact surface.

* * * * *